United States Patent [19]

Taguchi

[11] Patent Number: 6,028,908
[45] Date of Patent: Feb. 22, 2000

[54] X-RAY CT SCANNING APPARATUS

[75] Inventor: Katsuyuki Taguchi, Tokyo, Japan

[73] Assignee: Kabushiki Kaisha Toshiba, Kawasaki, Japan

[21] Appl. No.: 09/023,710

[22] Filed: Feb. 13, 1998

[30]     Foreign Application Priority Data

Feb. 17, 1997  [JP]  Japan ..................................... 9-032252
Apr. 1, 1997   [JP]  Japan ..................................... 9-083092

[51] Int. Cl.$^7$ ............................................ A61B 6/00
[52] U.S. Cl. .................................. 378/15; 378/19; 378/4
[58] Field of Search ............................... 378/4, 15, 901, 378/19

[56]           References Cited

U.S. PATENT DOCUMENTS 4,682,290   7/1987  Tan et al. .
5,825,842  10/1998  Taguchi ...................................... 378/15
5,838,756  11/1998  Taguchi et al. ............................. 378/4

*Primary Examiner*—David P. Porta
*Assistant Examiner*—Michael J. Schwartz
*Attorney, Agent, or Firm*—Oblon, Spivak, McClelland, Maier & Neustadt, P.C.

[57]           ABSTRACT

There is provided an X-ray CT apparatus which can generate high density data from data acquired by virtue of a helical scan and then execute image reconstruction based on the high density data. The X-ray CT apparatus includes a first processed data generating unit for generating first processed data by applying first interpolation process to acquired direct data, a second processed data generating unit for generating second processed data by generating a group of complementary data and then applying second interpolation process to the group of complementary data, and a third processed data generating unit for generating third processed data, which is high density data having twice sampling point number, by putting the first processed data and the second processed data therebetween alternately.

30 Claims, 48 Drawing Sheets

Z-AXIS DIRECTION
(SLICE DIRECTION)

HELICAL SCAN

SUBJECT

1. PROJECTION DATA ACQUISITION AND CORRECTION AT ALL ANGLES

2. CONVOLUTION WITH RECONSTRUCTION FUNCTION

3. BACK PROJECTION OPERATION AT ALL ANGLES

BACK PROJECTION AT CERTAIN ANGLE

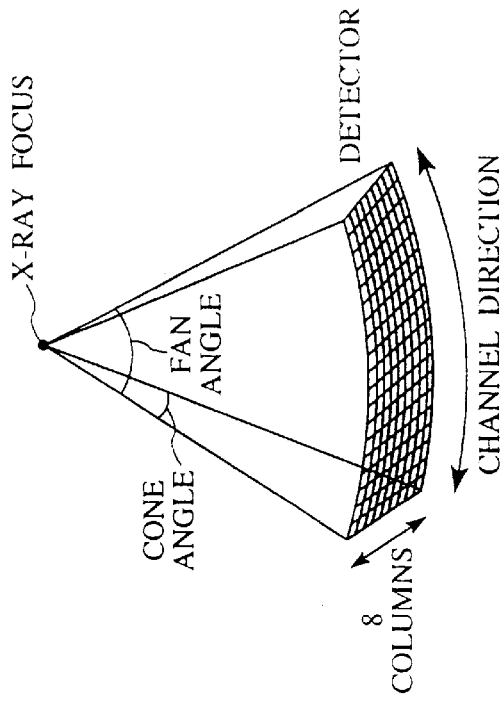
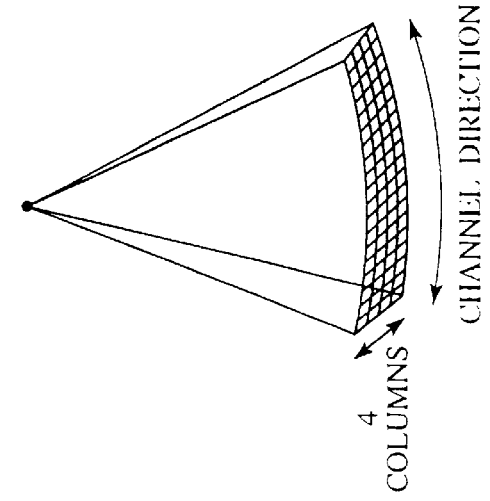
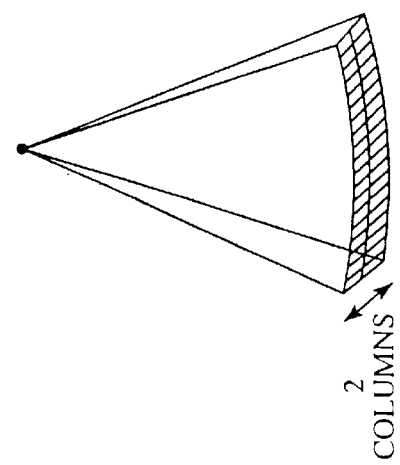
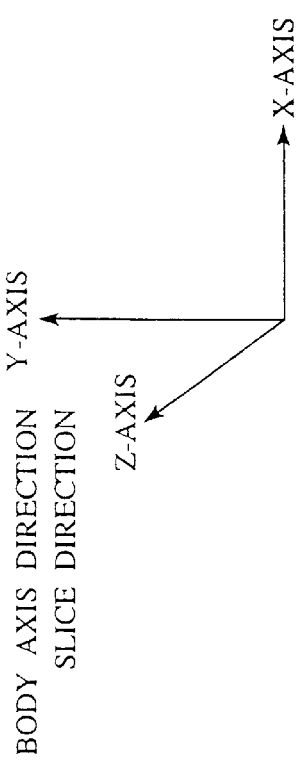
FIG. 21A  FIG. 21B  FIG. 21C

STANDARD FUNCTION

HIGH RESOLUTION FUNCTION
(EFFECTIVE SLICE
THICKNESS : THIN)

ULTRA HIGH
RESOLUTION FUNCTION
(EFFECTIVE SLICE
THICKNESS : ULTRA THIN)

LOW RESOLUTION FUNCTION
(EFFECTIVE SLICE
THICKNESS : THICK)

Pitch = 1.5 IN TWO COLUMN MULTI-SLICE CT

NEW COMPLEMENTARY BEAM INTERPOLATION
METHOD AT Pitch = 1.5 IN TWO COLUMN MULTI-SLICE CT NEW COMPLEMENTARY BEAM INTERPOLATION
METHOD AT Pitch=3.5 IN FOUR COLUMN MULTI-SLICE CT

X-RAY CT SCANNING APPARATUS

BACKGROUND OF THE INVENTION

1. Field of the Invention

The present invention relates to an X-ray CT apparatus and, more particularly, a technique for executing image reconstruction which can have both high spatial resolution on a trans-axial plane and excellent continuity along a body axis direction in a helical scan x-ray CT apparatus.

2. Description of the Prior Art

A scan system, etc. of an X-ray CT apparatus (abbreviated simply as "CT" hereinafter) which is used to take tomograms of a subject in the prior art will be explained in brief.

(1) Fan beam (single slice) X-ray CT

First, a single slice CT will be explained.

As shown in FIG. 1, the main current of present CTs is the single slice CT which comprises an X-ray focus for generating a X-ray beam (continuous fan beam along a channel direction), and a detector composed of sectorial or linear N-channel (e.g., 1000 channel) detecting elements which are arranged in a line.

The single slice CT can acquire intensity data of X-ray passing through the subject (called as "projection data" hereinafter) while rotating a pair of the X-ray focus and a detector around the subject. Projection data are acquired Nview times, e.g., 1000 times per one rotation and then image reconstruction is carried out based on the projection data according to a method to be described later.

Data acquisition per one time is called as "one view", data detected by one detecting element or a detecting element group in one view is called as "one beam", and all beams (data detected by all detecting elements) in one view is called as "direct data" in a lump.

Next, the scan system of CT will be explained. A conventional scan and a helical scan are two representative types of such scan system.

A first scan system is the conventional scan shown in FIG. 2.

This system is a scan system in which an X-ray focus is rotated around a target plane (e.g., plane A) by one rotation. In order to get images of plural planes (e.g., planes A and B), the CT first acquires data while rotating around the plane A by one rotation. Then, the plane B is set to a plane of rotation by moving either a patient couch on which the subject is laid down or the X-ray focus and the detector. Then, like the plane A, data are acquired while rotating around the plane shape B by one rotation.

Accordingly, in the conventional scan system, a scanning time becomes longer if a scanning range is broad in the body axis direction (Z-axis direction) of the subject or if a great number of target planes are needed.

A second scan system is the helical scan shown in FIG. 3.

In this system, while rotating continuously the X-ray focus and the detector and also moving the patient couch along a body axis direction of the subject synchronously with such rotation, the CT can acquire data. In other words, an X-ray focus orbit can scan helically around the subject. According to this scan system, a wide range can be scanned at high speed.

Where a coordinate system is defined as shown in FIG. 1. An XY plane corresponds to planes A, B to be scanned by the conventional scan, and a Z-axis direction is a body axis direction of the subject, which is called as a slice direction in the above single slice CT.

Next, an image reconstruction method will be explained. First of all, normal image reconstruction in the conventional scan system as the first scan system will be explained.

Such normal image reconstruction will be explained in brief with reference to FIG. 5 hereunder.

The conventional scan is made up of three following steps. Suppose that, as shown in FIG. 4, the subject only exists as an arrow signal indicating a center of rotation.

(i) Data acquisition and Correction

The CT executes first the conventional scan to acquire data. Normally, a rotation angle, though only shown partially, is 360°, 180°+fan angle, etc. Projection data are shown in FIG. 5A. Raw data can be derived by correcting the projection data with regard to various factors such as sensitivity of the detector, X-ray intensity, etc.

(ii) Convolution Using Reconstruction Function

Convolution of the raw data of respective angles and reconstruction functions is performed. Such convolution data are shown in FIG. 5C. Neighborhood of originally existing signals are recessed shapes.

(iii) Back Projection Operation

Convolution data are added to all pixels on X-ray passing paths when the data are collected. FIG. 5B shows back projection operation at a certain angle. If such pack projection operation is repeated at necessary angles, only original signals remain.

Processes (ii) and (iii) explained above, if combined with each other, are called a filter correction back projection method (convolution back projection method, i.e., CBP method).

Next, an image reconstruction system which is able to achieve high resolution in the image reconstruction of the above conventional scan will be explained.

This is a system which can achieve improvement in spatial resolution and therefore is so-called QQ (Quarter-Quarter) process to improve the spatial resolution from 0.50 mm to 0.35 mm, for example.

An outline of the QQ process will be explained hereunder.

The QQ is such a method that, as described above, normal spatial resolution is about 0.5 mm but spatial resolution of an axial image is improved up to about 0.35 mm, for example.

An trans-axial plane (XY plane) viewed from the Z-axis direction is shown in FIG. 6A. Assuming that a field of view FOV (effective field-of-view diameter) is 500 mm and the channel number of the detector is 1000, spatial resolution of the axial image obtained by the normal image reconstruction of the above conventional scan is about 0.50 mm. In FIG. 6, FCD (Focus-Center-Distance) denotes a distance between the X-ray focus and the center of rotation, and FDD (Focus-Detector-Distance) denotes a distance between the X-ray focus and the detector.

FIG. 7 is a view showing an so-called QQ offset fitting state wherein the detector which is composed of even-numbered elements (channels) aligned along the channel direction is not fitted symmetrically about the center line, but such detector is fitted to have an offset of a ¼ channel distance along the channel direction.

At this time, a path (indicated by an upward thick arrow) connecting a virtual k+0.5-th channel, which is located in the right middle between the k-th channel and the k+1-th channel in the j-th view, and the focus of the j-th view, as shown in FIG. 8A, coincides with a path (indicated by a downward thick arrow) connecting the focus of the j+x-th view and the y-th channel, as shown in FIG. 8B in which the detector is rotated by a half turn from FIG. 8A.

Hence, data of the y-th channel in the j+x view in FIG. 8B are data of the k+0.5 channel in the j-th view in FIG. 8A. Relationships among above j, k, x, y can be expressed by equations in the following.

$$y = \text{CentCH} \times 2 - (k+0.5)$$

$$x = \{[(k+0.5-\text{CentCH}) \times \phi]/[\text{Nch} \times 180] + 0.5\} \times \text{Nview} \quad \text{[Equation 1]}$$

Where $\phi:\text{Nch} = \psi:(k+0.5-\text{CentCH})$ and $(180+2\psi):x = 360:\text{Nview}$ (see FIG. 9)

Nview=view number per one time,
Nch=channel number,
$\phi$=fan angle,
$\psi$=angle relative to channel,
CentCH=center channel=(Nch+0.5)/2 (In the case of QQ offset fitting).

Accordingly, data of the virtual k+0.5 channel located between the k-th channel and the k+1-th channel can be derived from data of the y-th channel in the j+x-th view.

However, in the case of Nview=1000, Nch=1000, j=100, k=700, $\phi$ =50° in the above equations, y=300 channel and x=555.625 can be obtained, which yields such data in the 655.255-th view.

Therefore, data T-Data can be derived by interpolating data D (655, 300) of the 300-th channel in the 655-th view and data D (656, 300) of the 300-th channel in the 656-th view based on an integer portion Ix=int(x)=655 according to the following equations.

$$T.\text{Data} = (1-w) \times D(Ix, y) + w \times D(Ix+1, y) \quad \text{[Equation 2]}$$

Ix=int(x), w=x-Ix, D(j, k): data of the k-th channel in the j-th view

Data called complementary beam (see a reference B0 in FIG. 8B and FIG. 16 to be described later) are selected as data of the k+0.5-th channel in the target j-th view.

Data (complementary beams) of 0.5-th, 1.5-th, 2.5-th, 3.5-th, . . . , k+0.5-th, . . . , 999.5-th virtual channels, corresponding to all detecting elements, in the j-th view can be obtained in the same way.

Total complementary beams of all channels are called as the complementary data. Since x becomes decimal in substantially all cases, respective complementary beams can be obtained by virtue of two data interpolation of one channel× two views.

This process is repeated to respective Nviews.

With the use of 2×Nch channel data having double sampling point number (double sampling density) compared to normal conventional scan obtained by the above process, image reconstruction can be performed by means of the convolution and the back projection.

Since complementary data have been obtained by virtue of two data interpolation as described above, spatial resolution does not reach twice but it reaches 1.4 times which corresponds to spatial resolution of about 0.35 mm.

Again, a conception of QQ will be explained with reference to FIGS. 10 and 11.

Data in the j-th view will be considered. As indicated by a reference M1 in FIG. 10, by placing alternately direct data, which are acquired in the j-th view and indicated by solid lines, and complementary data, which are acquired by virtue of interpolation of one channel×two views and indicated by dotted lines, image reconstruction can be effected as data which are collected by the high sampling density detector having twice detecting element number. In other words, as shown in FIG. 11, reconstruction can be accomplished with the use of high density data which is constructed by arranging alternately direct data on an orbit of the conventional scan around the Z-axis direction (body axis direction) and complementary data obtained by interpolation. Consequently, improvement in spatial resolution of the trans-axial plane can be attained.

At that time, since the scan system employs the conventional scan, slice positions of direct data and complementary data (sampling positions along the Z-axis direction) are the same.

Then, image reconstruction in the helical scan system as the second scan system will be explained hereunder.

When the conventional scan and the helical scan as two scan systems shown in FIGS. 2 and 3 are viewed from this side, states of scan systems are shown in FIGS. 12 and 13 respectively. Abscissas indicate a slice (Z-axis) direction and ordinates indicate rotation phase (angle) respectively. Sampling positions of respective data are represented by connecting by arrows. Such diagrams are called scan views hereinafter.

In the conventional scan shown in FIG. 12, necessary 360° data corresponding to the above step (i) are collected on the target slice plane and thus, as described above, image reconstruction can be achieved via the steps (i)→(ii)→(iii).

On the contrary, in the helical scan shown in FIG. 13, since it is a helical scan, only one view can be collected on the target slice plane.

Therefore, after necessary data have been obtained by virtue of interpolation of raw data, which are obtained by correcting projection data being acquired, along the Z-axis direction in place of the step (i), image reconstruction must be effected by a filter correction back projection method for the above (ii)→(iii).

In the case of the single slice CT, two representative interpolation methods in the helical scam system are a 360° interpolation method and a complementary beam interpolation method.

First, the 360° interpolation method will be explained with reference to the scan diagram in FIG. 14.

As shown in FIG. 14, the 360° interpolation method is such a method that two direct data of two views, to which are positioned opposite mutually sandwiching the target slice position so as to make a closest pair and which have a same phase (projection angle), can be linearly interpolated to be in reciprocal proportion to the distance between the slice plane and each sampling position.

For instance, if the target slice position (Z-coordinate of the slice plane) is set to Z=Z0, data acquired at the slice position are only one view at the phase 0°. Hence, for example, in order to obtain data at the phase θ, upper direct data 1 and lower direct data 2 of the slice position are selected and then respective direct data are linearly interpolated every channel to be in reciprocal proportion to the distance (Z-coordinate) between each sampling Z-coordinate and the target slice position Z0, so that interpolation data can be obtained. This process is repeated to necessary phases.

Data in the j-th view in the 360° interpolation method are shown in FIG. 19.

The 1, 2, 3, . . . , Nch data in the direct data 1 and the 1, 2, 3, . . . , Nch data in the direct data 2 are respectively interpolated to be in reciprocal proportion to the distance between the sampling position of the direct data 1/the direct data 2 and the target slice position, whereby interpolation data can be obtained.

Second, the complementary beam interpolation method will be explained.

The complementary beam interpolation method is such a method that interpolation is executed by using complementary data which is virtual data.

As shown in FIG. 16, the beams of acquired direct data which are directed to respective detecting elements, are indicated by solid line arrows, when the focus is positioned at a "black round mark" position. At this time, the left side beam 1 and the beam indicated by a dotted line acquired when the X-ray focus is positioned at a "white round mark" position pass through the same path. The beam from the "white round mark" is called complementary beam.

Similarly, the beam 2 and the beam indicated by a dotted line from a light gray mark (roughly dotted mark) are complementary beams to pass through the same path, and also the beam 3 and the beam indicated by a dotted line from a dark gray mark (finely dotted mark) are complementary beams to pass through the same path. In this manner, all beams from the "black round mark" have complementary beams.

Therefore, a method wherein virtual data (called the complementary data) can be formed by extracting the complementary beam corresponding to respective beams from data acquired at respective focus positions, i.e., white round mark-→light gray mark (roughly dotted mark)-→dark gray mark (finely dotted mark) and then linear interpolation is performed by use of the direct data and the complementary data is the complementary beam interpolation method.

At this time, the complementary beams can be given by following equations.

$$y = CentCH \times 2 - k$$

$$x = \{[(k\text{-}CentCH) \times \phi]/[Nch \times 180] + 1/2\} \times Nview \quad \text{[Equation 3]}$$

Where $\phi$:Nch=$\psi$:(k-CentCH) and (180+2 $\psi$):x=360: Nview (see FIG. 9)

Nview=view number per one time,

Nch=channel number, $\phi$=fan angle, $\psi$=angle relative to channel,

CentCH=center channel=(Nch+0.5)/2 (In the case of QQ offset fitting).

Accordingly, the virtual complementary data which is shifted by about half turn in the slice direction and passes through the same path as the k-th channel can be obtained from data of the y-th channel in the j+x-th view.

A difference from the above QQ reconstruction resides in that data of the virtual channel having the path sandwiched by channels of the direct data can be derived in the QQ (see FIG. 8) whereas data having the same path as channels of the direct data can be derived at this time (see FIG. 20).

In other words, an object of the complementary beam in the complementary beam interpolation of the helical scan in the prior art is to obtain the beam having the same path as the direct data.

However, for example, in the case of Nview=1000, Nch=1000, j=100, k=700, $\phi$=50° in the above equations, y=300.5 channel and x=555.4861 can be obtained, which yields such data of the 300.5-th channel in the 655.4861-th view.

Hence, complementary data T.Data can be derived by four-point interpolating data D (655, 300) of the 300-th channel and data D (655, 301) of the 301-th channel in the 655-th view and data D (656, 300) of the 300-th channel and data D (656, 301) of the 301-th channel in the 656-th view based on integer portions Ix=int(x)=655 and Iy=int(y)=300 according the following equations. Respective complementary beams can be obtained by virtue of four point interpolation of two channels×two views.

$$T.Data = (1-w) \times [D(Ix, Iy) + D(Ix, Iy+1)]/2 + w \times [D(Ix+1, Iy) + D(Ix+1, Iy+1)]/2 \quad \text{[Equation 4]}$$

Ix=int(x), w=x-Ix, Iy=int(y), D(j, k): data of the k-th channel in the j-th view FIG. 18 is a conceptual view showing the complementary beam interpolation method applied to the j-th view data.

The 1, 2, 3, . . . , Nch direct data and the 1, 2, 3, . . . , Nch complementary data obtained by the above four-point interpolation are respectively interpolated by use of the direct data and the complementary data to be in reciprocal proportion to distances between the direct data/the complementary data and the target slice position, whereby interpolation data can be obtained.

Respective beams of the complementary data can be obtained from data in the different views as stated above. However, since the scan system is the helical scan, the slice position is shifted view after view. As a consequence, as shown in FIG. 18, the slice position of the complementary beam is shifted channel after channel.

Interpolation is executed by using respective data collected at the slice positions shifted by one turn in the 360° interpolation method, whereas shift of the slice positions of the direct data and the complementary data is about half turn in the complementary beam interpolation method. Hence, the complementary beam interpolation method is superior in resolution along the slice direction to the 360° interpolation method.

However, spatial resolution on the trans-axial plane is about 0.50 mm, which similar to that in the conventional scan system, in the 360° interpolation method, whereas spatial resolution on the trans-axial plane is less than 0.50 mm in the complementary beam interpolation method since the complementary data can be obtained by virtue of four-point interpolation.

(2) Multi-slice X-ray CT

Next, scan and image reconstruction in a multi-slice CT will be explained hereunder.

In recent years, according to the request to take the tomograms of the subject with high precision at high speed over the broad range, as shown in FIGS. 21A, 21B, 21C respectively, the multi-slice CT which has plural detector columns such as two, four, eight columns has been proposed.

First, while taking a four-column multi-slice CT shown in FIG. 21B as an example, several terms will be explained.

FIG. 6A shows the geometry viewed from the Z-axis direction, and a circle in FIG. 6A shows an effective field-of-view FOV.

FIG. 6B shows a plane including the Z-axis, which is viewed from the direction perpendicular to the Z-axis. A thickness of the beam along the Z-axis direction (a distance FCD from the X-ray focus) is set as a basic slice thickness T when the X-ray incident from the X-ray focus to the detecting element passes through the center of rotation.

The helical scan system in the multi-slice CT has been set forth in following literatures 1 and 2.

Patent Application Publication (KOKAI) Hei 4-224736; "CT Apparatus" H. Aradate, K. Nanbu (filed on Dec. 25, 1990) . . . (Literature 1)

Where it is assumed that a helical pitch P in the multi-slice CT is set similarly to a product of the detector column number N and the basic slice thickness T, i.e., a total slice thickness at the center of rotation by expanding a conception of a basic pitch in the above single slice CT, as shown in Eq.(1) in the following.

$$P = N \times T \quad (1)$$

The helical pitch will be expressed by a value obtained by dividing the helical pitch by the basic slice thickness hereinbelow. The helical scan at the pitch 4 is expressed by Eq.(1).

One of the interpolation methods, which have been proposed in the above literature 1 and in which the subject is helically scanned at the pitch N by the N column multi-slice CT, is an expanded 360° interpolation method in the single slice CT.

FIG. 22 is a scan diagram showing the above 360° interpolation method in the four column multi-slice CT. Like the 360° interpolation method in FIG. 14, interpolation is effected by use of two direct data which put the target slice position between them. This is temporarily called a "contiguous interpolation method", which has been set forth in the above literature 1.

In addition, in a following literature 2, three type methods for data processing in the helical scan system have been set forth.

Patent Application No. Hei 8-341739; "X-ray CT Apparatus", K. Taguchi, H. Aradate (filed on Dec. 20, 1996) . . . (Literature 2)

First, a high density sampling scan method (four columns are at Pitch=2.5, 3.5, 4.5 and two columns are at Pitch=1.5) has been disclosed.

In this method, the helical pitch has been set forth and also a method of improving the sampling density in the helical scan having the Pitch=2.5, 3.5, 4.5, etc. has been set forth.

Second, a new complementary beam interpolation method (interpolation method between the complementary beams) has been disclosed.

In other words, a method of utilizing the complementary beams has been recited. In this method, several combinations of an interpolation method using combinations of direct data/direct data and complementary data/complementary data and either the normal helical pitch or the helical pitch according to the high density sampling method have been set forth.

Third, a filter interpolation method has been disclosed.

In other words, as for the method of executing the filter interpolation process along the slice direction, four methods, i.e., a filter interpolation method 1 (filter interpolation method by using the sampling data filter process), a filter interpolation method 2 (filter interpolation method by using interpolation data/weighted addition (filter) process), a filter interpolation method 3 (filter interpolation method by using virtual scan raw data process), and a filter interpolation method 4 (filter interpolation method by using reconstruction voxel data process) have been set forth. In this method, combinations of the filter interpolation method and the normal helical pitch or the helical pitch at the high density sampling method, and further combinations of these and the new complementary beam interpolation method have been set forth.

However, there have been following problems in the prior art. More particularly, in the QQ in the above conventional scan system, the resolution of 0.35 mm can be derived on the trans-axial plane, but continuity along the slice direction is not good because of the conventional scan, so that the QQ method in the conventional scan system is not suitable for obtaining three dimensional volume data.

On the contrary, the interpolated image reconstruction in the helical scan system has good continuity along the body axis direction and is also suitable for obtaining three dimensional volume data. Especially the complementary beam interpolation method can obtain high spatial resolution along the body axis direction, but it has the spatial resolution on the trans-axial plane of less than 0.50 mm.

SUMMARY OF THE INVENTION

The present invention has been made to overcome the above problems, and it is an object of the present invention to provide an X-ray CT apparatus capable of satisfying both high spatial resolution (e.g., 0.35 mm) on an trans-axial plane and good continuity along a body axis direction in a helical scan.

In order to achieve the above object, as shown in FIG. 23, according to an aspect of the present invention, an X-ray CT apparatus comprises an X-ray beam generating source 21, detecting means 23 having one or plural detector columns along a slice direction of a subject, for detecting an X-ray generated from the X-ray beam generating source, moving means 15 for moving a patient couch or a rotating gantry, on which the subject is laid down, along a body axis direction of the subject, data acquisition means 27 for acquiring data via the detecting means, and data processing means 30 for processing data acquired by the data acquisition means to execute image reconstruction based on data which has been subjected to data processing.

Then, the X-ray beam is generated while rotating the X-ray beam generating source 21 and at the same time the patient couch or the rotating gantry is moved by the moving means 15 such that the subject can be scanned in a helical manner to acquire data via the detecting means 23 and to thus execute image reconstruction.

At this time, the data processing means 30 generates higher density data than sampling data acquired by the detecting means and then executes image reconstruction based on the high density data.

The high density data generated in this manner has two types, one is the data which have a sampling pitch finer than that of the acquired data (fine pitch data) and the other is data which have a sampling number larger than that of the acquired data (large point number data).

In either case, image reconstruction is executed based on the high density data. In this manner, both the high spatial resolution (e.g., 0.35 mm) of the trans-axial plane like QQ and the good continuity along the body axis direction in the helical scan can be satisfied.

As configuration of the present invention to generate such high density data, for example, there are various configurations described in the following.

More particularly, first, as shown in FIG. 24, in the X-ray CT apparatus, the data processing means 30 (in FIG. 23) includes first processed data generating means 29C for generating first processed data by processing a first group of data acquired via the detecting means 23, second processed data generating means 29E for generating second processed data by processing a second group of data acquired via the detecting means 23, and third processed data generating means 29H for generating third processed data, based on the first processed data generated by the first processed data generating means and the second processed data generated by the second processed data generating means.

With such configuration, in any of the single slice CT and the multi-slice CT, as shown in FIGS. 24 and 25, the first data group (e.g., direct data 1 and direct data 2) are acquired via the detecting means while executing the helical scan and the first processed data can be generated from these direct data by the first processed data generating means (e.g., interpolation means 1 (29C)). Similarly, the second data group (e.g., complementary data 1 and complementary data 2) are acquired via the detecting means and the second processed data can be generated from these complementary data by the second processed data generating means (e.g., interpolation means 2 (29F)), like the QQ. The third processed data generating means (e.g., high density data generating means 29H) can generate the high density data having the increased sampling point number by processing the first processed data and the second processed data, for example, via such process to place the first processed data and the second processed data alternately.

As such interpolation process, filter interpolation process executed by the configuration shown in FIG. 37 may be employed in addition to the above two point interpolation.

Second, as shown in FIG. 53, in the X-ray CT equipment, the data processing means 30 (in FIG. 23) includes first processed data generating means 29Q for generating first processed data group as high density direct data by executing channel direction interpolation process of a first group of data acquired via the detecting means 23, second processed data generating means 29P for generating second processed data group as high density complementary data from the first data group, and third processed data generating means 29R for generating third processed data at the target slice position, based on the first processed data group and the second processed data group.

With such configuration, as shown in FIG. 55, the high density direct data as the first interpolation data and the high density complementary data as the second interpolation data can be generated, and then the high density data at the target slice position can be generated by executing complementary beam interpolation process (i.e., helical interpolation process) based on the first interpolation data and the second interpolation data.

These and other objects, features, advantages, etc. of the present invention can made clear in connection with following embodiments and corresponding drawings.

BRIEF DESCRIPTION OF THE DRAWINGS

FIG. 21 is a conceptual view of a multi-slice CT;

DETAILED DESCRIPTION OF THE PREFERRED EMBODIMENTS (I) First Embodiment

Figure 23:
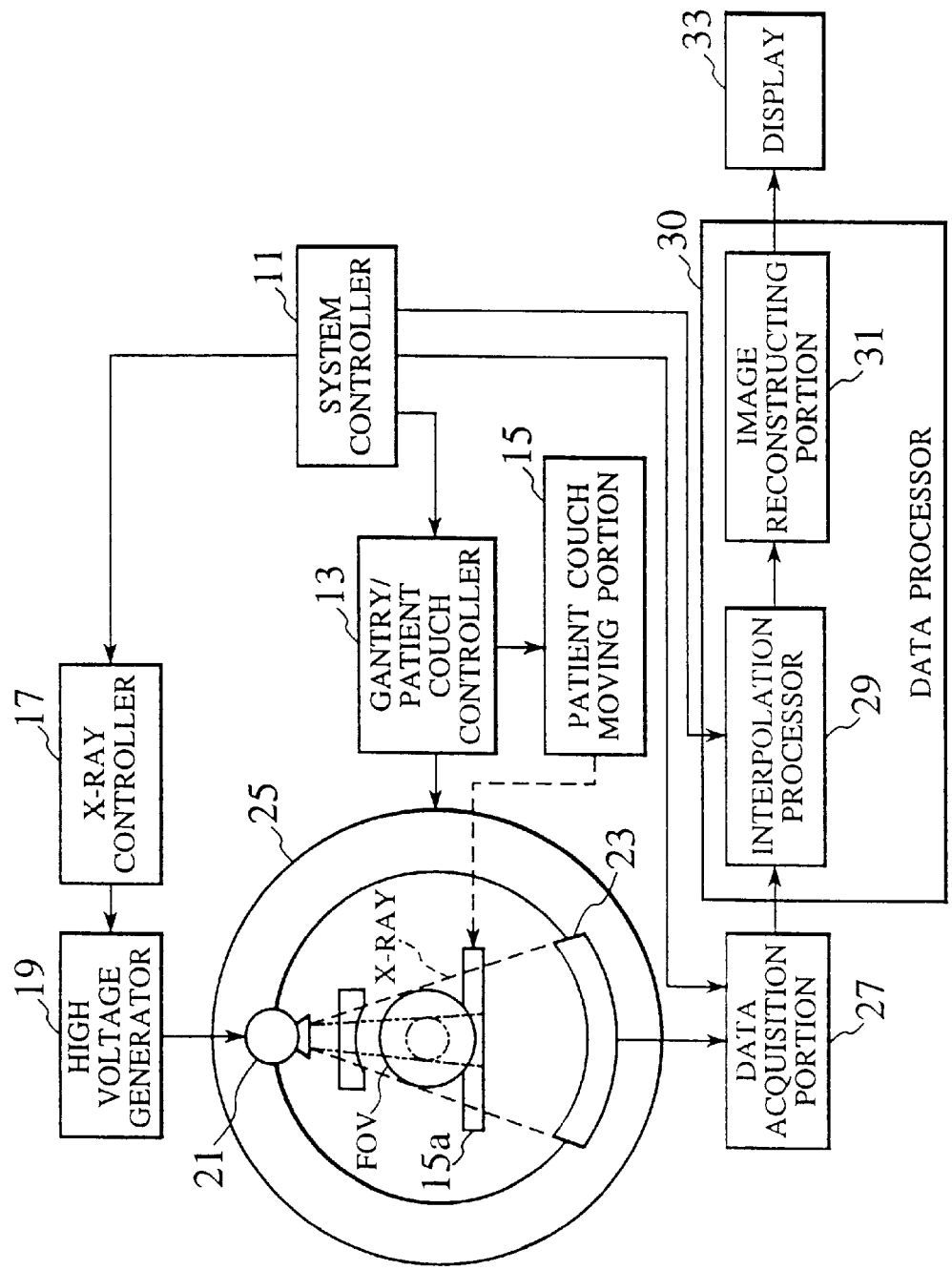
FIG. 23 is a view showing a system configuration of an X-ray CT apparatus in the present invention.
Figure 24:
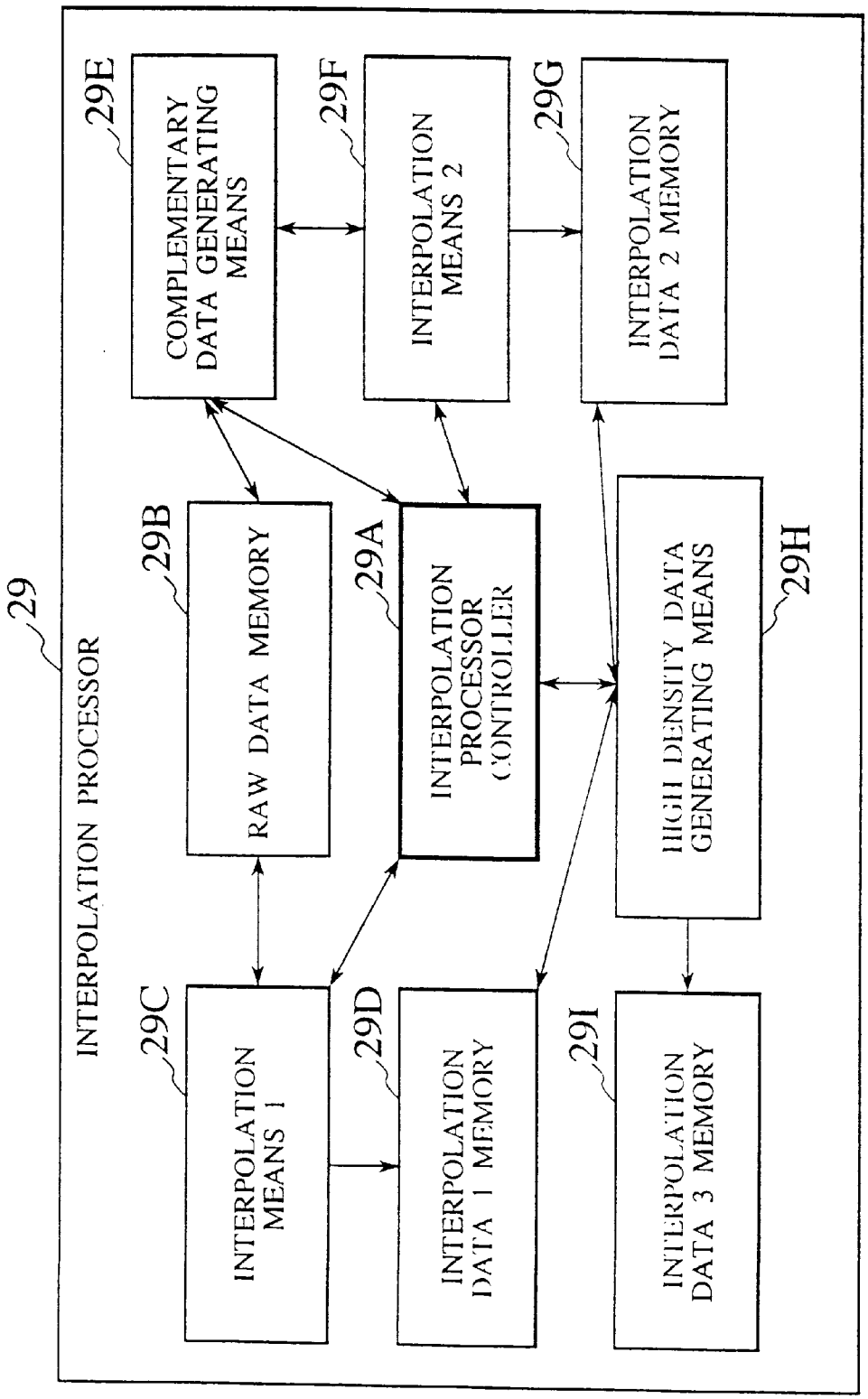
FIG. 24 is a functional block diagram of an interpolation processor in a first embodiment.
Figure 25:
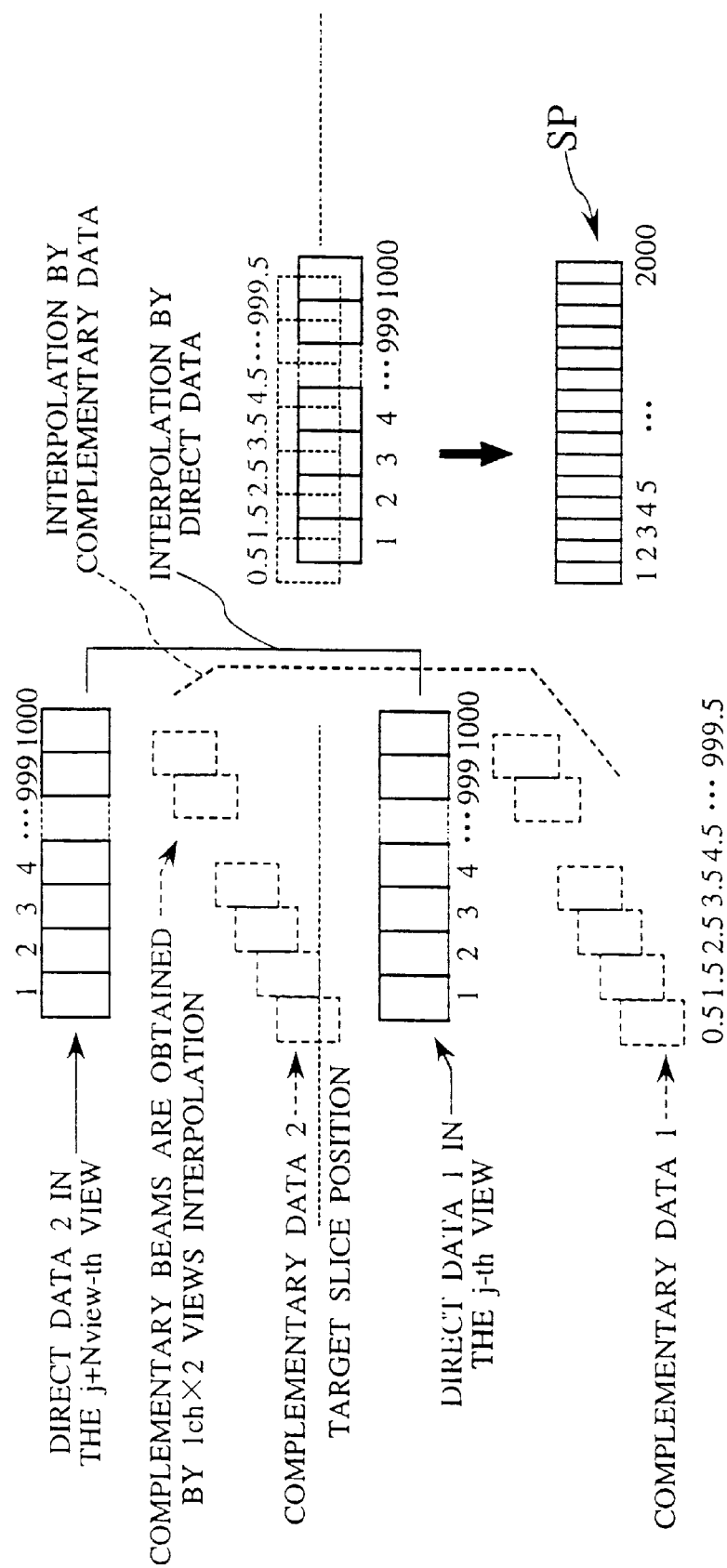
FIG. 25 is a conceptual view showing interpolation process in the first embodiment.
Figure 26:
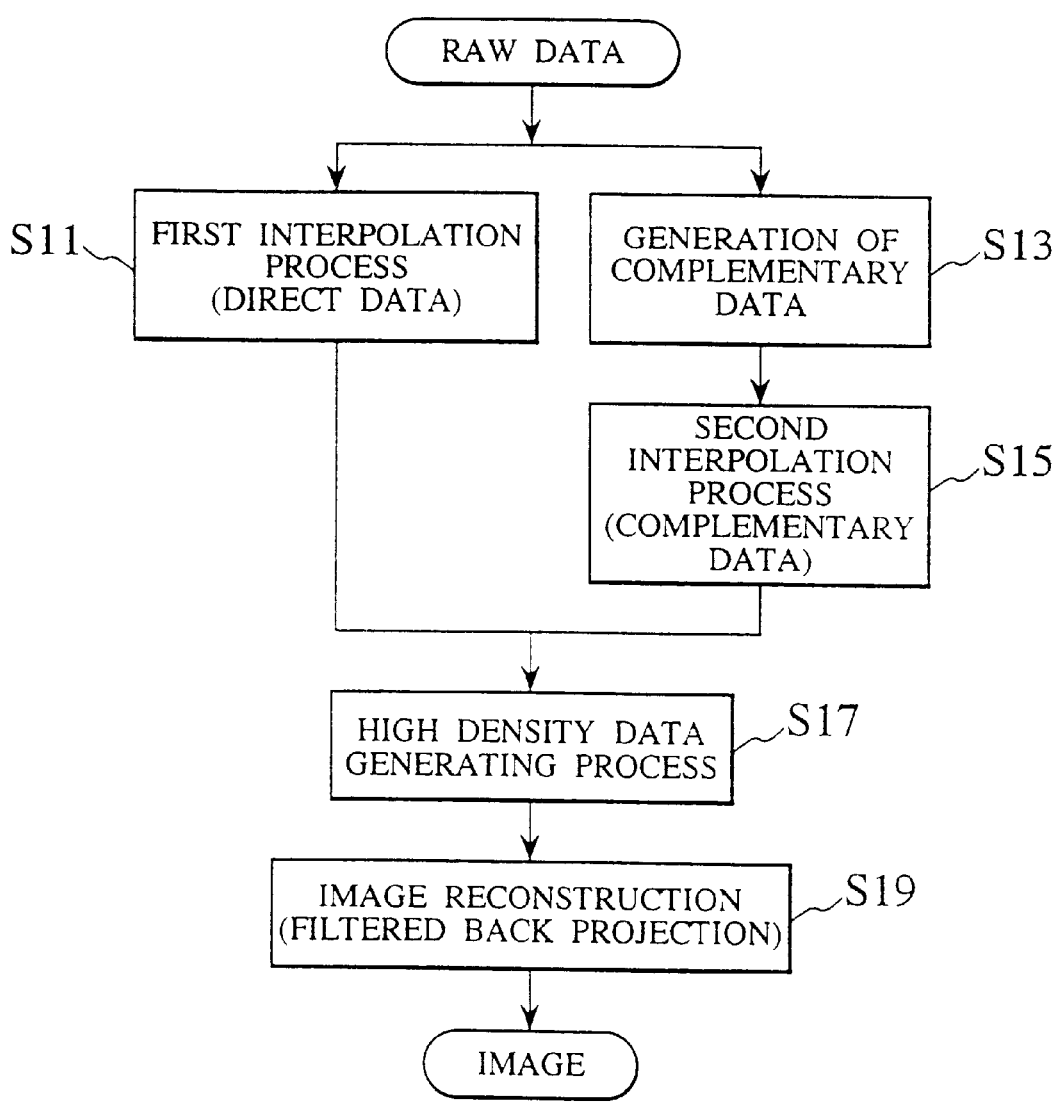
FIG. 26 is a flowchart showing flow of process in the first embodiment.

FIG. 23 is a view showing a system configuration of an X-ray CT apparatus in the present invention. FIG. 24 is a functional block diagram of an interpolation processor 29 in FIG. 23. FIG. 25 is a conceptual view showing interpolation process in the first embodiment. FIG. 26 is a flowchart showing flow of process in the first embodiment.

First of all, a configuration of the first embodiment will be explained.

As shown in FIG. 23, an X-ray CT apparatus comprises a system controller 11, a gantry/patient couch controller 13, a patient couch moving portion 15, an X-ray controller 17, a high voltage generator 19, an X-ray beam generating source 21, a detector 23, a rotating gantry 25, a data acquisition portion 27, an interpolation processor 29, an image reconstructing portion 31, and a display 33.

The system controller 11 outputs a rotational speed, a slice thickness, a fan angle, etc. of helical scan conditions, which are input from a not-shown input device, to the gantry/patient controller 13 as a gantry/patient couch control signal.

Also, the system controller 11 outputs an X-ray beam generation control signal for controlling X-ray beam generation to the X-ray controller 17, and also outputs a detection control signal indicating a timing for X-ray beam detection to the data acquisition portion 27.

In addition, the system controller 11 outputs a data acquisition control signal for data acquisition to the data acquisition portion 27 and also outputs an interpolation control signal indicating the interpolation method to the interpolation processor 29.

The gantry/patient couch controller 13 rotates a rotating gantry 25 based on the gantry/patient couch control signal output from the system controller 11 and outputs a patient couch moving signal to the patient couch moving portion 15.

The patient couch moving portion 15 calculates a moving amount of the patient couch 15a per one rotation of the rotating gantry 25 based on the patient couch moving signal output from the gantry/patient couch controller 13, and moves the patient couch 15a by this moving amount.

The X-ray controller 17 controls a timing of high voltage generation by the high voltage generator 19 based on the X-ray beam generation control signal output from the system controller 11.

The high voltage generator 19 supplies a high voltage to the X-ray beam generating source 21 in compliance with the control signal from the X-ray controller 17 for exposure of X-ray beams from the X-ray beam generating source 21.

The X-ray beam generating source 21 exposes the X-ray beam by the high voltage supplied from the high voltage generator 19.

The detector 23 is a single slice detector for acquisition projection data transmitted through the subject.

The rotating gantry 25 holds the X-ray beam generating source 21 and the detector 23. In addition, the rotating gantry 25 is rotated by a not shown gantry rotating mechanism around the axis of rotation which passes through an intermediate point between the X-ray beam generating source 21 and the detector 23.

The data acquisition portion 27 acquires the X-ray beam (actually, the detection signal) detected by the detector 23 in compliance with a data acquisition control signal output from the system controller 11.

The data processor 30 comprises the interpolation processor 29 and the image reconstructing portion 31.

The interpolation processor 29 interpolates the X-ray beam at the target slice position based on the X-ray beam acquired by the data acquisition portion 27. The interpolation processor 29 is made up of CPU, memory, etc. As described above, a detailed configuration of the interpolation processor 29 is shown in FIG. 24.

The image reconstructing portion 31 reconstructs the image based on the X-ray beam which is interpolated by the interpolation processor 29.

The display 33 displays the image reconstructed by the image reconstructing portion 31 on a not-shown monitor.

Next, an operation of the first embodiment which is classified into a schematic operation of CT and an interpolation process will be explained.

First of all, the schematic operation will be explained.

First, an operator inputs helical scan conditions via a not-shown input device. For instance, the helical scan conditions are set as follows.

| Detector column number | Nseg = 1 |
| Detector channel number | Nch = 1000 |

Detector thickness at center of rotation along Z-axis

| direction | Dseg = 2.0 mm |
| Beam thickness at center of rotation | Nseg × Dseg = 2.0 mm |
| Focus-Center-Distance | FCD = 600 mm |
| Focus-Detector-Distance | FDD = 1200 mm |
| Field-of-View | FOV = 500 mm |
| Field-of-view angle (fan angle) | φ = 50° |

When receives the above helical scan conditions, the system controller 11 outputs the rotational speed, the slice thickness, the fan angle, etc. out of the helical scan conditions as a gantry/patient couch control signal to the gantry/patient couch controller 13. Then, the gantry/patent couch controller 13 outputs the patient couch moving signal to the patient couch moving portion 15 based on the gantry/patient couch control signal.

When diagnosis start instruction is input by the operator via the input device under this state, the system controller 11 instructs the gantry/patient couch controller 13 to start the diagnosis and also outputs the X-ray beam generation control signal to the X-ray controller 17 to control the X-ray beam generation. In compliance with the X-ray beam generation control signal, the X-ray controller 17 causes the high voltage generator 19 to generate the high voltage.

As a result, the X-ray beam is exposed from the X-ray beam generating source 21 and simultaneously the patient couch 15a is moved by the patient couch moving portion 15, so that the diagnosis by virtue of the helical scan is started.

When the data acquisition control signal is output from the system controller 11, the data acquisition portion 27 detects the X-ray beam by the detector 23 in compliance with the data acquisition control signal and then supplies the X-ray beam (actually, detected data) to the interpolation processor 29.

When the X-ray beam is supplied, the interpolation processor 29 interpolates the X-ray beam at the target slice position based on this X-ray beam.

Second, the interpolation process will be explained.

FIG. 25 is a conceptual view showing interpolation process. FIG. 26 is a flowchart showing flow of the interpolation process.

Figure 14:
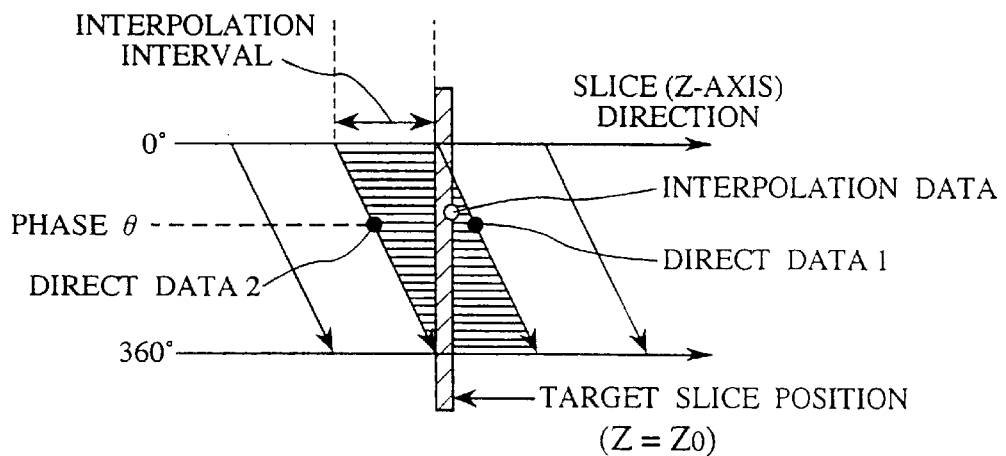
FIG. 14 is a scan diagram showing a 360° interpolation method.
Figure 15:
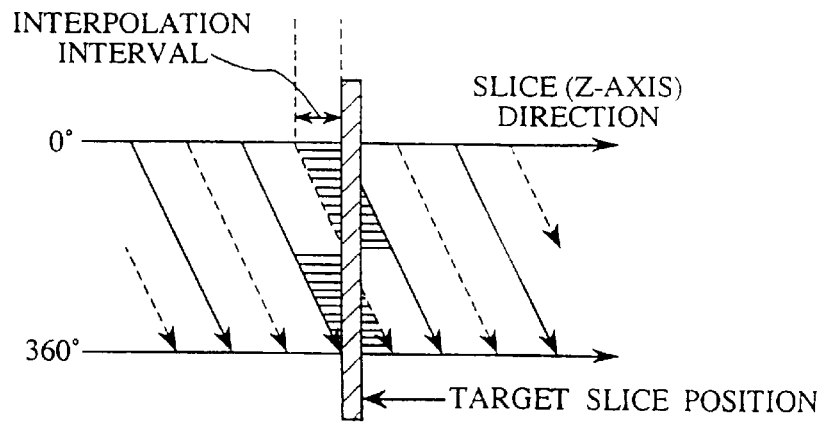
FIG. 15 is a scan diagram showing a complementary beam interpolation method.
Figure 16:
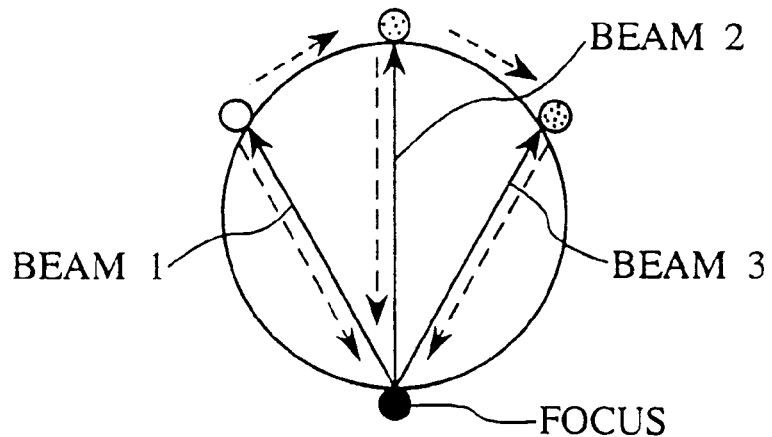
FIG. 16 is a view showing complementary beams.
Figure 17:
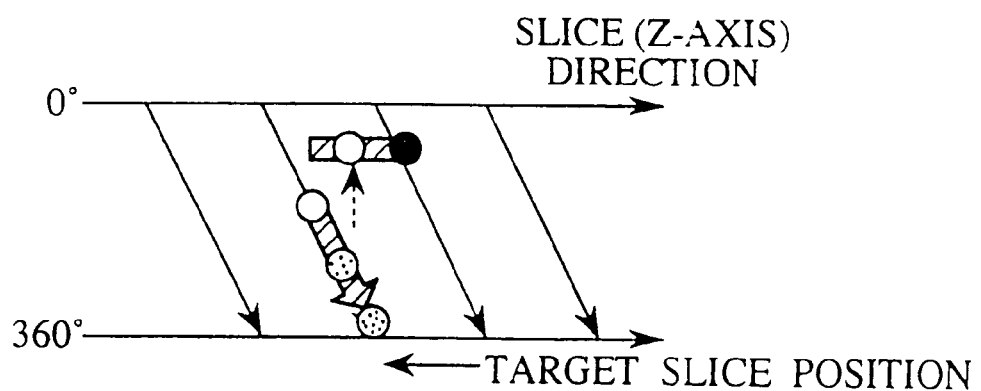
FIG. 17 is a view showing a sampling position of the complementary beam.
Figure 18:
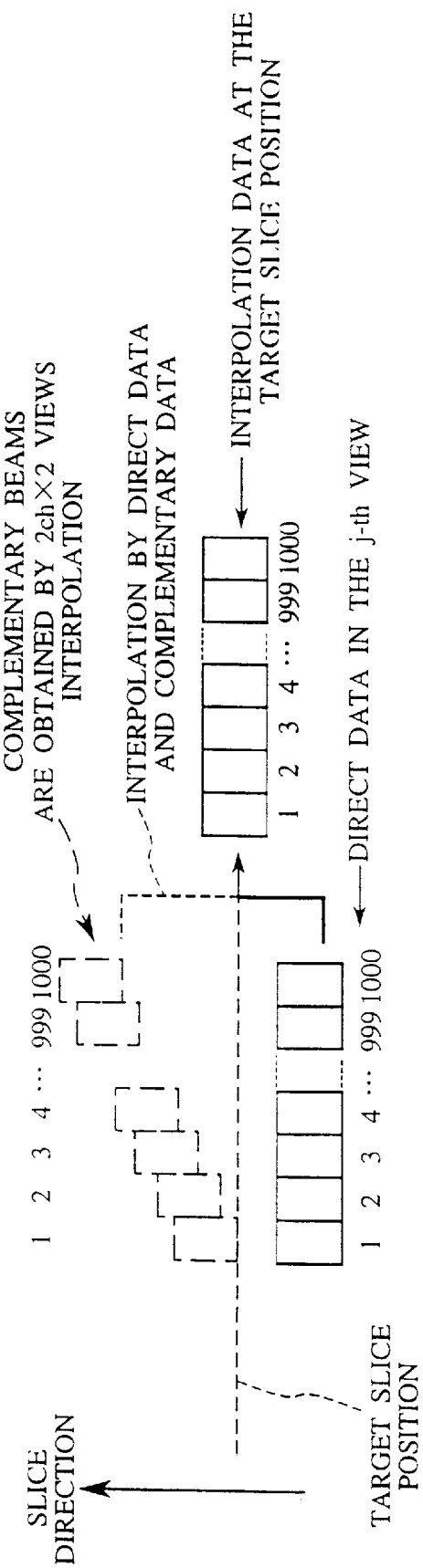
FIG. 18 is a conceptual view showing the complementary beam interpolation method applied to the j-th view data.
Figure 19:
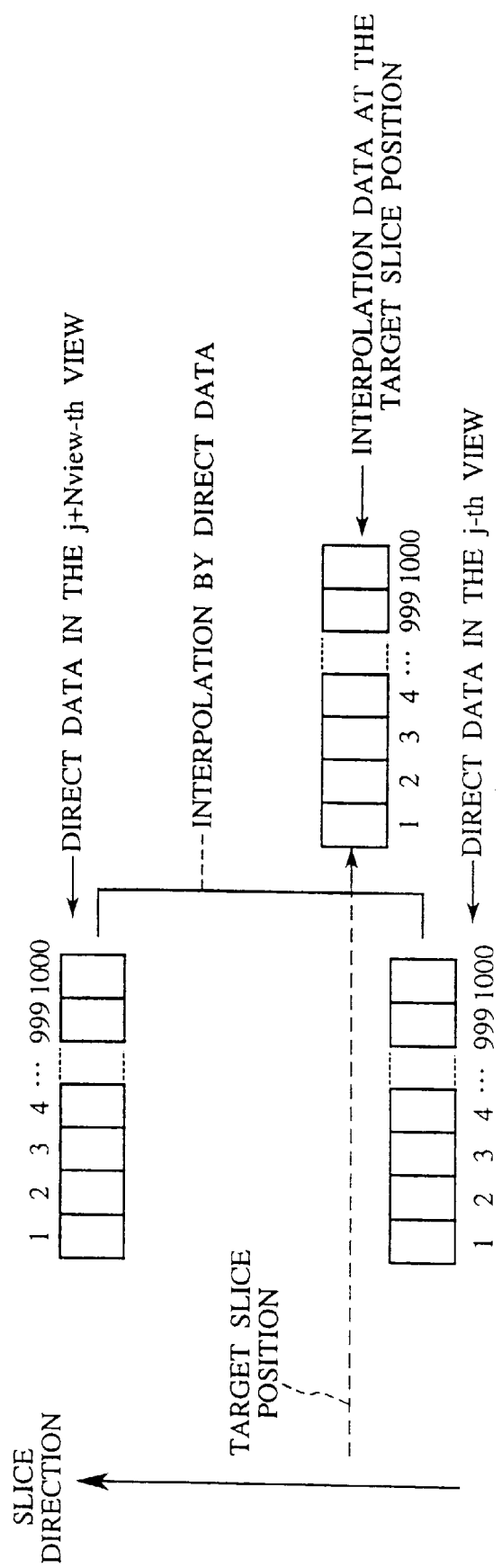
FIG. 19 is a conceptual view showing the 360° interpolation method.
Figure 20B:
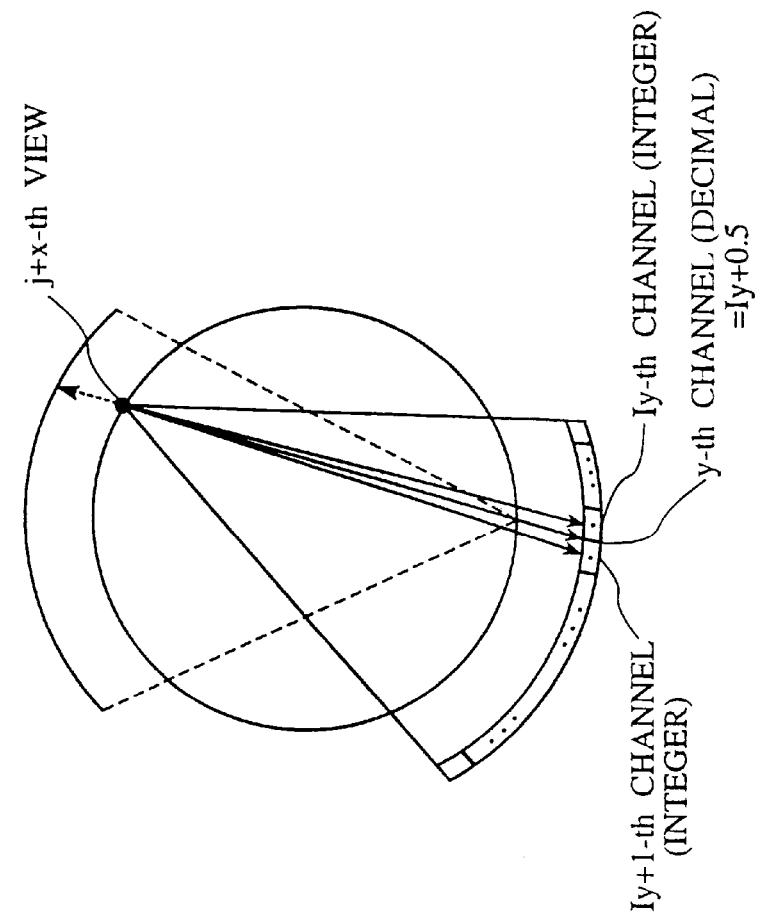
FIG. 20 is a view showing the complementary beams in the complementary beam interpolation in the helical scan.
Figure 20A:
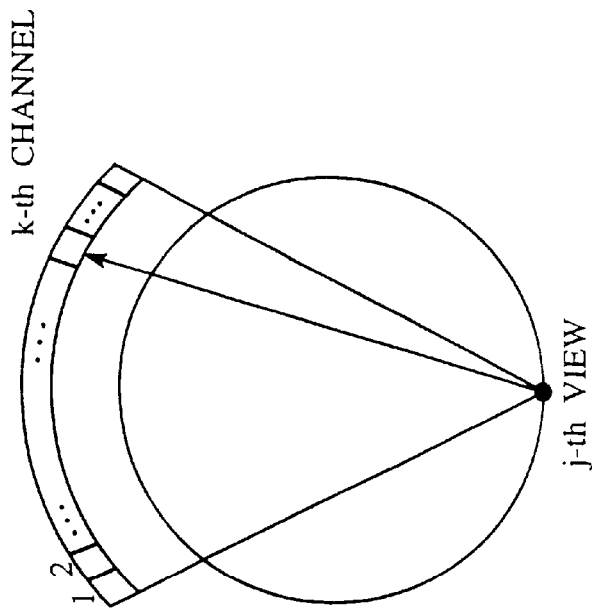
Figure 22:
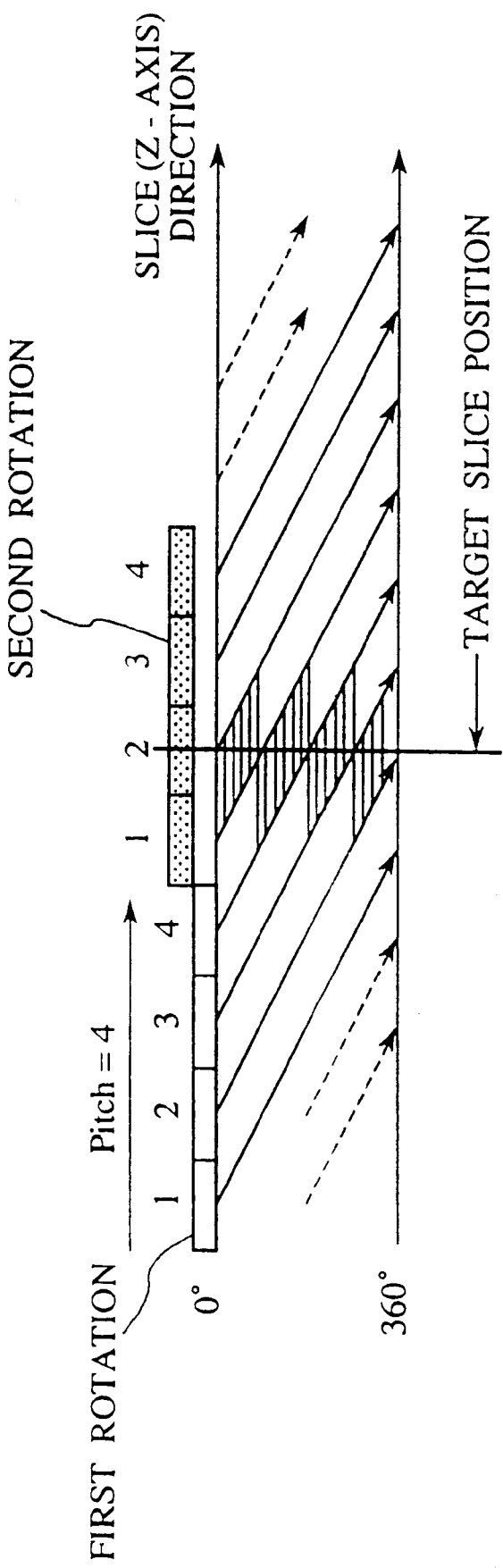
FIG. 22 is a scan diagram when the 360° interpolation method is applied to a four column multi-slice CT.

In FIG. 25, plural data at a certain phase θ are shown. Then, the j-th view as the lower direct data 1 of the slice position and the j+Nview-th view as the upper direct data 2 thereof will be considered. These data are the same as those used in the above 360° interpolation method (see FIG. 14 and FIG. 19).

In the first embodiment, the lower complementary data 1 and the upper complementary data 2 of the slice position will be further considered.

Figure 11:
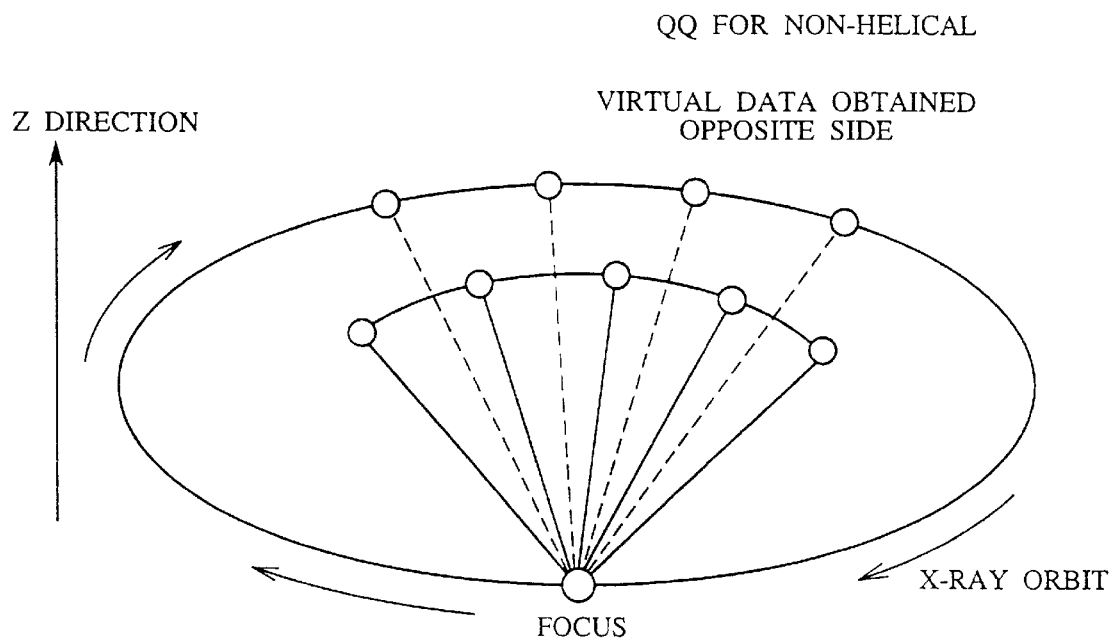
FIG. 11 is a conceptual view showing QQ.
Figure 12:
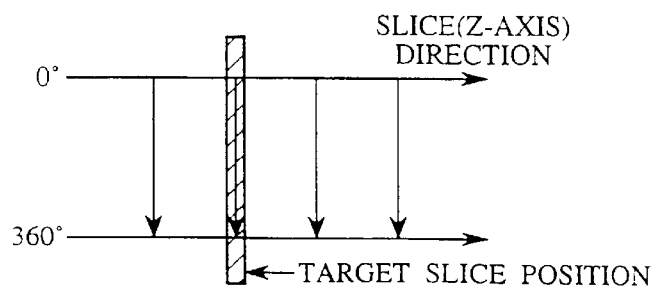
FIG. 12 is a scan diagram showing a scan system in the conventional scan.
Figure 13:
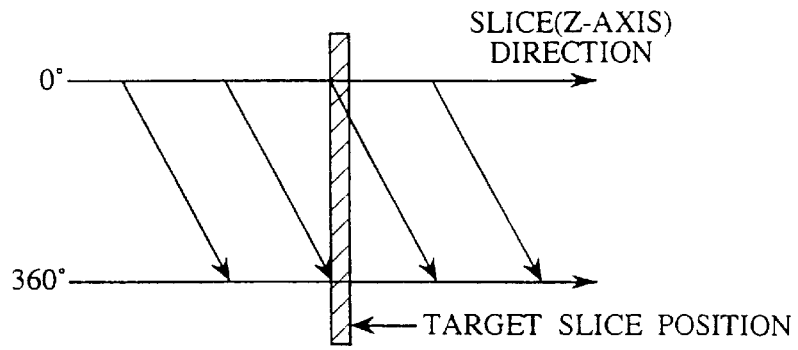
FIG. 13 is a scan diagram showing a scan system in the helical scan.

In comparison with FIG. 11 showing the QQ in the prior art, above conception will be explained with reference to FIG. 27.

Figure 27:
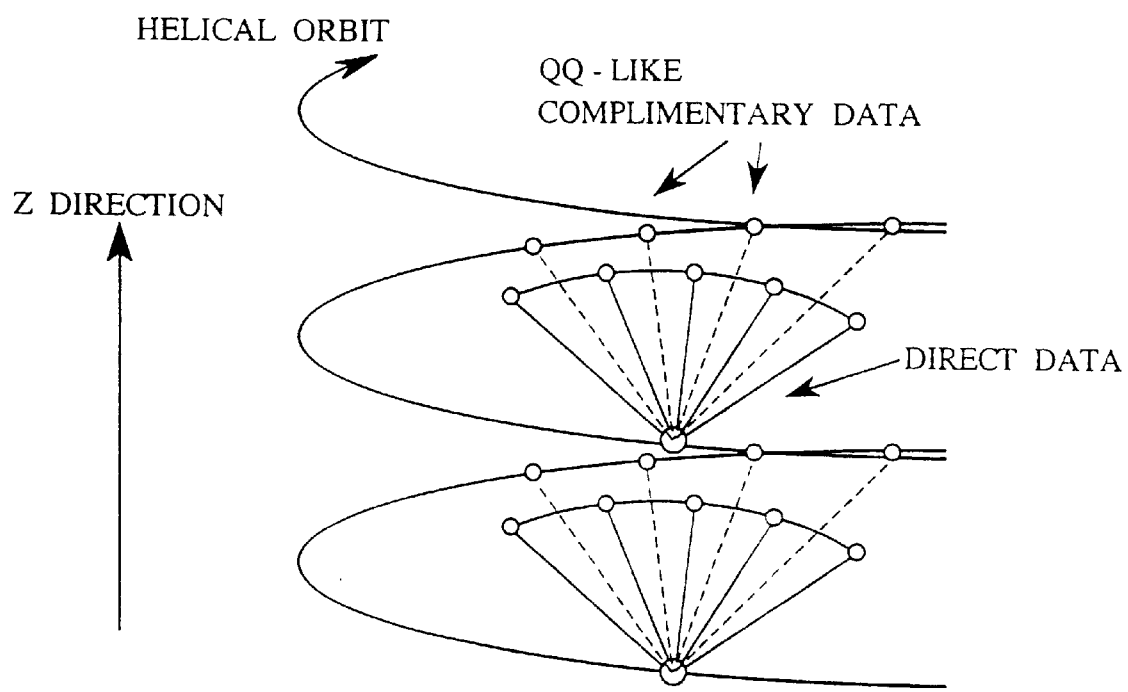
FIG. 27 is a conceptual view showing the interpolation process in the first embodiment.

FIG. 27 is a conceptual view showing process of the data in two rotation. First, the direct data are acquired at the focus position of the first rotation on this side. The focus is then turned to the opposite side, then QQ-like complementary data of the virtual channel are generated by use of the data acquired at the focus position which is sandwiched between channels of the direct data acquired above (in other words, nest position). Such process is repeated on the second rotation et seq. to thus generate a group of direct data and a group of complementary data. In addition, similar process will be repeated to data at different rotational phases (angle 0 to 360°

① First interpolation process

An interpolation means 1 (29C) receives the direct data 1 and the direct data 2 from a raw data memory 29B, then generates interpolation data 1 at the target slice position by executing linear interpolation to be in reciprocal proportion to a distance between the slice position of each direct data and the target slice position, and then stores the interpolation data 1 in an interpolation data 1 memory 29D (step S11 in FIG. 26). A weight of interpolation process is constant in all channels.

The interpolation data 1 are used as data on the first, second, third, . . . , 1000-th channels (also called as "integer channels" hereinafter).

② Complementary data generation

A complementary data generating means 29E reads necessary data from the raw data memory 29B, and then generates the complementary data of the virtual channels (the virtual channels are also called as "decimal channels" hereinafter) put between the channels of direct data by interpolating data of concerned one channel×two views in the same way as the QQ reconstruction set forth in the prior art (see FIG. 10). At this time, the lower complementary data 1 of the slice position and the upper complementary data 2 of the slice position are generated (step S13 in FIG. 26). The complementary data 1 and the complementary data 2 generated are data on the 0.5-th, 1.5-th, . . . , 999.5-th channels.

Since the complementary data 1 and the complementary data 2 generated are not interpolated along the slice direction, each complementary data in FIG. 25 is shown with shifting the slice position every channel.

③ Second interpolation process

An interpolation means 2 (29F) generates interpolation data 2 at the target slice position by linearly interpolating the complementary data 1 and the complementary data 2 to be in reciprocal proportion to a distance between the slice position of each data and the target slice position, and then stores the interpolation data 2 in an interpolation data 2 memory 29G (step S15 in FIG. 26). Weight of interpolation is calculated every channel.

The interpolation data 2 are used as data on the 0.5-th, 1.5-th, . . . , 999.5-th channels.

④ High density data generation process

A high density data generating means 29H reads interpolation data 1 (data on the integer channel) from an interpolation data 1 memory 29D and also reads interpolation data 2 (data on the decimal channel) from an interpolation data 2 memory 29G respectively, and then generates interpolation data 3 having twice sampling point number by placing respective data alternately (step S17 in FIG. 26). At this time, channel numbers ranging from 1 to 2000 (=2×Nch) are allocated newly to individual data constituting the interpolation data 3.

⑤ Filtered back projection

An image reconstruction portion 31 executes image reconstruction by virtue of the normal filtered back projection method, for example (step S19 in FIG. 26).

Since resultant images are reconstructed by using data having 2×Nch sampling point number, the spatial resolution on the trans-axial plane is about 0.35 mm, as in the QQ process. Besides, since data of the helical scan are used, continuity is excellent along the body axis direction. Both advantages are compatible.

An example has been explained in which the interpolation data 2 is generated by executing linear interpolation with the use of the lower complementary data 1 of the slice position and the upper complementary data 2 of the slice position in the first embodiment, but the present invention is not limited to such example.

Figure 28:
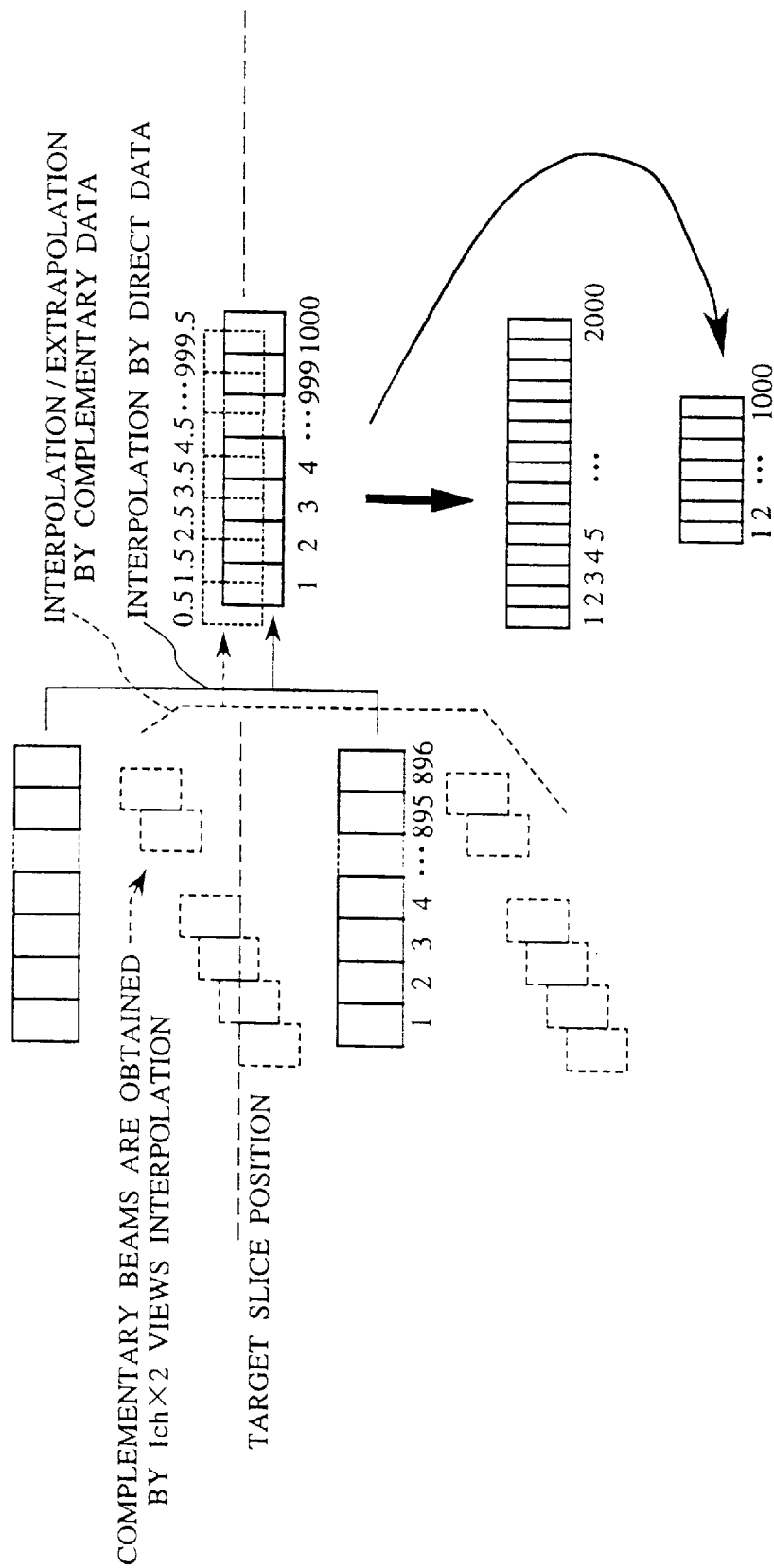
FIG. 28 is a conceptual view showing interpolation process if extrapolation is applied in the first embodiment.

For instance, nonlinear interpolation may be employed, or else extrapolation may be employed according to the channel, as shown in FIG. 28, by selecting the lower complementary data 1 of the slice position on the center channel and the upper complementary data 2 of the slice position on the center channel.

In addition, as indicated by a chain double-dashed line in FIG. 23, there is a case where the subject is small rather than a maximum FOV (e.g., a head portion). In such case, as shown in the right lower area in FIG. 28, the channel number may be reduced by half (in this case, 1000) to execute the interpolation process. In this manner, the image reconstruction can be executed in reduced-size memory and also high speed process can be implemented.

Figure 29:
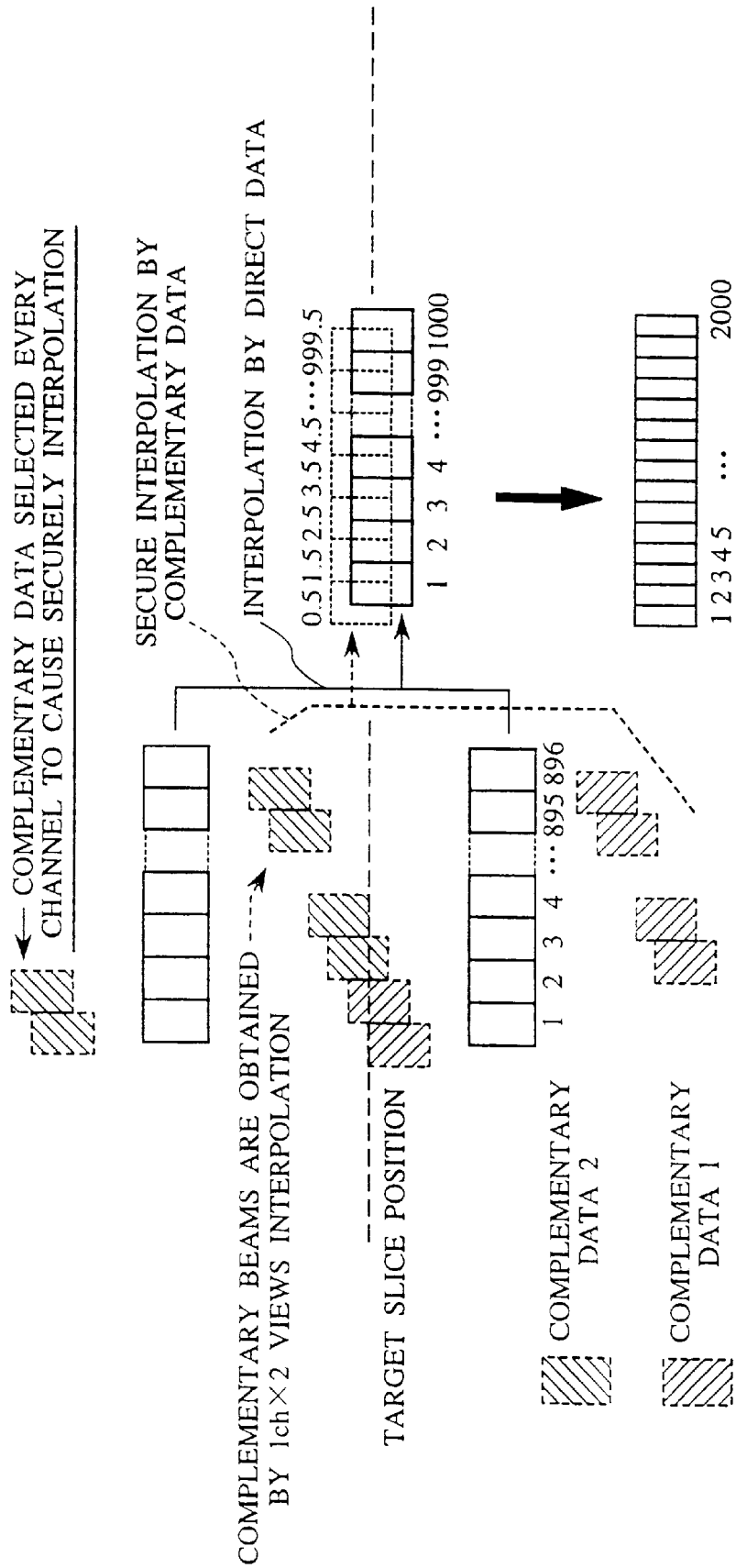
FIG. 29 is a conceptual view showing interpolation process if interpolation is applied in the first embodiment.

Otherwise, as shown in FIG. 29, selection of the complementary data every channel may be changed such that interpolation should be securely selected.

Figure 30:
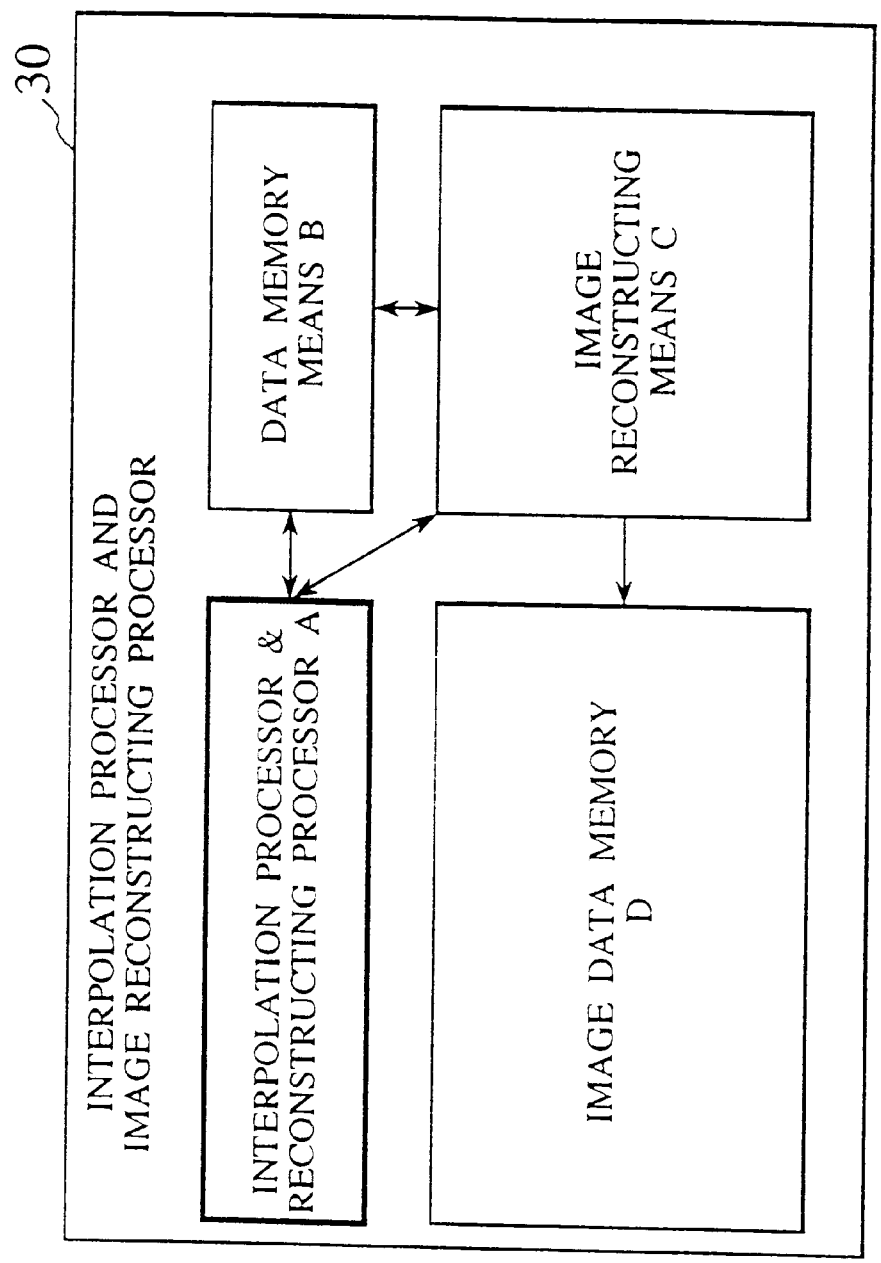
FIG. 30 is a block diagram showing a configuration if interpolation process is performed by a controller of an image reconstructing portion in the first embodiment.

In addition, although the interpolation processor and the image reconstructing portion are constructed separately in the first embodiment, the controller of the image reconstructing portion may be constructed to execute the interpolation process, as shown in FIG. 30.

(II) Second Embodiment

A second embodiment is a case of Debluring process along the channel direction. A system configuration of an apparatus in the second embodiment is identical with that in the first embodiment, and a detector for acquiring projection data of the subject is made of a single slice detector.

Figure 31:
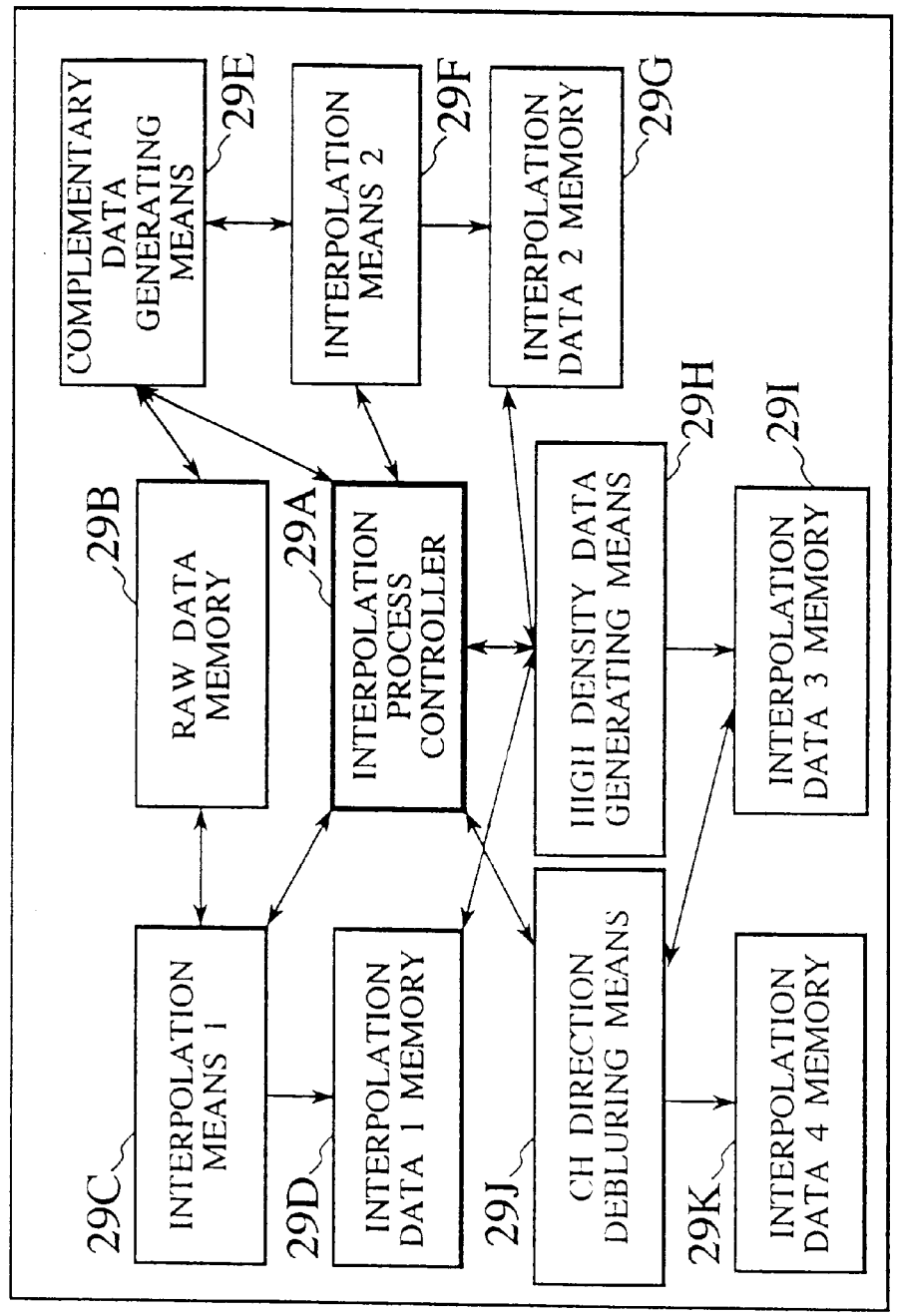
FIG. 31 is a functional block diagram of an interpolation processor in a second embodiment.

FIG. 31 shows a detailed configuration of an interpolation processor 29 in the second embodiment. In addition to the configuration of the interpolation processor 29 in the first embodiment, a channel direction Debluring means 29J and an interpolation data 4 memory 29K are provided.

Following processes ①  to ④ are the same as that in the first embodiment and therefore their explanation will be omitted.

① First interpolation process
② Complementary data generation
③ Second interpolation process
④ High density data generation process According to the above processes ① to ④, the complementary data 3 as high density data can be derived. Further, following process ⑤ is executed in the second embodiment.

⓪ Channel direction Debluring process

Figure 32:
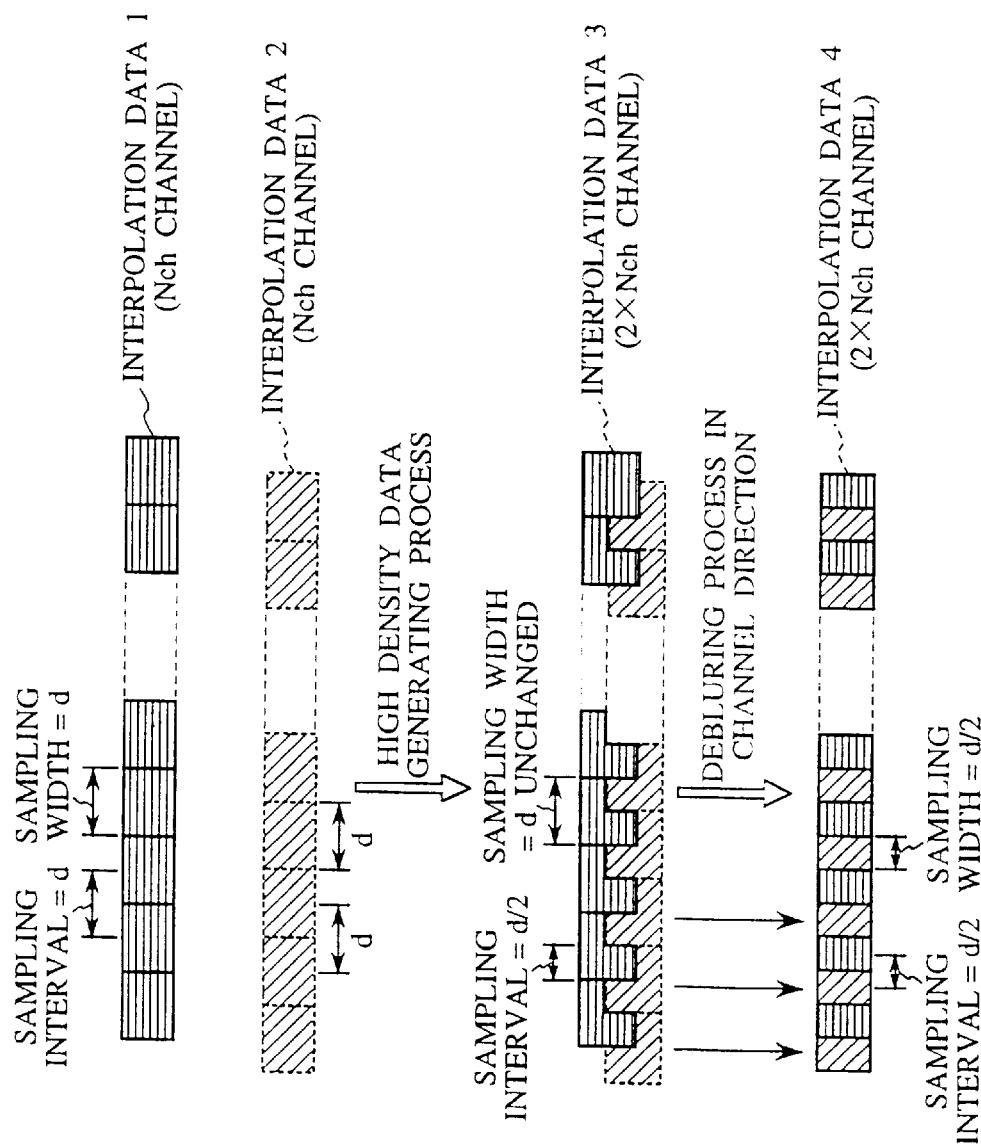
FIG. 32 is a conceptual view showing channel direction Debluring process.

FIG. 32 is a conceptual view showing channel direction Debluring process.

Sampling intervals and sampling widths of the interpolation data 1, the interpolation data 2, and the interpolation data 3 will be discussed. For the sake of simplicity, under the assumption that channels are arranged linearly and the X-ray beams are entered in parallel into respective detecting elements, explanation will be made hereunder.

In the interpolation data 1 and the interpolation data 2, a total sampling point number is Nch, the sampling interval is a channel interval d, and the sampling width between respective sampling points is d. On the contrary, in the interpolation data 3, a total sampling point number is 2Nch, and the sampling width between respective sampling points is d, but the sampling interval is d/2. In other words, it can be understood that, since these data are overlapped with each other, they include redundancy.

Therefore, in order to recover the redundancy due to such overlap, filter process is applied to the interpolation data 3 by an out-of-focus recover filter which has an enhance effect in the channel direction. This type of process which is called deconvolution process or Debluring process has been well known for one skilled in the art following to the QQ process, etc. Examples of the out-of-focus recover filter has been set forth in following literatures 3, 4, but the filter is not limited to such examples. Appropriately modified filter such as enhance filter, smoothing filter, etc., as shown in FIG. 41, may be employed.

Patent Application Publication (KOKAI) Sho 61-74071; "X-ray CT Apparatus", I. Horiba, A. Iwata, H. Sasaki, K. Satoh (filed on Sep. 19, 1984) . . . (Literature 3)

Patent Application Publication (KOKAI) Sho 61-290573; "X-ray CT Apparatus", H. Nishimura (filed on Jun. 19, 1984) . . . (Literature 4)

A channel direction Debluring means 29J reads the interpolation data 3, then executes convolution of the interpolation data 3 and the Debluring filter DF.CH to generate interpolation data 4, and then stores the interpolation data 4 into an interpolation data 4 memory 29K. The redundancy can be recovered in the interpolation data 4.

⑥ Filtered back projection

Next, the image reconstructing portion 31 reconstructs images by virtue of the normal filtered back projection method. Reconstructed images are such images having higher spatial resolution since they employ the interpolation data 4 in which redundancy can be recovered.

In the above explanation, the channel direction Debluring process and the convolution of the reconstruction filter in the filtered back projection method are executed separately with each other, but these processes may be executed simultaneously. Since the convolution process is linear process, as given in following equations, sequential convolutions of a filter F1 and a filter F2 against data D is mathematically equivalent to one convolution of a filter F3, to which convolutions of the filter F1 and the filter F2 are applied, against the data D.

$$\text{Data} = F2*(F1*D) = (F2*F1)*D = F3*D, \quad F3 = F2*F1 \quad \text{[Equation 5]}$$

Accordingly, if data are processed by virtue of a composite filter in which the filter used in the above Debluring process and the reconstruction filter in the filtered back projection method are convoluted previously, the convolution process becomes effective because it is needed only once.

In addition, the Debluring process against the interpolation data 3 has been explained in the above explanation. However, the interpolation data 2 also includes the out-of-focus due to interpolation because interpolation of the data of one channel×two views has been executed at the time of generating the complementary data. Therefore, the Debluring process for recovering the out-of-focus may be applied to the interpolation data 2 apart from the above Debluring process. Such Debluring process may be applied to the complementary data 1 and the complementary data 2, otherwise such Debluring process may be applied to the interpolation data 2 which has been obtained by interpolating the complementary data 1 and the complementary data 2.

(III) Third Embodiment

A third embodiment is a case of a multi-slice CT.

A system configuration of the apparatus in the third embodiment is the same as the first embodiment. However, such multi-slice CT is a multi-slice CT system having a four column multi-slice detector (see FIG. 21B).

A detailed configuration of the interpolation processor 29 in the third embodiment is identical with that of the first embodiment. In other words, its operation is different from that in the first embodiment but its configuration is identical with the first embodiment.

Figure 33A:
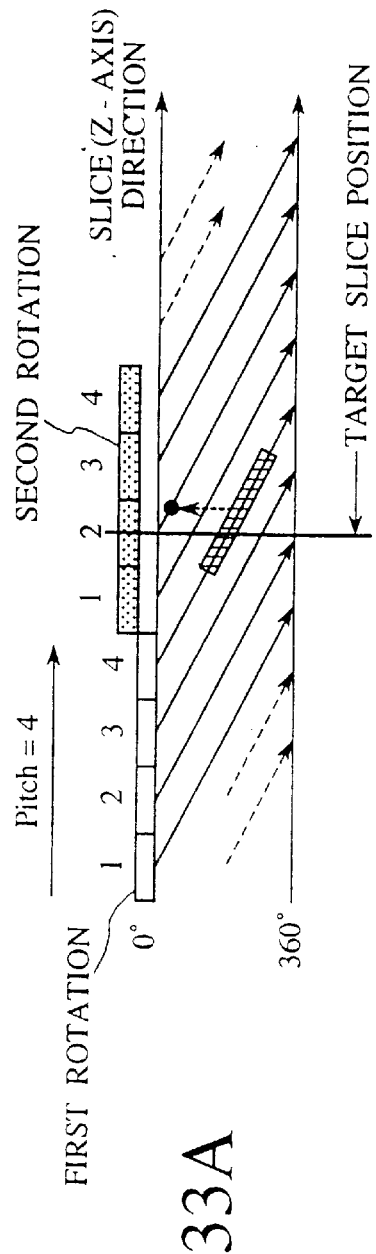
FIG. 33 is a scan diagram showing complementary beams in a certain column if the helical scan is performed at Pitch=4 in the four column multi-slice CT.
Figure 33B:
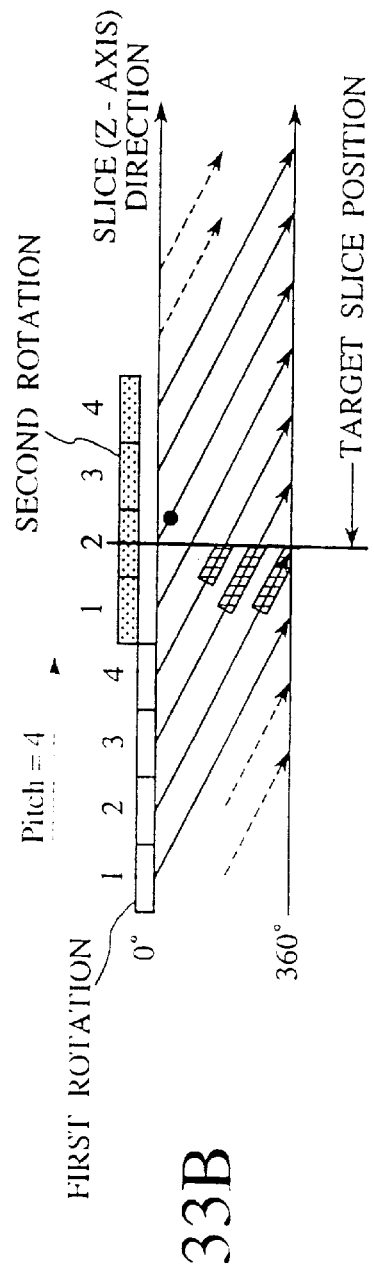
Figure 34:
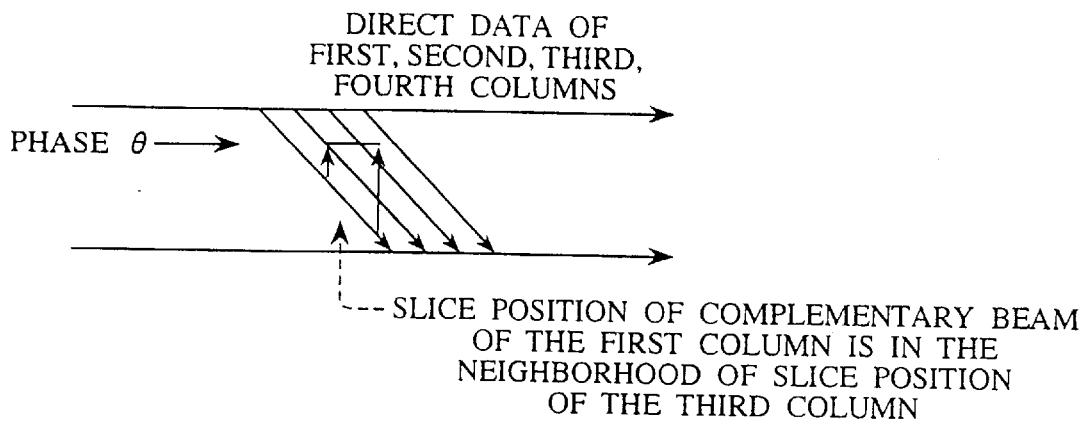
FIG. 34 is a scan diagram showing complementary beams in a certain column if the helical scan is performed at Pitch=4 in the four column multi-slice CT.

If the helical scan is executed at Pitch=4 by the four column multi-slice CT, the complementary data at a certain column become a series of data which substantially coincide with the sampling position of the direct data in different columns at the center channel (see the literature 2 concerning the details), as shown in FIGS. 33 and 34. Since the sampling position between the direct data and the complementary data is close, this event becomes a significant demerit upon interpolating by the direct data and the complementary data. The third embodiment would positively utilize this event.

Figure 35:
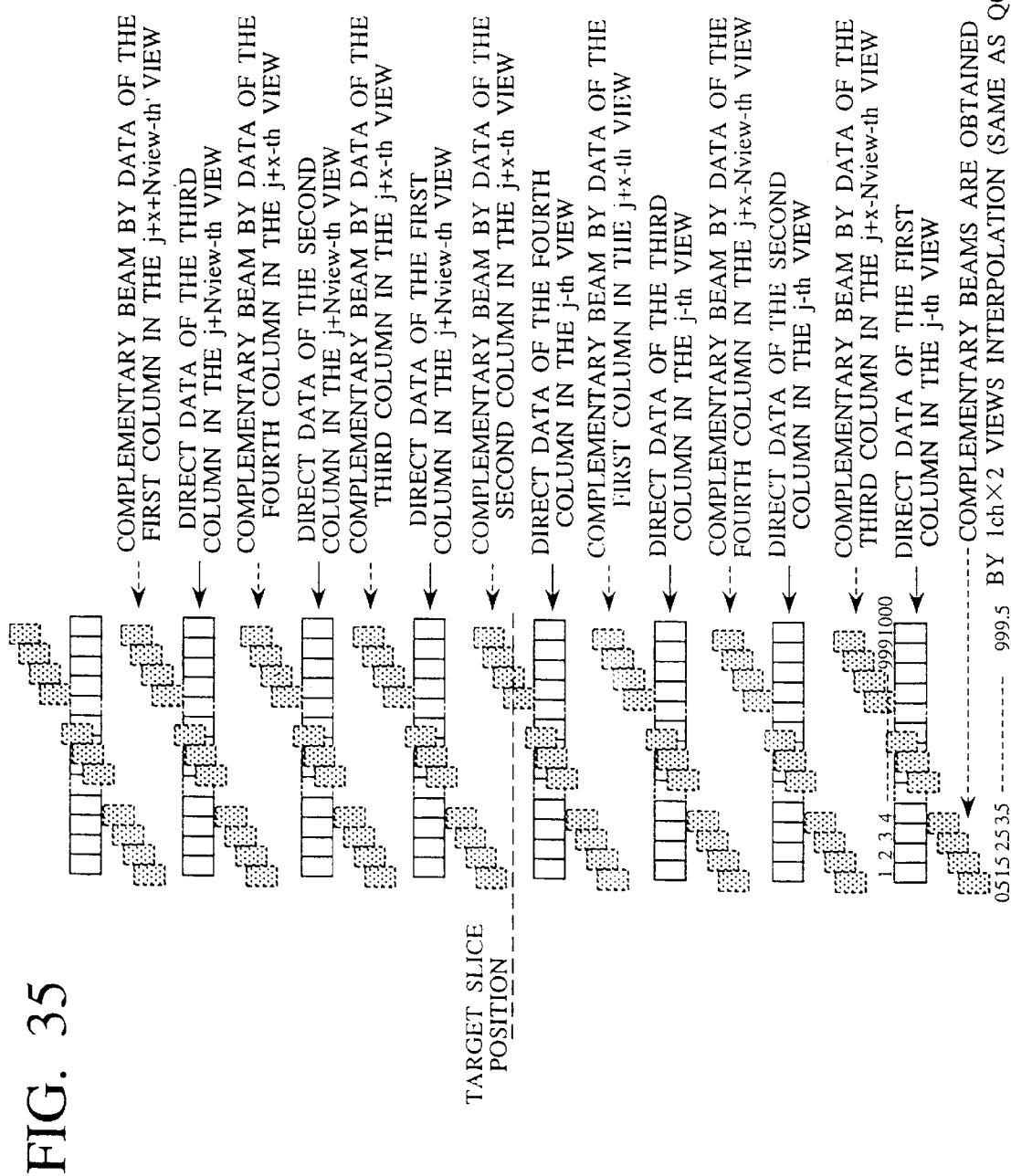
FIG. 35 is a view showing a state of phase $\theta$ acquired by the four column multi-slice CT.

A state of certain phase θ acquired by the four column multi-slice CT is shown in FIG. 35.

A total eight data, i.e., four column direct data in the j-th view, four column complementary data generated from the data in the j+x-th view like the first embodiment, four column direct data in the j+Nview-th view after one rotation (Nview), two complementary data generated from the first and second column data in the j+x+Nview- th view, and two complementary data generated from the third and fourth column in the j+x-Nview-th view before one rotation data are shown. Normally the number of data can be represented by the following equations, but only a part thereof is shown herein.

(Data number)=(rotation number of helical scan)×(detector column number)×2     [Equation 6]

Figure 36:
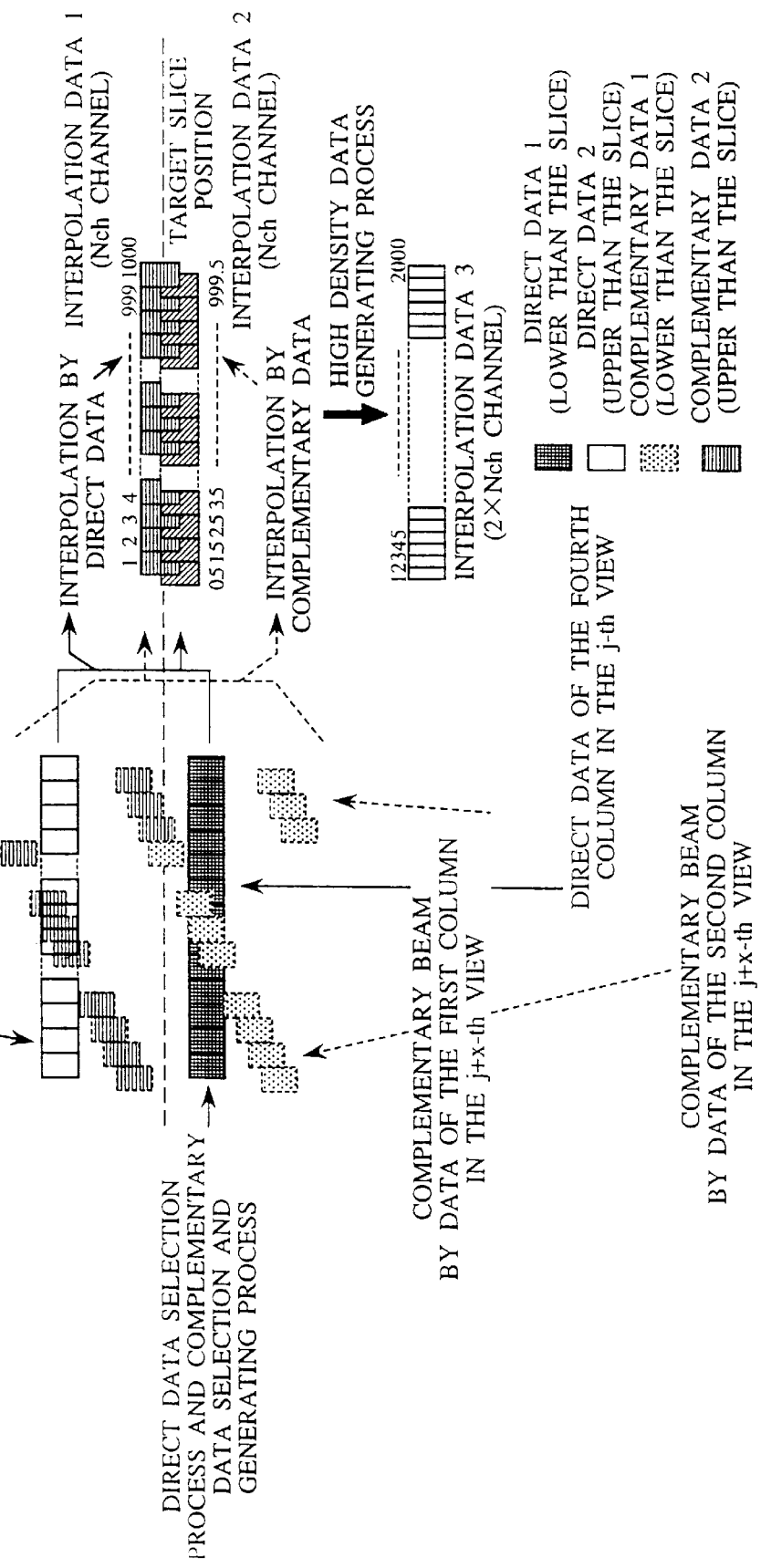
FIG. 36 is a conceptual view showing process in a third embodiment.

FIG. 36 is a conceptual view showing process in the third embodiment.

Explanation will be made in detail hereunder. But the processes ②④⑤⑥ are the same as those in the first embodiment and therefore their explanation will be omitted. A difference from the first embodiment is that functions as data selecting means are added to the interpolating means 29C and the complementary data generating means 29E.

① Selection of direct data 1 and direct data 2 (view and column)

As shown in FIG. 35, the interpolation means 1 (29C) selects two closest direct data which sandwich the slice position from the direct data acquired by plural detector columns in plural views and then decides them as the direct data 1 and the direct data 2.

② First interpolation process

③ Generation of complementary data 1 and complementary data 2 (independent every channel)

The complementary data generating means 29E selects two closest complementary data which sandwich the slice position every channel such that interpolation should be surely employed in the following second interpolation process. In the helical scan at Pitch=4 in the four column multi-slice CT, since displacement of the slice position is large in each channel, independent selection of optimal data per each channel is preferable to generation of continuous complementary data over all channels.

At this time, like the process ①, it must be selected which detector column in which view should be used. According to the selected result, raw data necessary for generation of the complementary data are read from a raw data memory 29B. As in the first embodiment, the interpolation process of one channel×two views is applied to the read data to generate the complementary data 1 and the complementary data 2.

For the sake of illustration, a number of complementary data are depicted in FIG. 35. However, data generation after data selection has been completed is effective rather than data selection after all data have been generated. For instance, the lower complementary data 1 of the slice position and the upper complementary data 2 of the slice position, as shown in FIG. 36, can be generated.

④ Second interpolation process

⑤ High density data generation process

⑥ Filtered back projection

Since the slice position in the center channel between the direct data 1 and the complementary data 1 and the direct data 2 and the complementary data 2 are the same, the interpolation data 1 and the interpolation data 2 obtained in ②, ④ are not susceptible to the influence caused by the change of the subject in the slice direction rather than the single slice CT. Accordingly, images reconstructed by the high density data which are generated from the interpolation data 1 and the interpolation data 2 this time can have good picture quality, and the spatial resolution in the slice direction can be improved.

In the third embodiment, the example of Pitch=4 in the four column multi-slice CT has been explained, but the present invention is not limited to such example. Pitch=2 in the four column multi-slice CT may be employed, and Pitch=(even number) in other column number such as 2, 3, 5, 6, 7, 8, . . . may be employed. In other words, a relationship between the column number and Pitch may be determined such that the slice positions of the direct data and the complementary data become substantially identical to each other in the neighborhood of the center channel.

Further, as for the selection of the complementary data, there may be various modifications, e.g., so as to cause the extrapolation, like the first embodiment.

Furthermore, although the channel direction Debluring process set forth in the second embodiment has been omitted, the third embodiment may be employed in combination with such channel direction Debluring process.

(IV) Fourth Embodiment

A fourth embodiment is a case of a slice direction filter process (bundling process or Debluring process when a basic slice thickness is made thin) in a multichannel CT.

Figure 37:
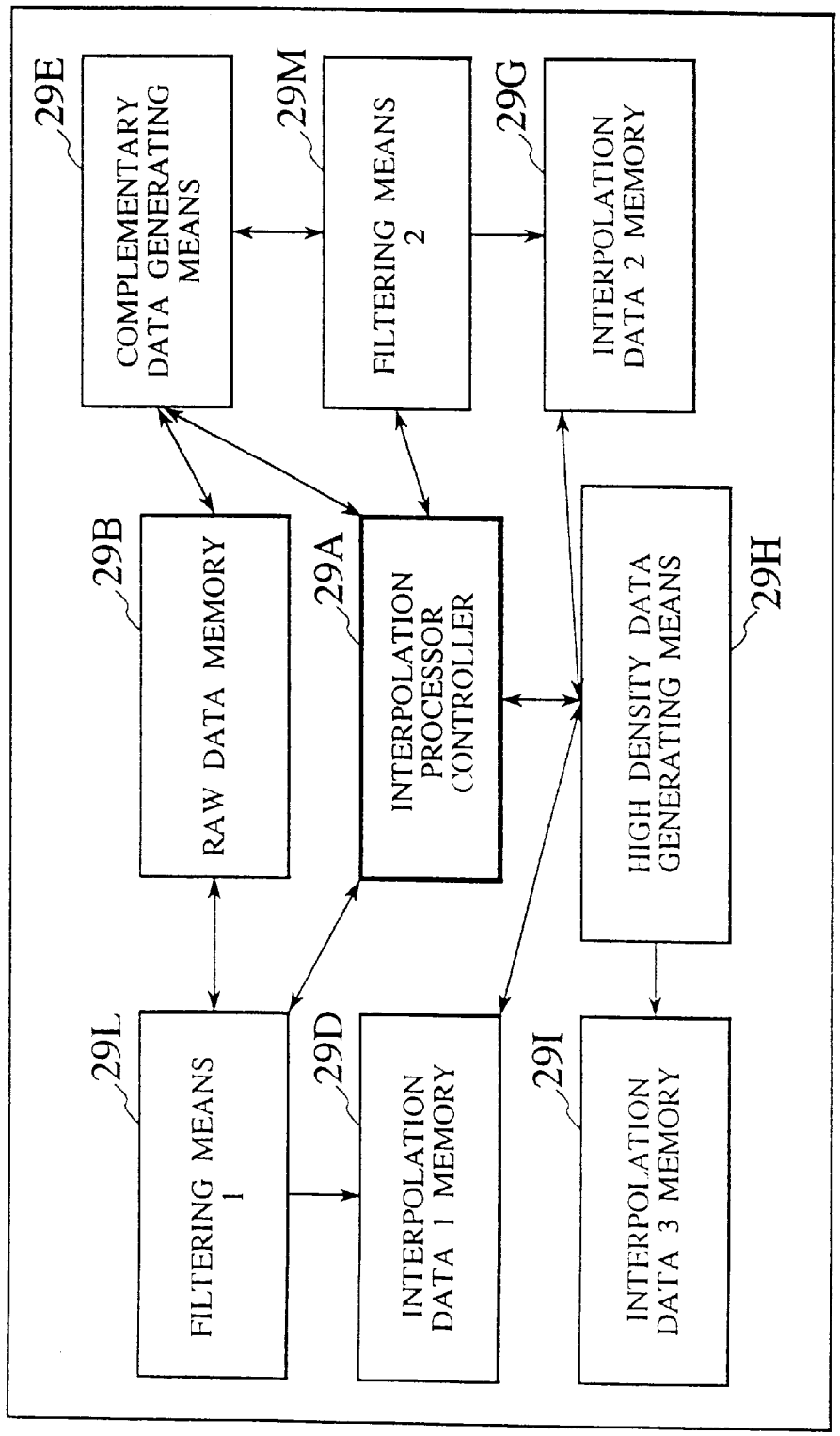
FIG. 37 is a functional block diagram of an interpolation processor in a fourth embodiment.

FIG. 37 is a block diagram of an interpolation processor 29 in the fourth embodiment.

The interpolation means 1 and the interpolation means 2 in FIG. 24 are replaced with a filtering means 1 and a filtering means 2 respectively.

Figure 38:
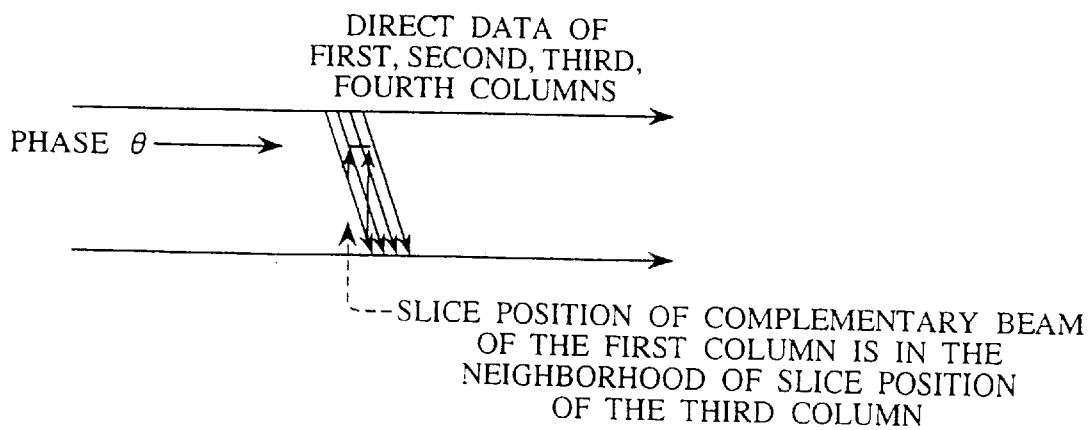
FIG. 38 is a scan diagram showing a state of phase $\theta$ in the fourth embodiment.

In addition, the basic slice thickness T is set smaller than the slice thickness in the single slice CT, for example, T/3. A conceptual view of a scan state at phase θ and process is shown in FIGS. 38 and 39.

Figure 39:
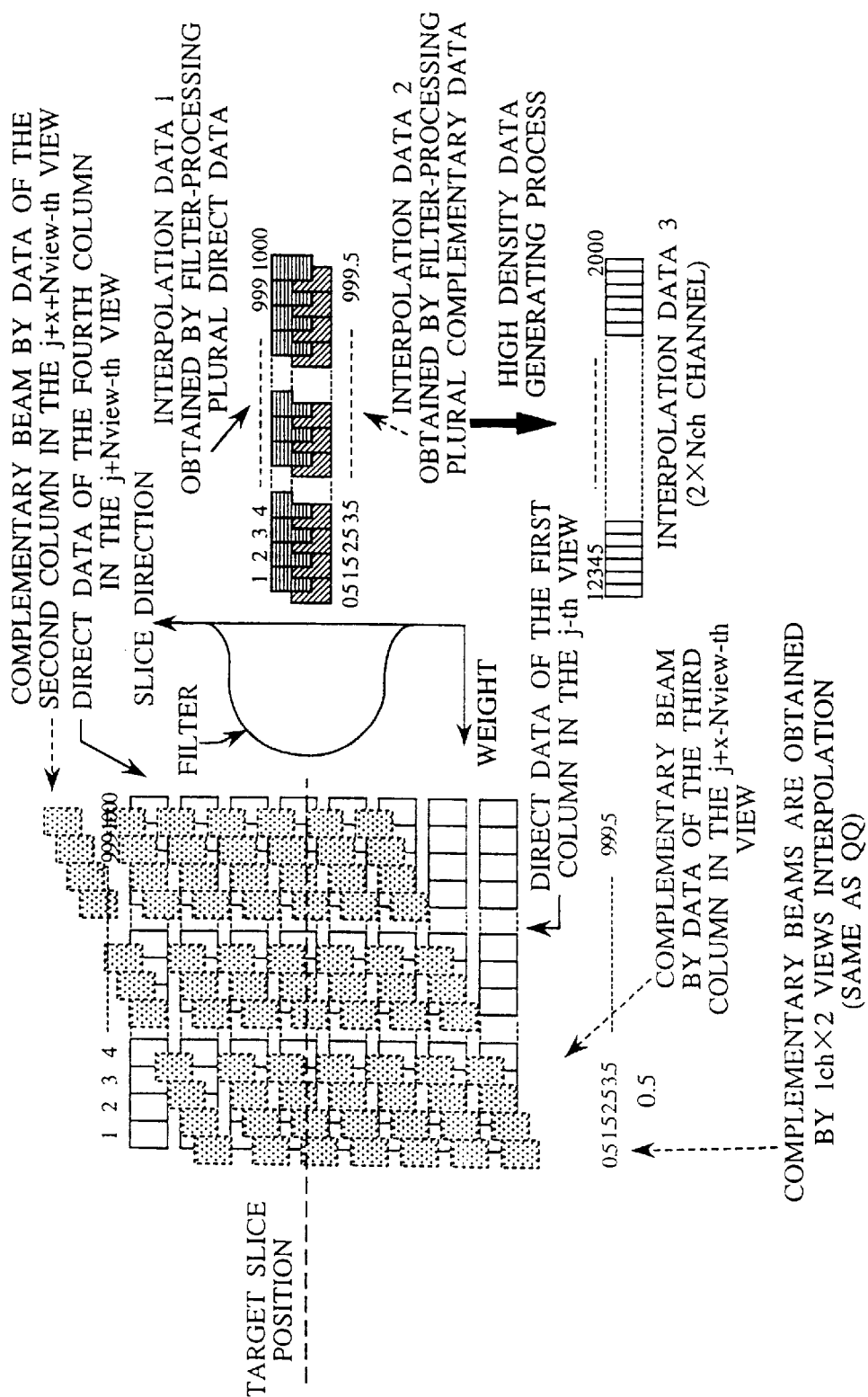
FIG. 39 is a conceptual view showing process in the fourth embodiment.

In FIG. 39, it is to be noted that the sampling density in the slice direction can be enhanced rather than FIG. 35 using the basic slice thickness T.

Also, since a sampling width of the original data, i.e., the slice thickness along the slice direction is made thin, good data in which so-called partial volume effect can be suppressed can be acquired.

Figure 40:
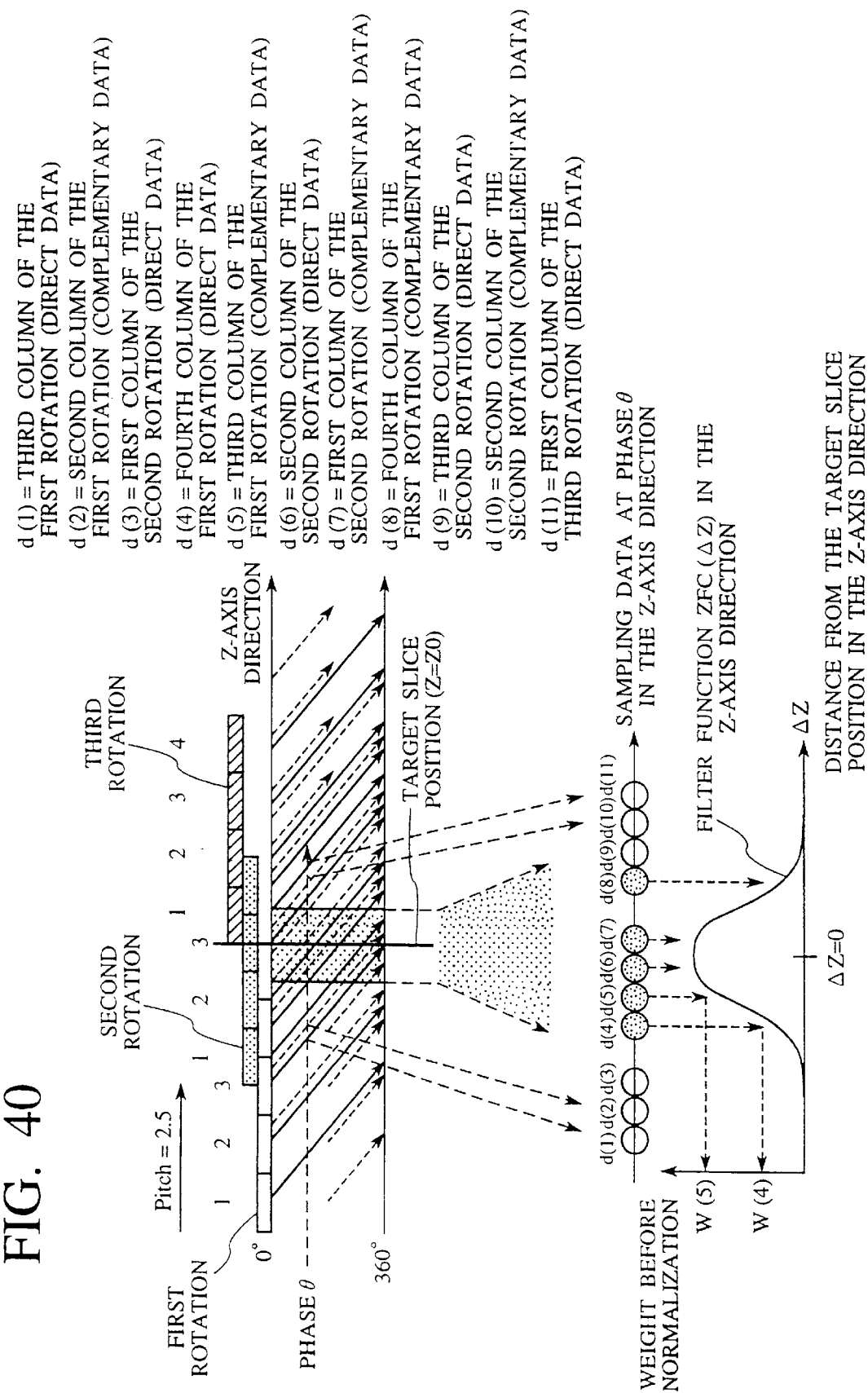
FIG. 40 is a conceptual view showing filter process used in combination with high density sampling process.

In this fourth embodiment, three or more data are selected from such data group and then filtering process such as the bundling process or the enhancing process applied to these data along the slice direction is executed independently channel by channel. Though details of the filtering process have discussed in the above literature 2 (Patent Application No. Hei 8-341739, "X-ray CT apparatus"), a conceptual view of the filtering process which is combined with the high density sampling is shown in FIG. 40.

Several examples of the profile of the filter function to carry out the bundling process or the enhancing process are shown in FIG. 41. Here a number of data are bundled by use of a low resolution function shown in FIG. 41D.

Since the processes ⑤, ⑥ are similar to those in the first embodiment, their explanation will be omitted.

① Direct data selection

As shown in FIG. 39, a filtering means 1 (29L) selects a plurality of direct data at the slice positions in the range necessary for the filtering process (called a direct data group) from the direct data of plural views and plural detector columns, and reads necessary data from a raw data memory 29B.

② Filtering process 1

The filtering means 1 (29L) applies filtering process to the direct data group selected by ① with the use of the filter indicated by the controller and shown in FIG. 39 to generate the interpolation data 1 and then stores such data 1 in the interpolation data 1 memory 29D.

As a method of the filtering process, a method of directly processing the direct data group set forth in the filter interpolation method 3 in the above literature 2 may be used, or a method of processing data group obtained by re-sampling the direct data group set forth in the filter interpolation method 4 in the above literature 2 may be used.

③ Complementary data generation

As shown in FIG. 39, a complementary data generating means 29E selects a plurality of complementary data at the slice positions in the range necessary for the filter process (called a complementary data group) from plural complementary data which can be generated from the direct data of plural views and plural detector columns, and reads necessary data from the raw data memory 29B.

Interpolation process of one channel×two views is applied to the read data to generate a complementary data group, like the first embodiment.

④ Filtering means 2

A filtering means 2 (29M) applies the filtering process to the complementary data group generated by complementary data generating means 29E with the use of the filter indicated by the controller and shown in FIG. 39 to generate the interpolation data 2, and then stores such data 2 in the interpolation data 2 memory 29G. The method of the filtering process is the same as ②.

⑤ High density data generation process

⑥ Filtered back projection

In essence the data in which the partial effect can be suppressed has been used, and high density data have been generated from the interpolation data 1 and the interpolation data 2, in which such data are added by use of a low resolution filter function, to thus reconstruct the image. As a consequence, the partial effect can be suppressed extremely in such image.

The filtering process which uses the filter to bundle data along the slice direction has been explained in the fourth embodiment, the present invention is not limited to such filter process. The so-called Debluring process may be employed by employing a filter to improve the spatial resolution in the slice direction. Since originally sufficient sampling density in the slice direction can be achieved, an effect obtained by the Debluring process is considerable. In addition, if it is combined with a high density sampling set forth in the fifth embodiment to be described next, picture quality can be improved further in this case.

Further, there is no necessity that the detector is made up of the multi-slice detector, the single slice may be employed. The basic slice thickness is not necessary to be thinned, but the conventional basic slice thickness may be employed.

Furthermore, if the above filtering process is combined with the Debluring process set forth in the above second embodiment, the spatial resolution of the trans-axial plane can be much more improved. In the filtering process along the slice direction, if the filter having the Debluring effect is employed as described above, the high spatial resolution of both the trans-axial plane and the slice direction can be achieved.

(V) Fifth Embodiment

A fifth embodiment is a case of the helical pitch 2.5 in the multichannel CT.

A configuration of an interpolation processor 29 in the fifth embodiment is identical to that in the fourth embodiment.

Here the helical scan is carried out by the high density sampling scan method having the helical pitch of Pitch=2.5 and the basic slice thickness is set to T.

Figure 42:
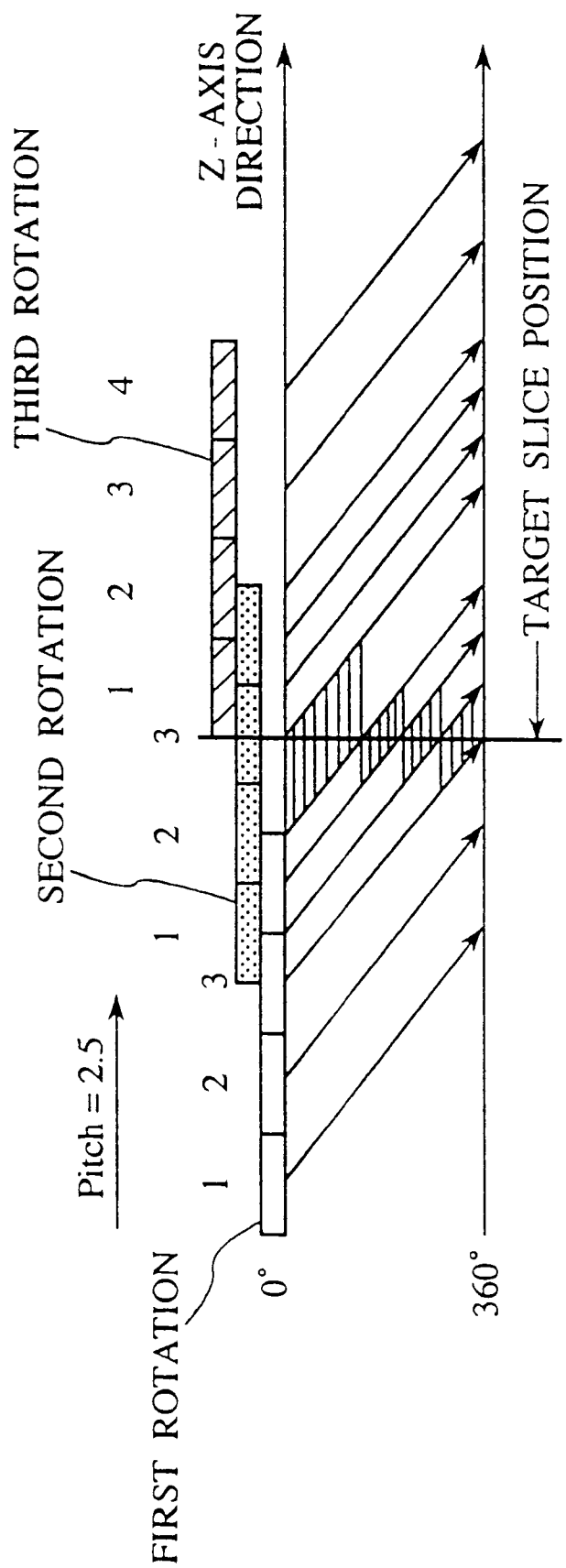
FIG. 42 is a scan diagram showing only scan for direct data at Pitch=2.5 in a high density sampling scan method.
Figure 43:
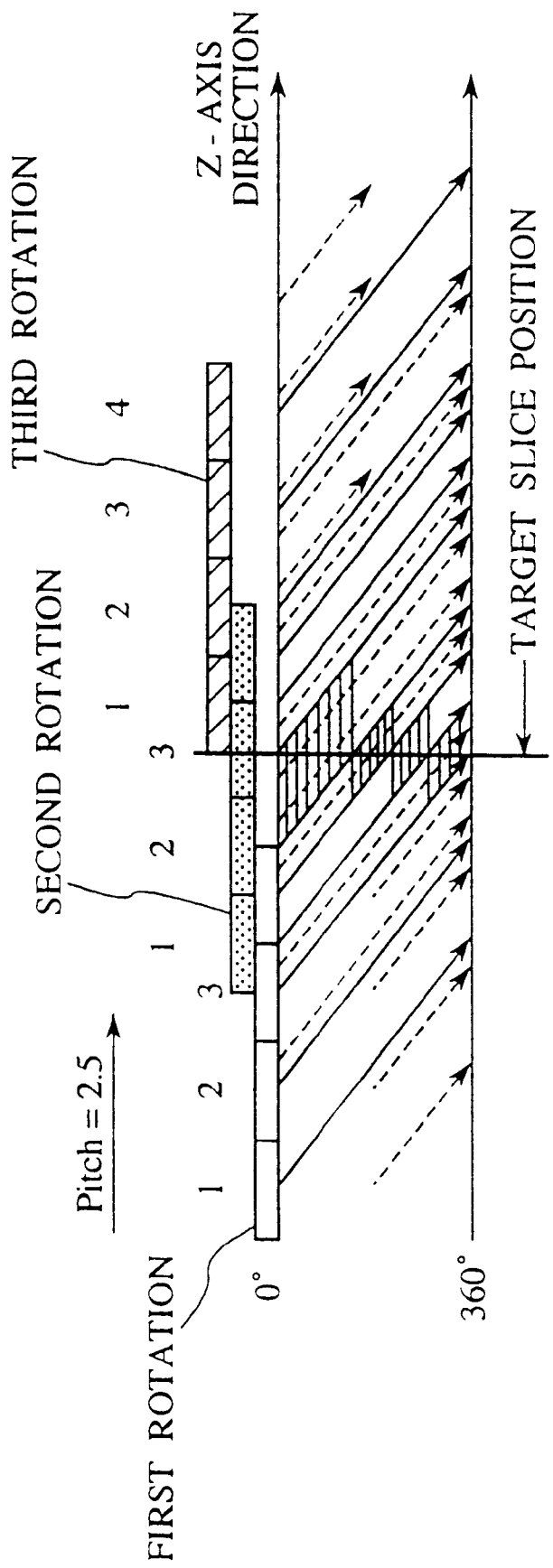
FIG. 43 is a view showing scan for direct data and complementary data (center channel) at Pitch=2.5 in the high density sampling scan method.

A scan diagram showing the only direct data at Pitch=2.5 in the high density sampling scan method is shown in FIG. 42. Also, a scan diagram for the direct data and the complementary data (of the center channel) is shown FIG. 43. It can be understood that, in the high density sampling scan method, the sampling density in the slice direction can be increased.

Figure 41A:
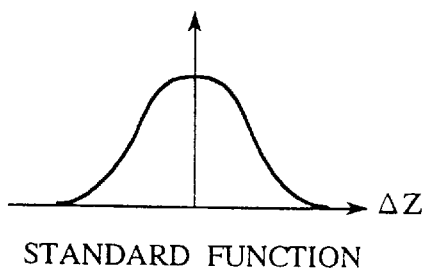
FIG. 41 is a view showing examples of profiles of filter functions.
Figure 41B:
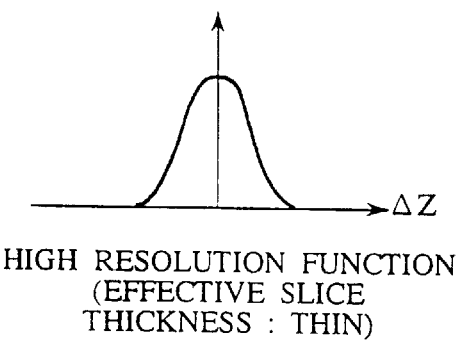
Figure 41C:
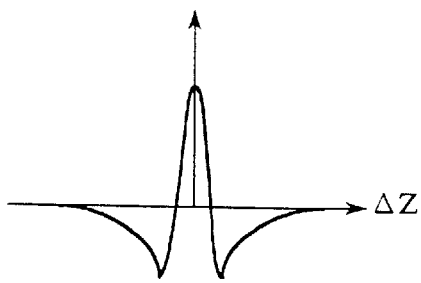
Figure 41D:
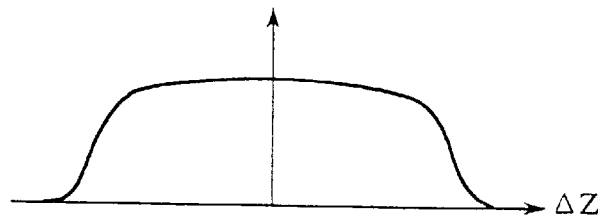
Figure 44:
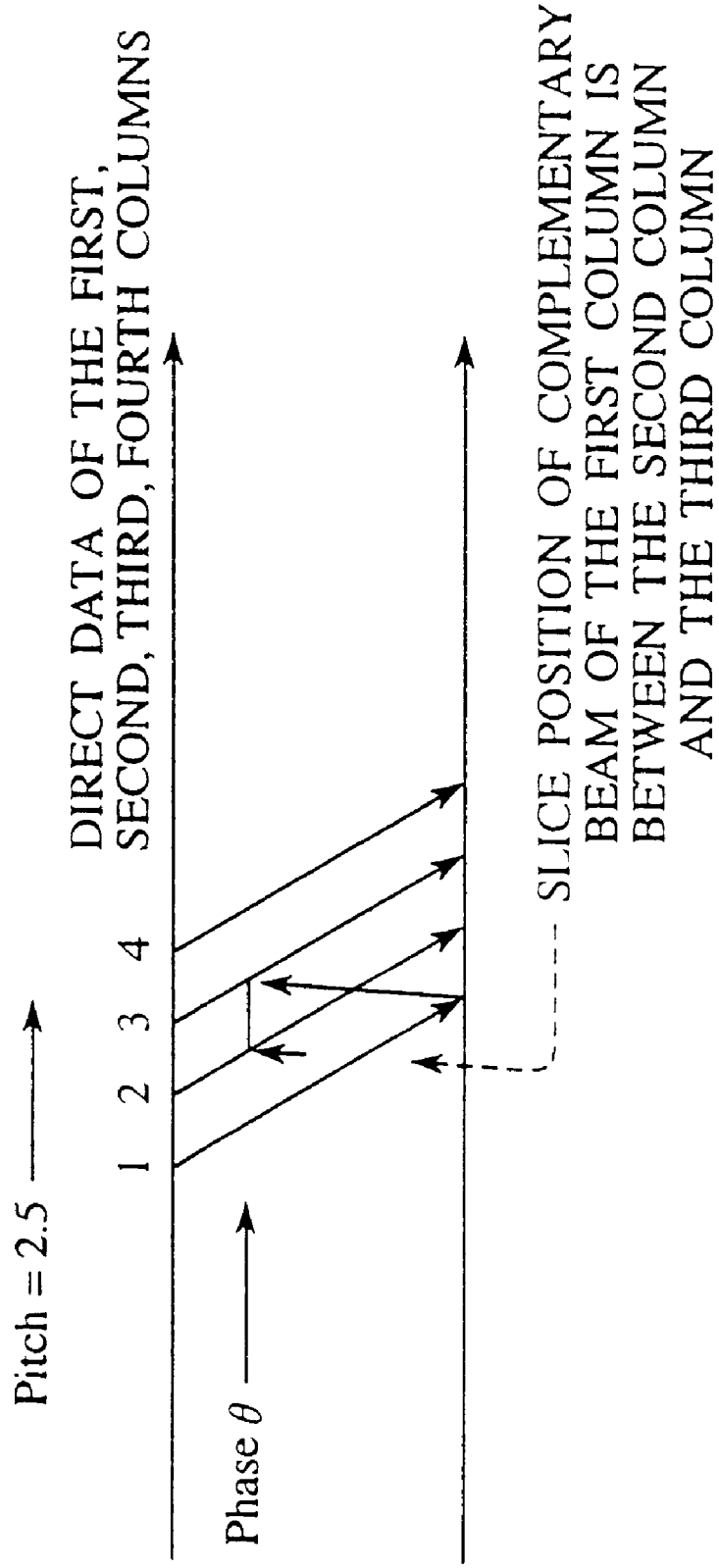
FIG. 44 is a view showing a state of phase $\theta$ in a fifth embodiment.
Figure 45:
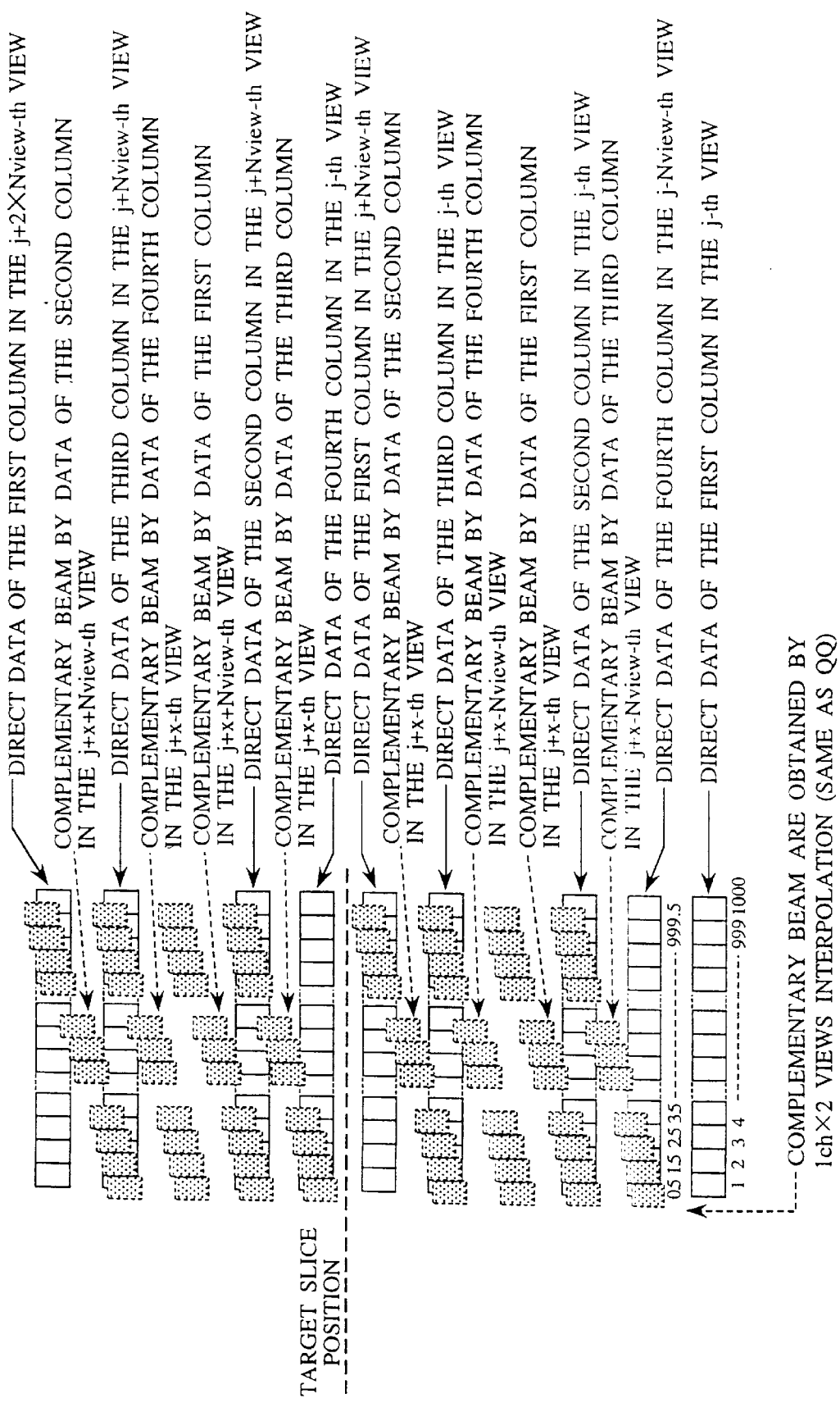
FIG. 45 is a view showing a scan state at phase $\theta$ in the fifth embodiment.
Figure 46:
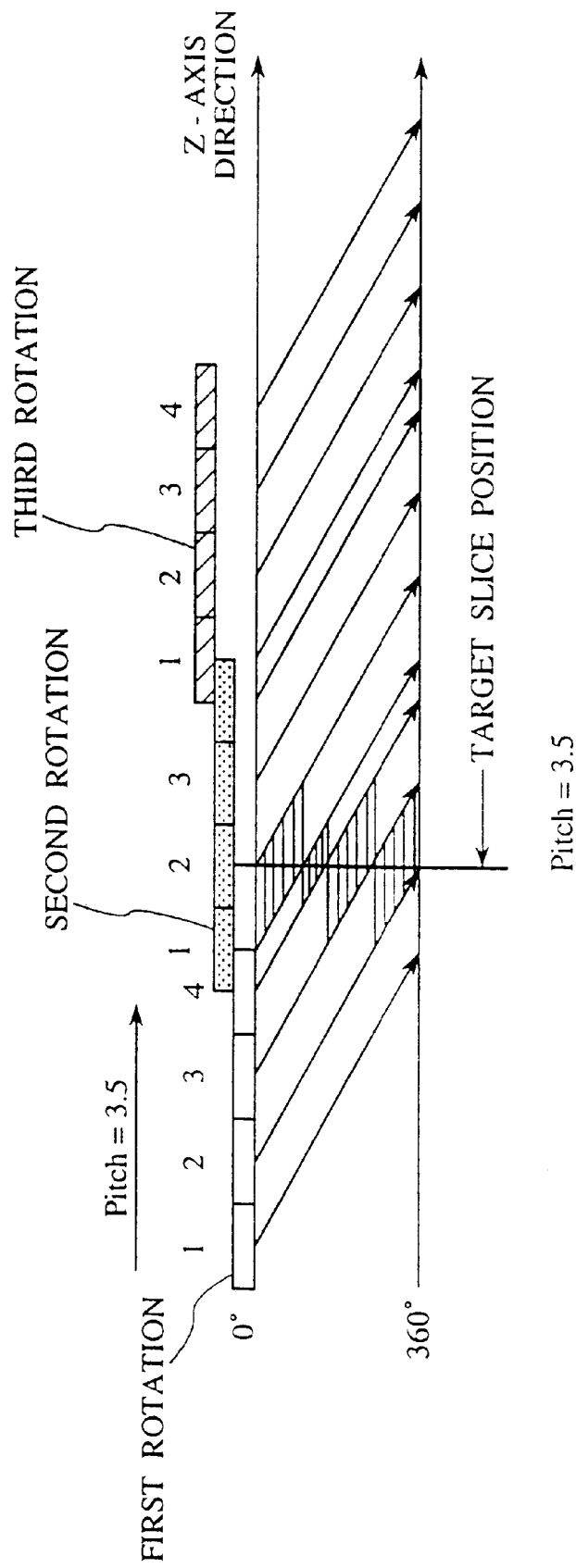
FIG. 46 is a scan diagram showing scan at Pitch=3.5 in the four column multi-slice CT.
Figure 47:
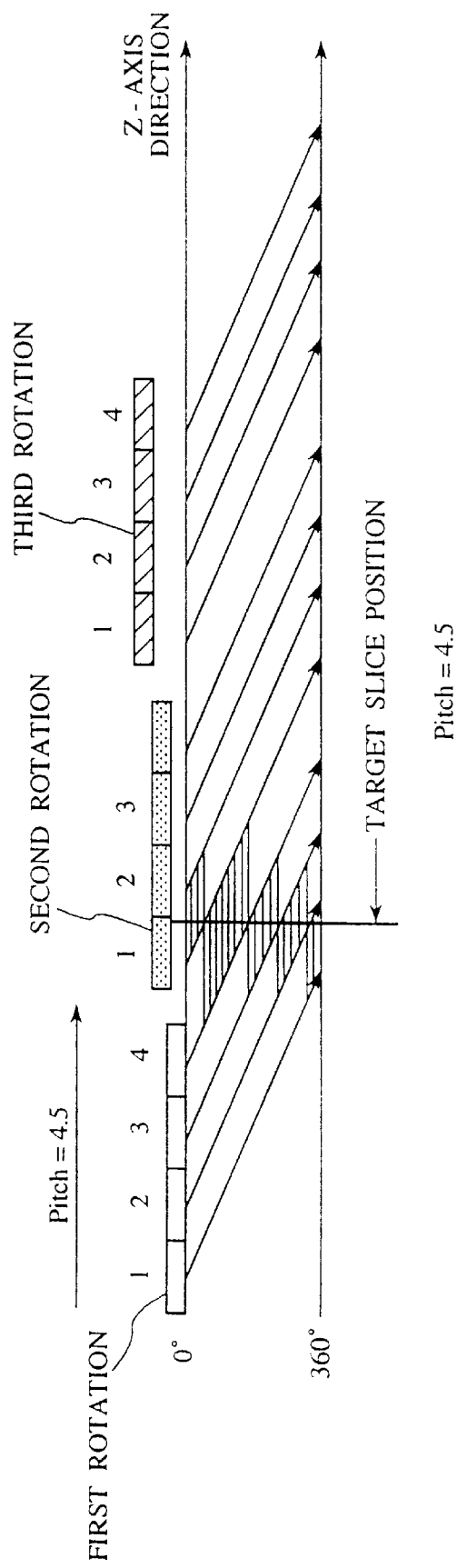
FIG. 47 is a scan diagram showing scan at Pitch=4.5 in the four column multi-slice CT.
Figure 48:
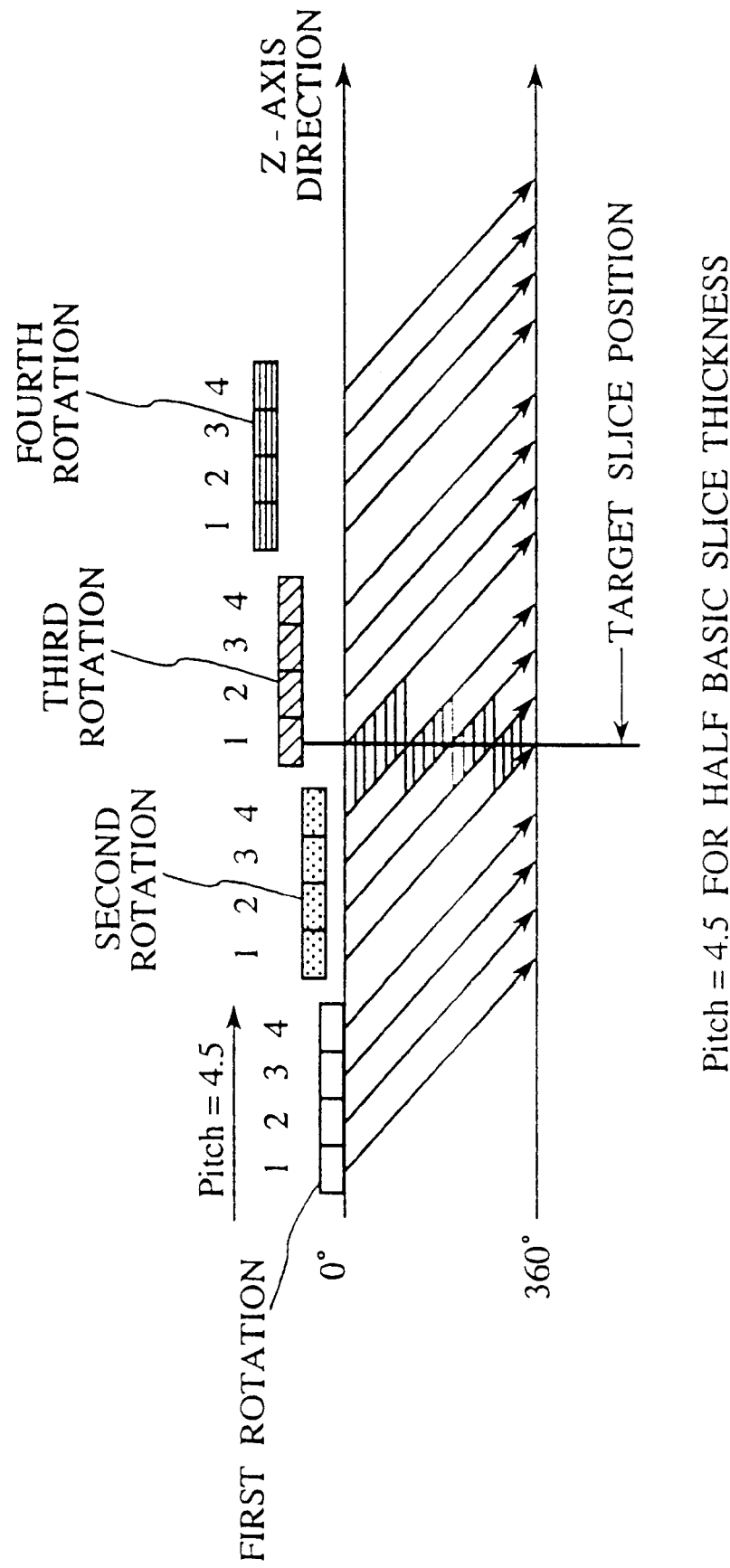
FIG. 48 is a scan diagram showing scan at Pitch=4.5 if a basic slice thickness is reduced by half.
Figure 49:
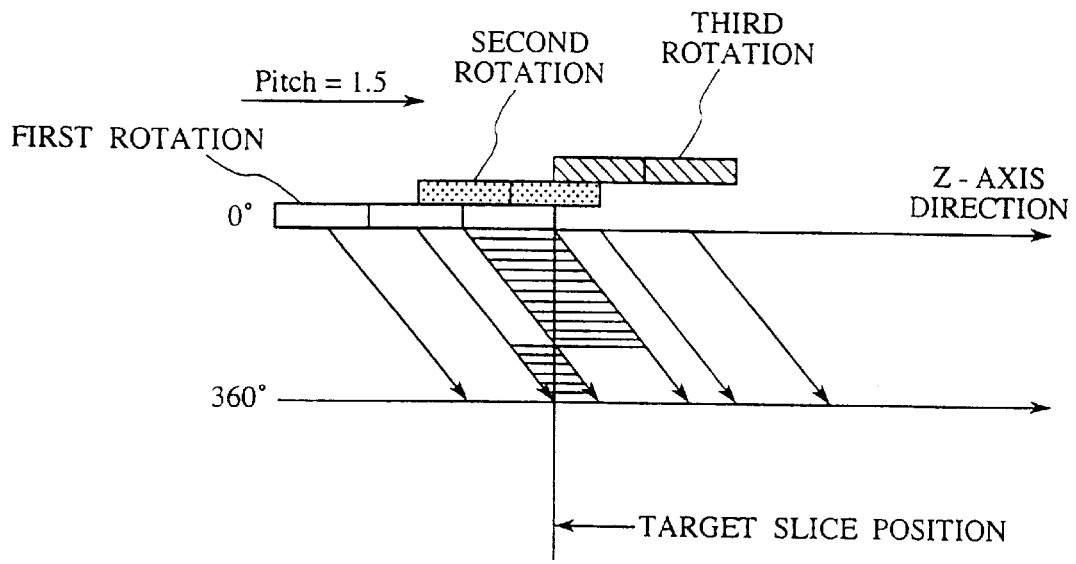
FIG. 49 is a scan diagram showing scan at Pitch=1.5 in a two column multi-slice CT.
Figure 50:
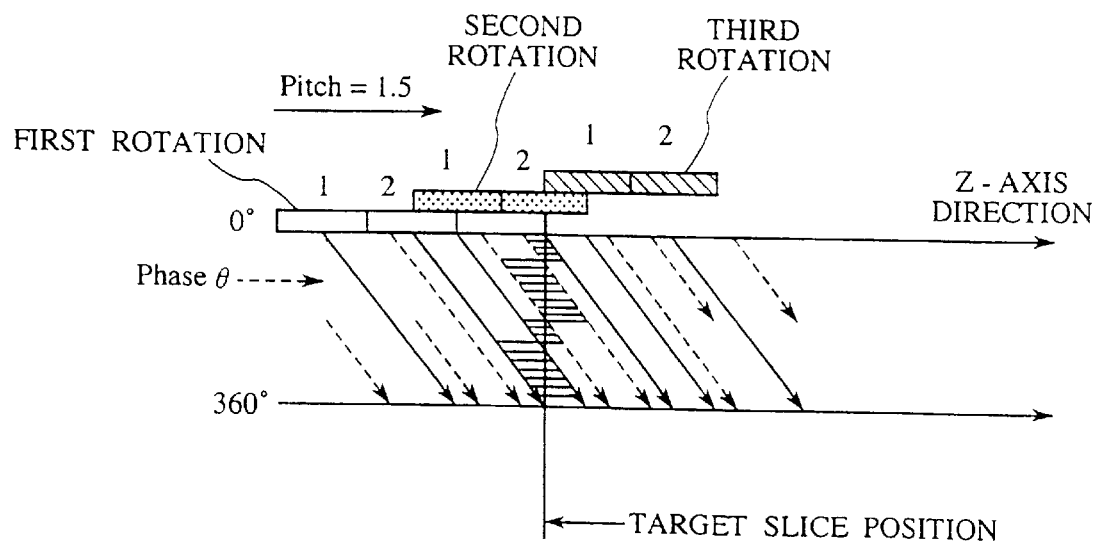
FIG. 50 is a scan diagram showing a complementary beam interpolation method if Pitch=1.5 is set in the two column multi-slice CT.
Figure 51:
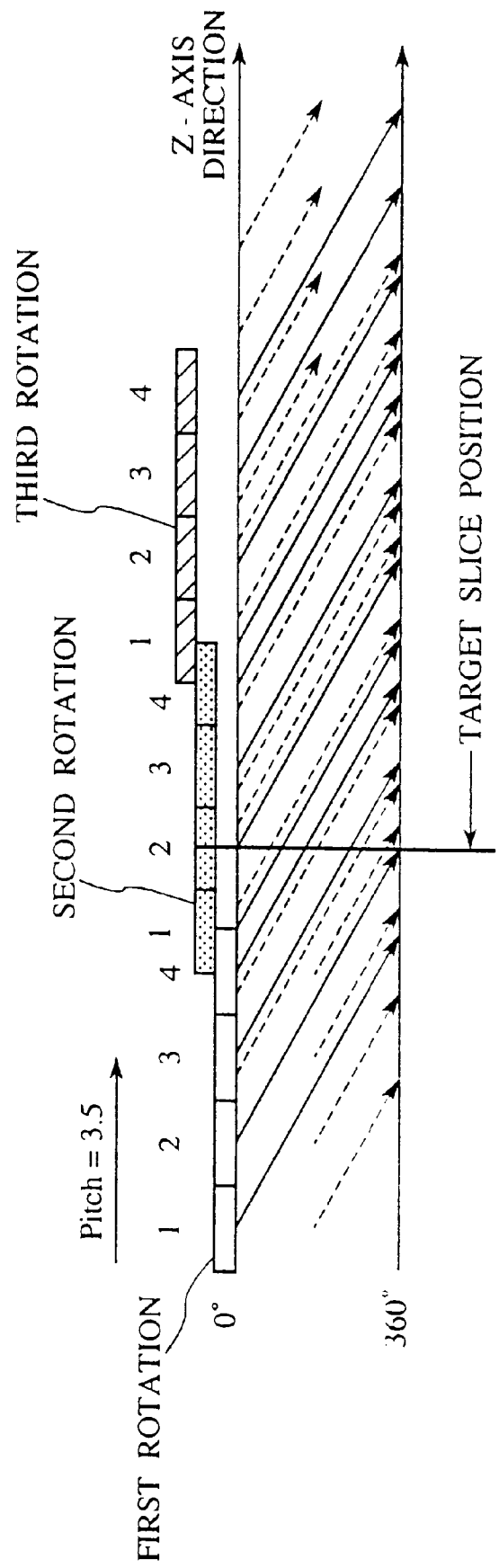
FIG. 51 is a scan diagram showing a complementary beam interpolation method if Pitch=3.5 is set in the four column multi-slice CT.
Figure 52:
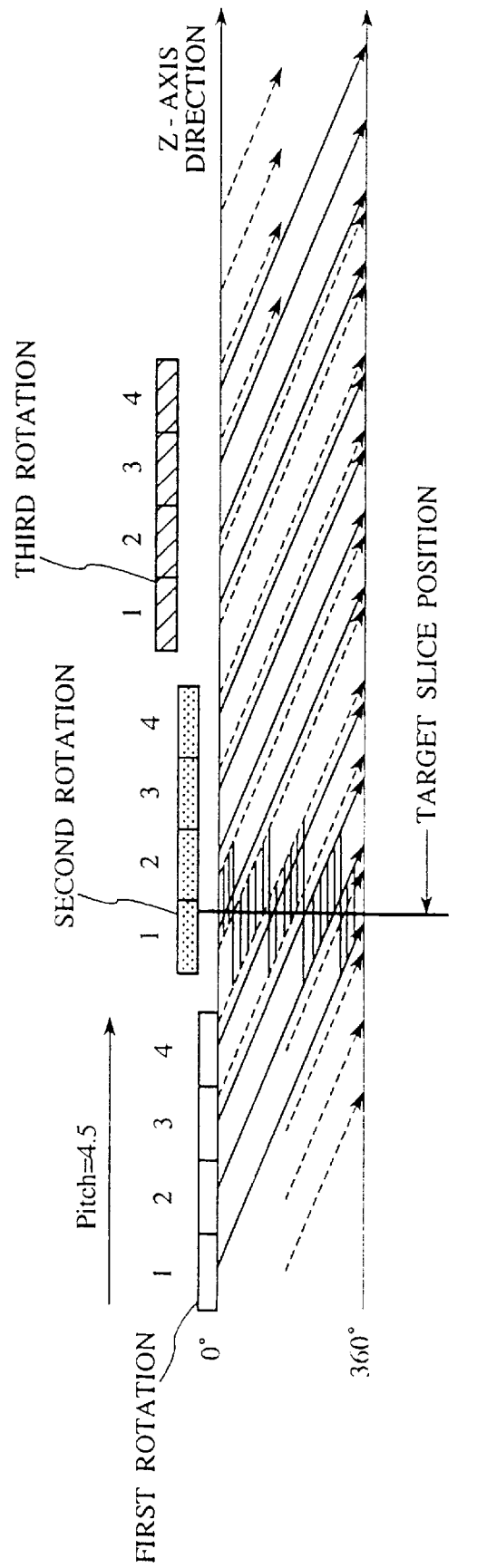
FIG. 52 is a scan diagram showing the complementary beam interpolation method if Pitch=4.5 is set in the four column multi-slice CT.

A scan state at the phase θ shown in FIG. 44 is shown in FIG. 45. It can be seen that, if FIG. 45 is compared with FIG. 35 in which the scan state at Pitch=4 is shown, the sampling density in the slice direction can be enhanced. In the filtering process in the slice direction, a standard function shown in FIG. 41A is employed.

Since the processes ②, ④, ⑤, ⑥ are identical to those in the fourth embodiment, their explanation will be omitted hereunder. Since the filtering process after data selection is identical to FIG. 39 in the fourth embodiment, its explanation will be omitted.

① Direct data selection

As shown in FIG. 45, the filtering means 1 (29L) selects a plurality of direct data at the slice positions in the range necessary for the filtering process (called a direct data group) from the direct data of plural views and plural detector columns arranged in complicated sequence, and reads necessary data from the raw data memory 29B.

② Filtering process 1

③ Complementary data generation

As shown in FIG. 45, the complementary data generating means 29E selects a plurality of complementary data at the slice positions in the range necessary for the filtering process (called a complementary data group) from plural complementary data arranged in complicated sequence, which can be generated from the direct data of plural views and plural detector columns arranged in complicated sequence, and reads necessary data from the raw data memory 29B.

The interpolation process of one channel×two views is applied to the read data to then generate a complementary data group same in the above first embodiment.

④ Filtering process 2

⑤ High density data generation process

⑥ Filtered back projection

In the fifth embodiment, since data obtained by virtue of high density sampling are filter-processed in the slice direction while the basic slice thickness is kept to be T as it is, the image with high picture quality can be accomplished.

Although the example of scan at Pitch=2.5 in the four column multi-slice CT has been explained in the fifth embodiment, the present invention is not limited to such example. Variations such as Pitch=1.5, 2.0, 3.0, 3.5, 4.5 or Pitch=1.5 in the two column multi-slice may be applicable arbitrarily.

As an example, scan diagrams for scan at Pitch=3.5, Pitch=4.5 in the four column multi-slice CT and scan at Pitch=1.5 in the two column multi-slice CT are shown in FIGS. 46 to 48 and FIGS. 49 to 52 respectively.

Also, the fifth embodiment may be combined with the Debluring process set forth in the above second embodiment or the above fourth embodiment.

(VI) Sixth Embodiment

In the first to fifth embodiments and their modifications explained above, the first interpolation data as the integer channel data at the target slice position have been generated by applying the interpolation process and/or the filtering process of the direct data previously, then similarly the second interpolation data as the minor channel data at the target slice position have been generated by applying the interpolation process and/or the filtering process of the complementary data, and then the high density data at the target slice position have been generated by combining the first interpolation data with the second interpolation data.

However, in the present invention, the high density direct data as the first interpolation data and the high density complementary data as the second interpolation data may be generated by applying the interpolation process in the channel direction in advance, and then the high density data at the target slice position may be generated by applying the complementary beam interpolation process (i.e., helical interpolation process) based on the first interpolation data and the second interpolation data.

The sixth embodiment shows a case where, after the high density direct data and high density complementary data are generated by interpolation respectively, the high density data at the target slice position will then be obtained by the helical interpolation by use of these data.

A system configuration of an X-ray CT apparatus to which the sixth embodiment is applied is similar to the X-ray CT apparatus shown in FIG. 23, but a detailed configuration of an interpolation processor 29 is different.

Figure 53:
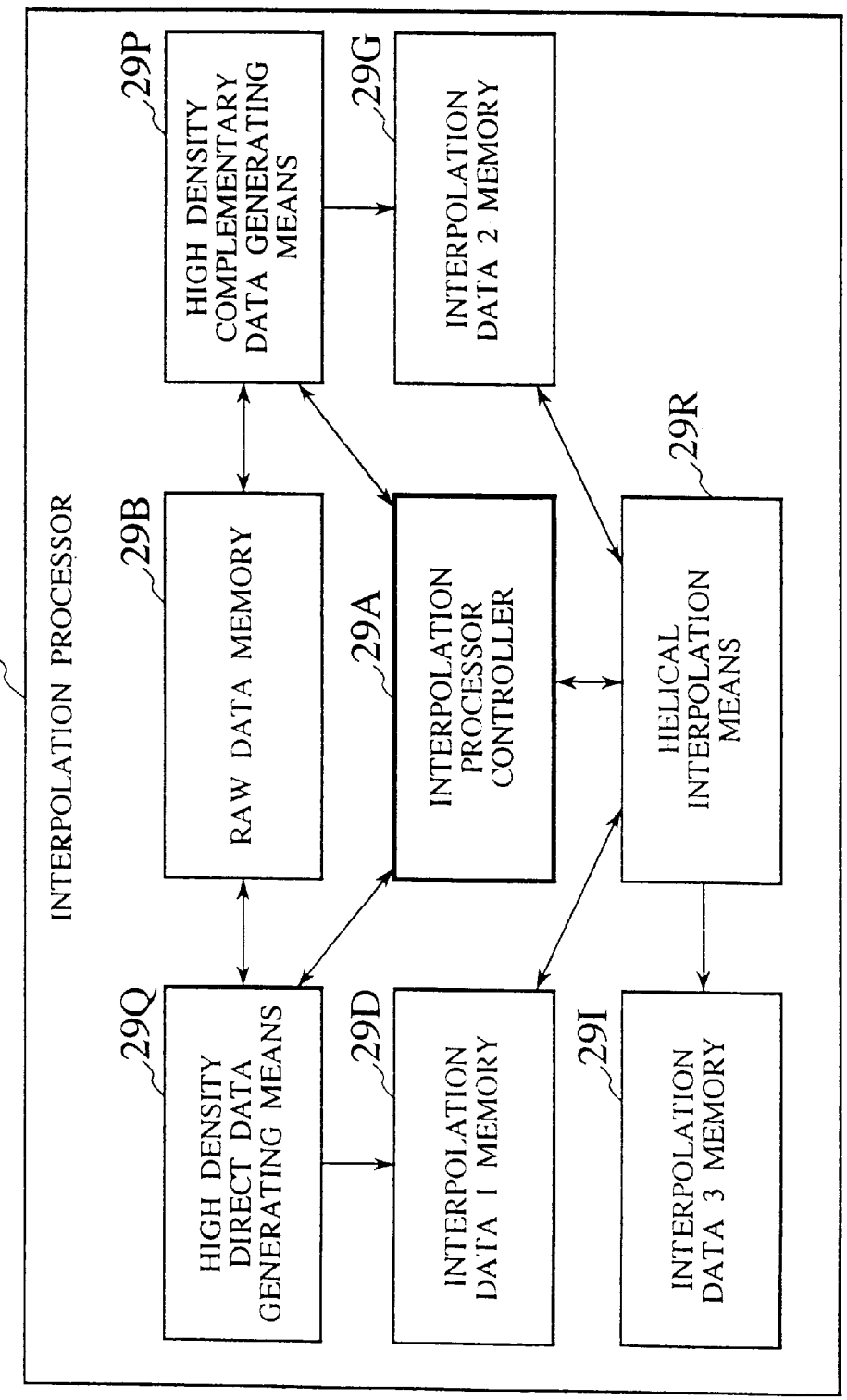
FIG. 53 is a functional block diagram of an interpolation processor in a sixth embodiment.
Figure 54:
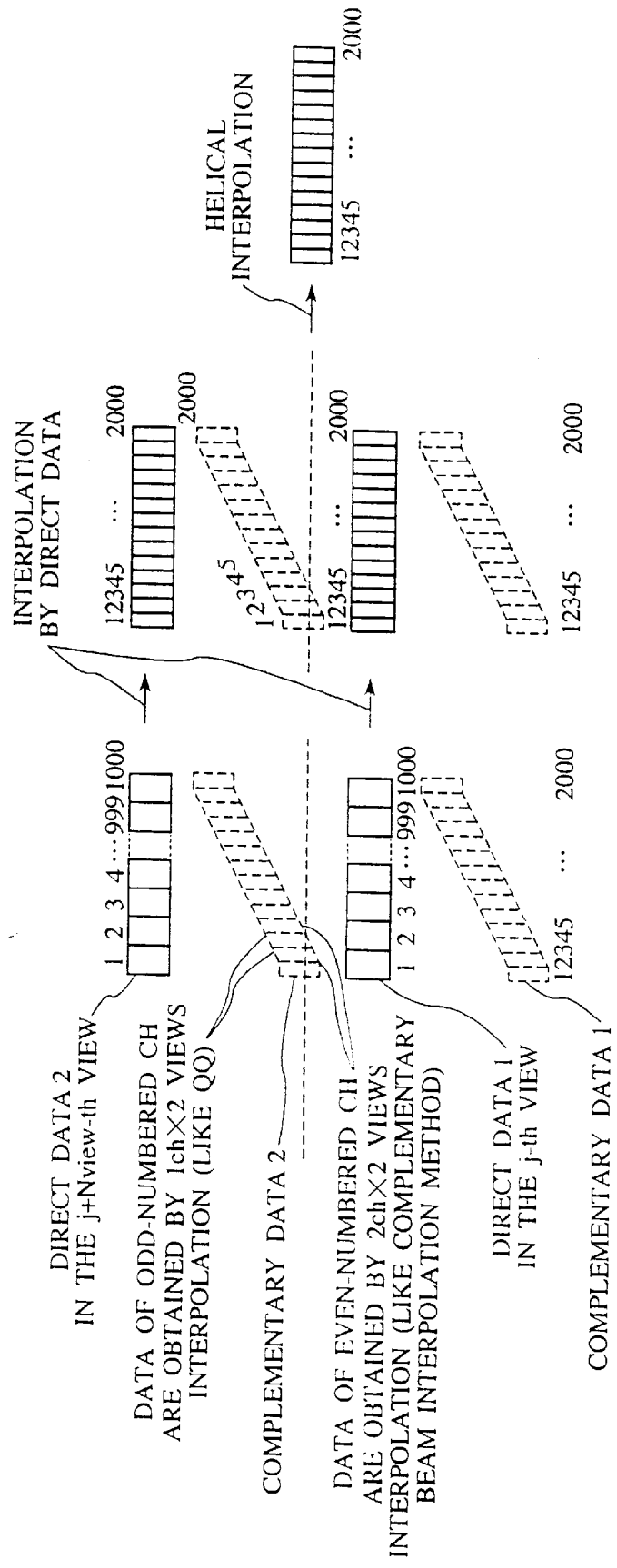
FIG. 54 is a conceptual view showing process in the sixth embodiment.
Figure 55:
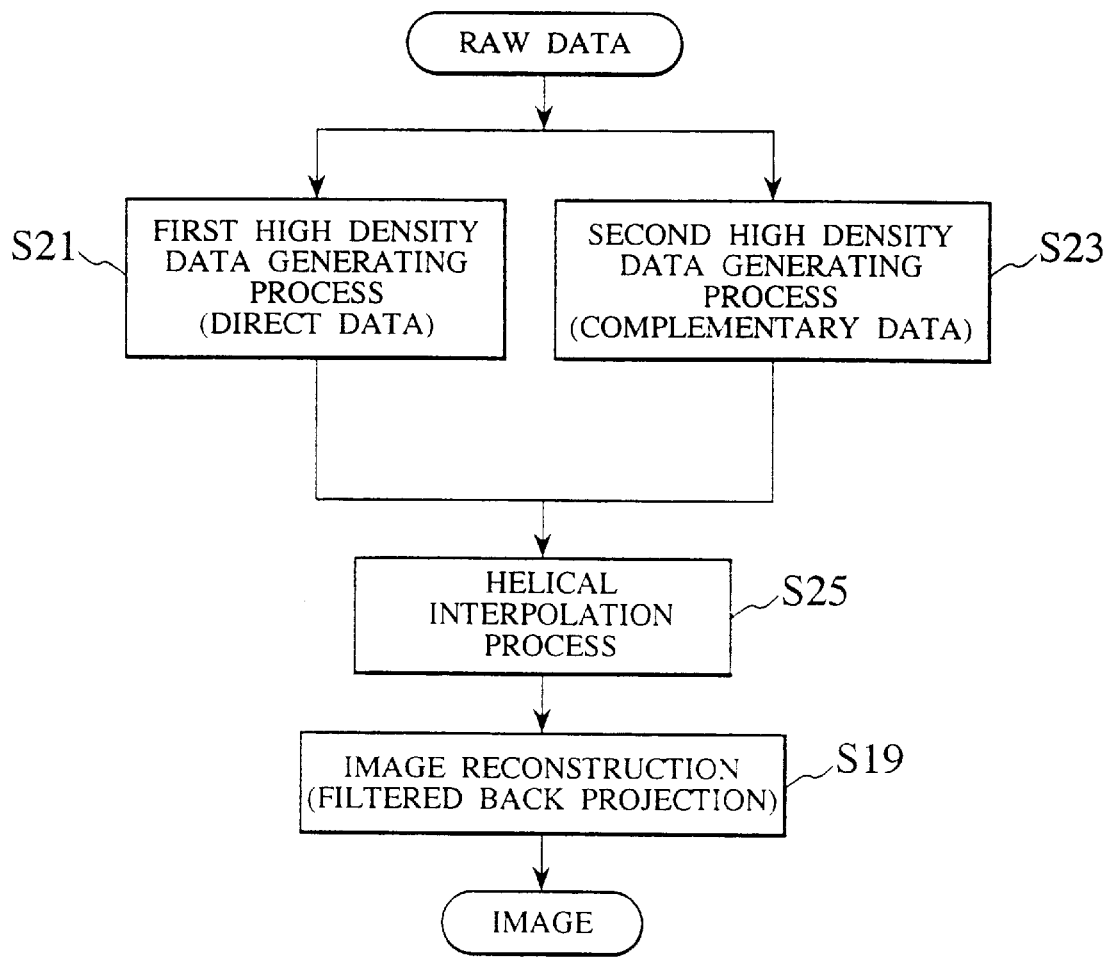
FIG. 55 is a flowchart showing flow of process in the sixth embodiment.

FIG. 53 is a view of detailed configuration of the interpolation processor 29 in FIG. 23, FIG. 54 is a conceptual view of process in the sixth embodiment, FIG. 55 is a flowchart showing flow of process in the sixth embodiment.

In FIG. 53, the interpolation processor 29 in the sixth embodiment comprises an interpolation processor controller 29A for controlling the overall interpolation processor, a raw data memory 29B for storing raw data obtained by scanning the subject, a high density direct data generating means 29Q for generating high density direct data, a high density complementary data generating means 29P for generating high density complementary data, a helical interpolation means 29R, an interpolation data 1 memory 29D, an interpolation data 2 memory 29G, and an interpolation data 3 memory 29I.

Since processes executed until the raw data acquired by scanning the subject are stored into the raw data memory 29B are similar to those in the first embodiment, only succeeding processes will be explained.

Plural data at a certain phase θ are shown in FIG. 54. The j-th view as the lower direct data 1 and the j+Nview-th view as the upper direct data 2, which are positioned to sandwich the slice position, will be discussed. These are similar to the data used in the above 360° interpolation methods (see FIG. 14 and FIG. 19).

In addition, the lower complementary data 1 and the upper complementary data 2, which are positioned to sandwich the slice position, will be discussed.

① First high density data (direct data) generation process

The high density direct data generating means 29Q receives the direct data 1 and the direct data 2 from the raw data memory 29B, then generates the first high density data group hp1 by applying the contiguous channel interpolation in the same view to respective direct data according to following equations, and then stores the data into the interpolation data 1 memory 29D (step S21 in FIG. 55). Weight of interpolation is constant over all channels.

If the direct data of the k-th channel in the j-th view is assumed as $D(j,k)$, it is possible to formulate following equations.

$$hp1(j, 2 \times k) = D(j, k)$$

$$hp1(j, 2 \times k-1) = [D(j, k-1) + D(j,k)]/2 \quad \text{[Equations 7]}$$

The interpolation data 1 are data of the first, second, third, . . . , 2000-th channels.

② Second high density data (complementary data) generation process

Figure 1:
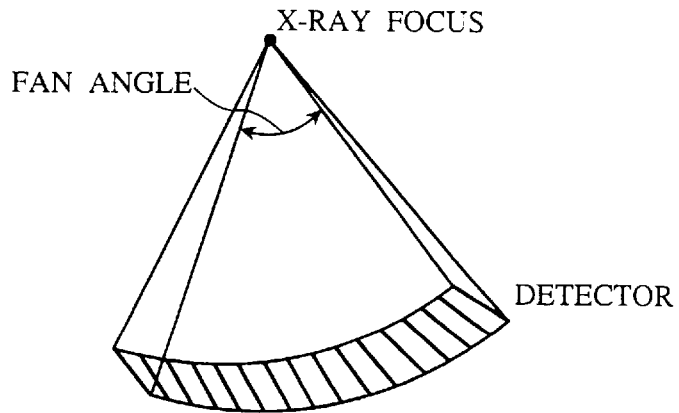
FIG. 1 is a view showing a schematic configuration of a single slice CT.
Figure 2:
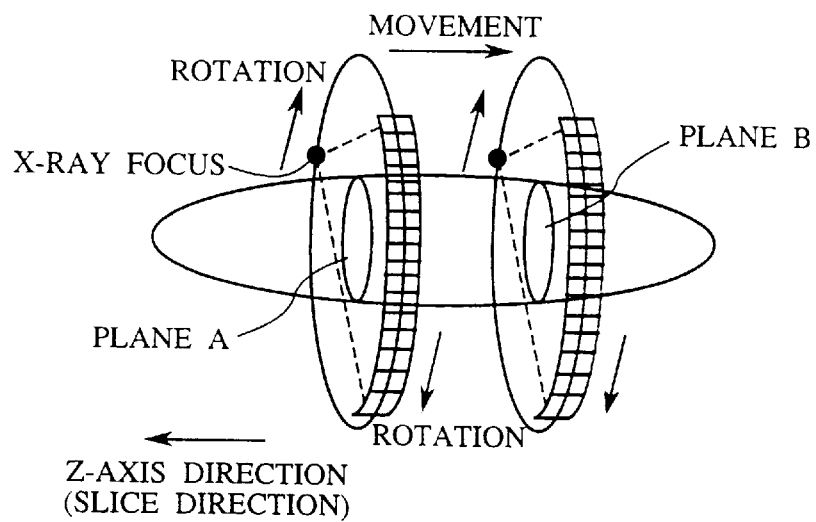
FIG. 2 is a conceptual view showing a conventional scan.
Figure 3:
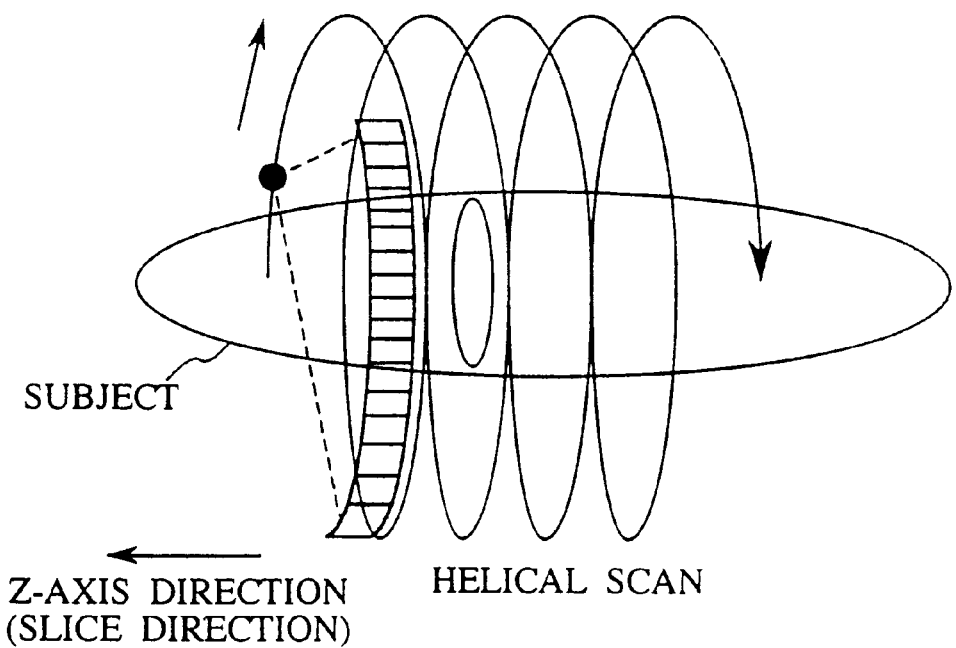
FIG. 3 is a conceptual view showing a helical scan.
Figure 4:
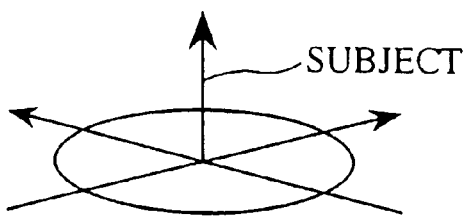
FIG. 4 is a conceptual view showing a subject.
Figure 5A:
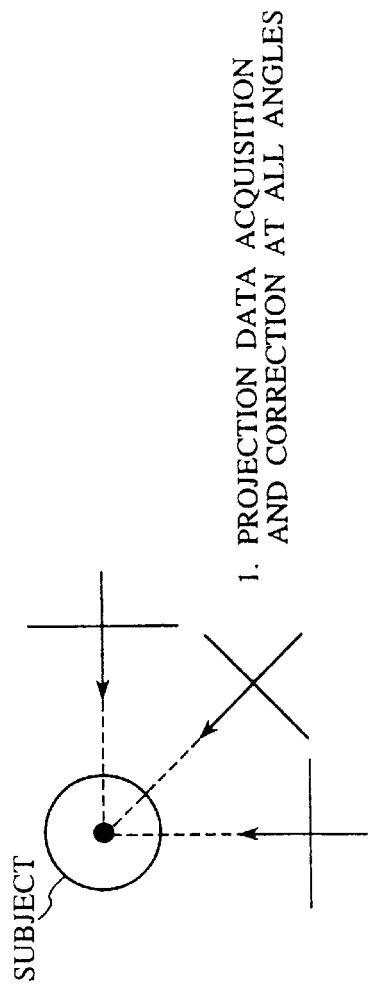
FIG. 5 is a view showing image reconstruction process in an X-ray CT apparatus.
Figure 5C:
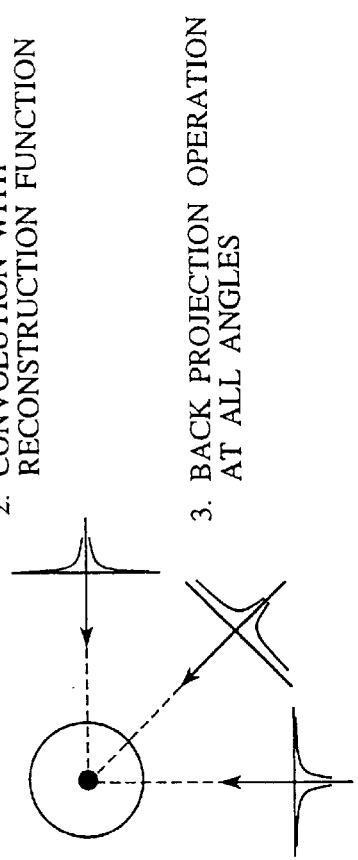
Figure 5B:
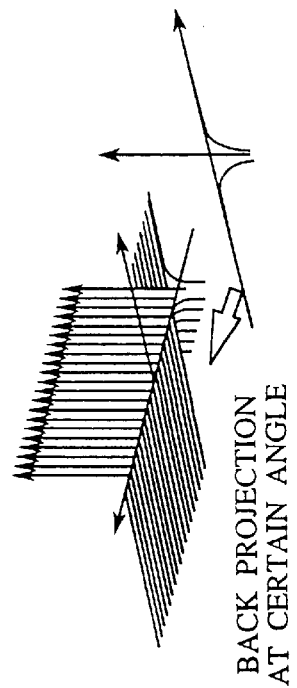
Figure 6A:
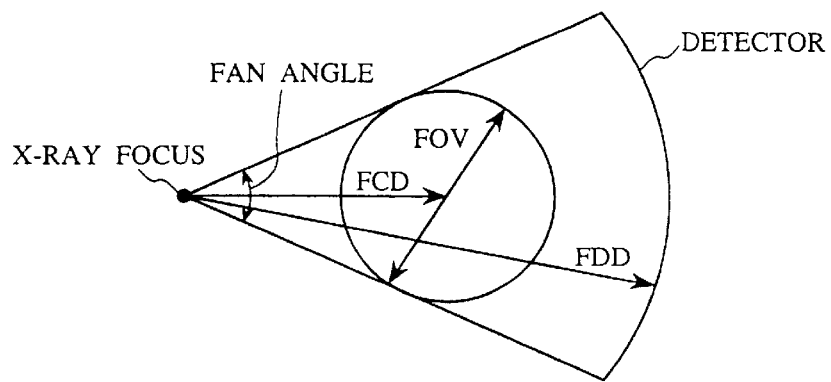
FIG. 6 is a view showing a geometry of a multi-slice X-ray CT apparatus.
Figure 6B:
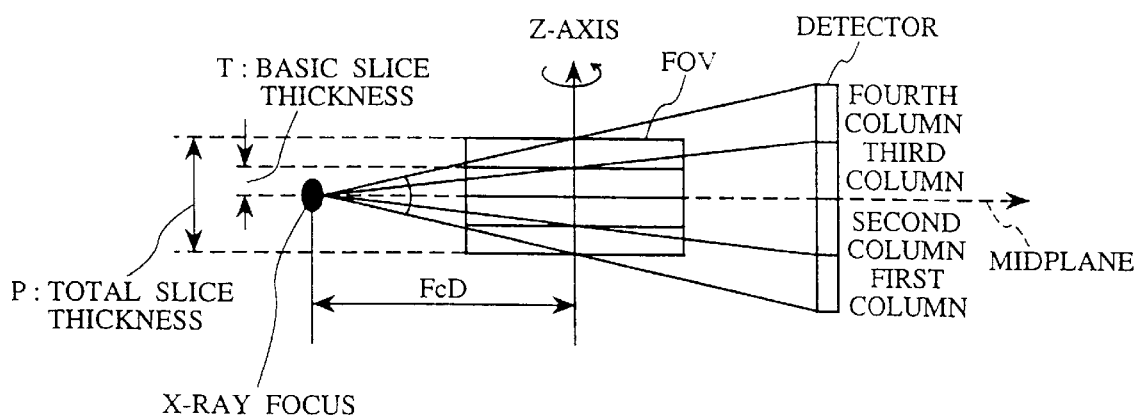
Figure 7:
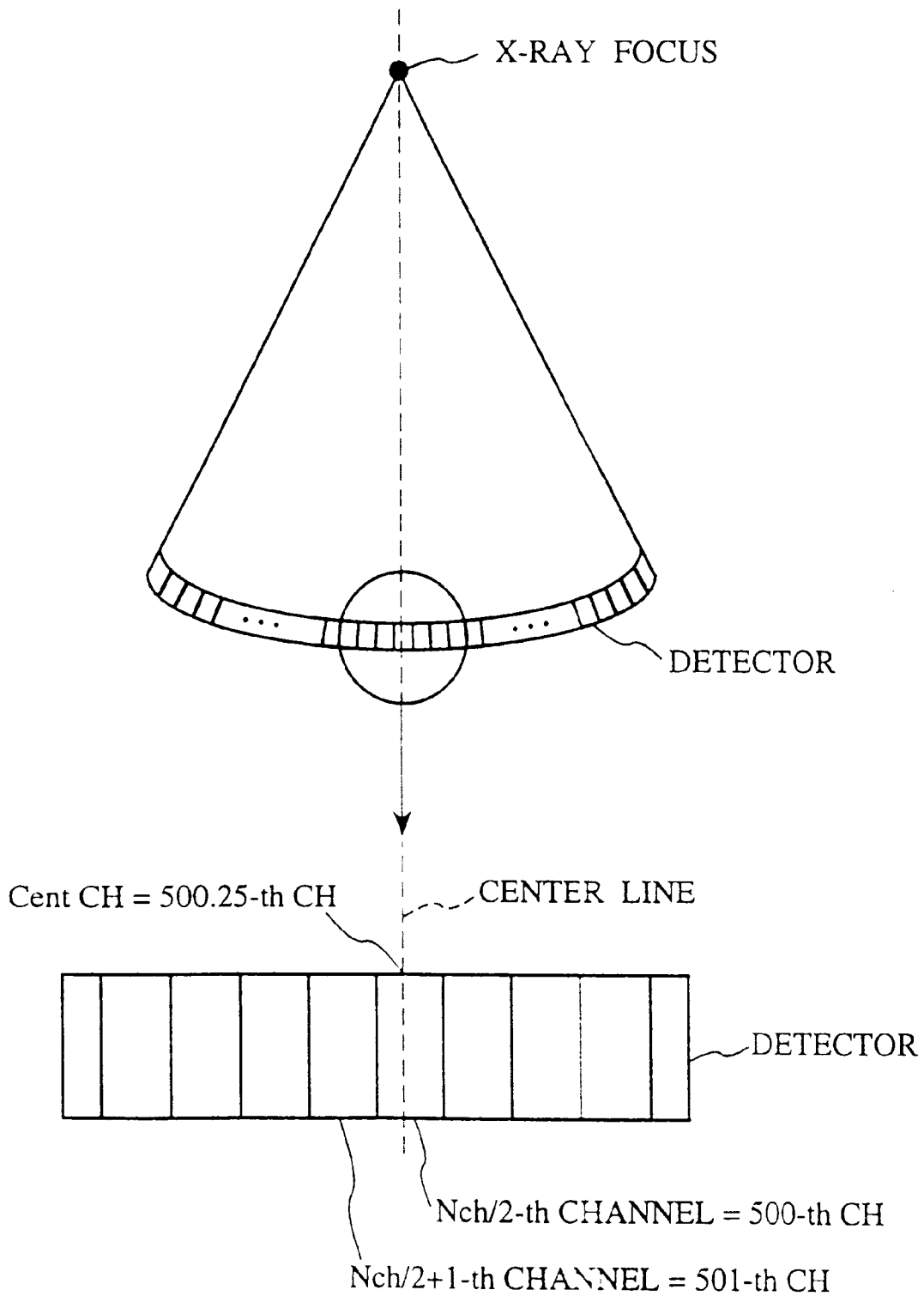
FIG. 7 is a view showing an offset fitting state of QQ.
Figure 8A:
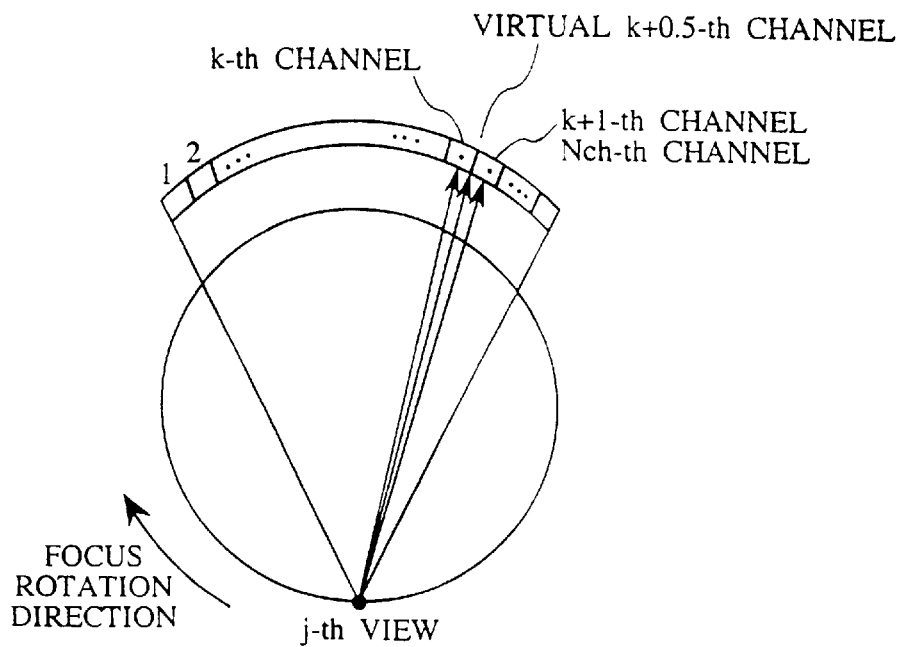
FIG. 8 is a view showing process of QQ.
Figure 8B:
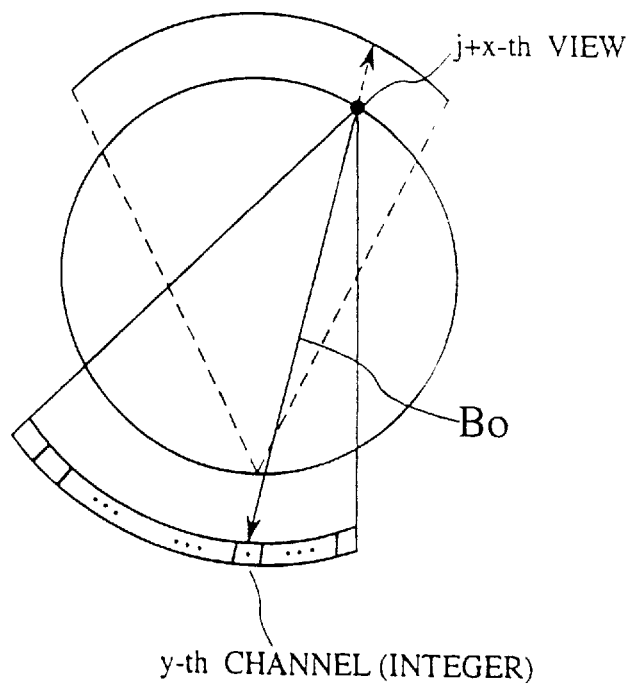
Figure 9:
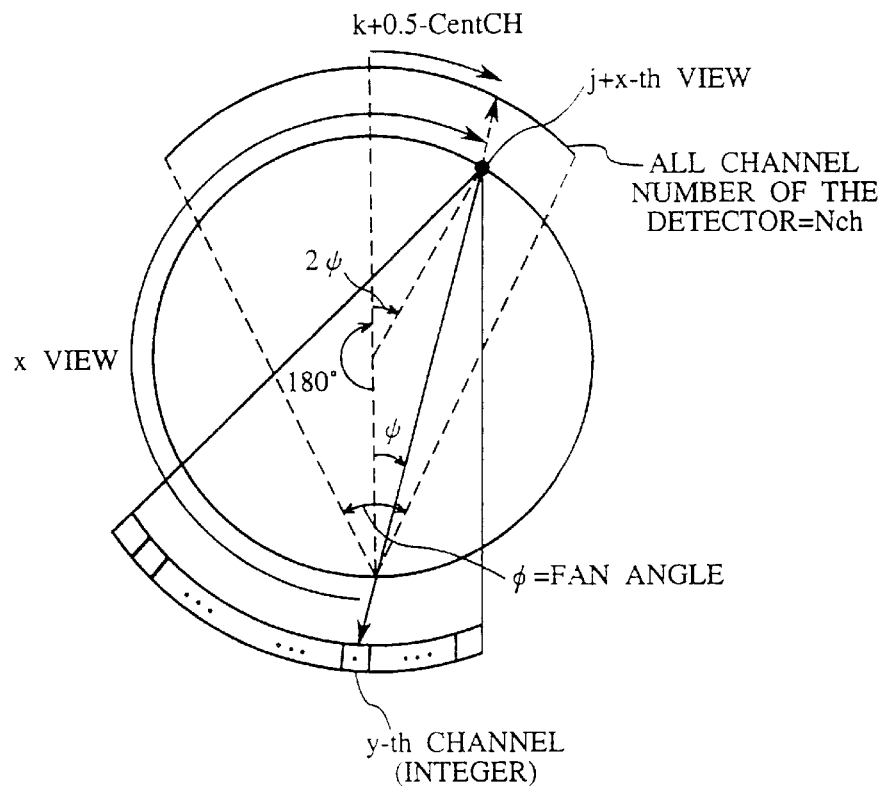
FIG. 9 is a view showing process of QQ.
Figure 10:
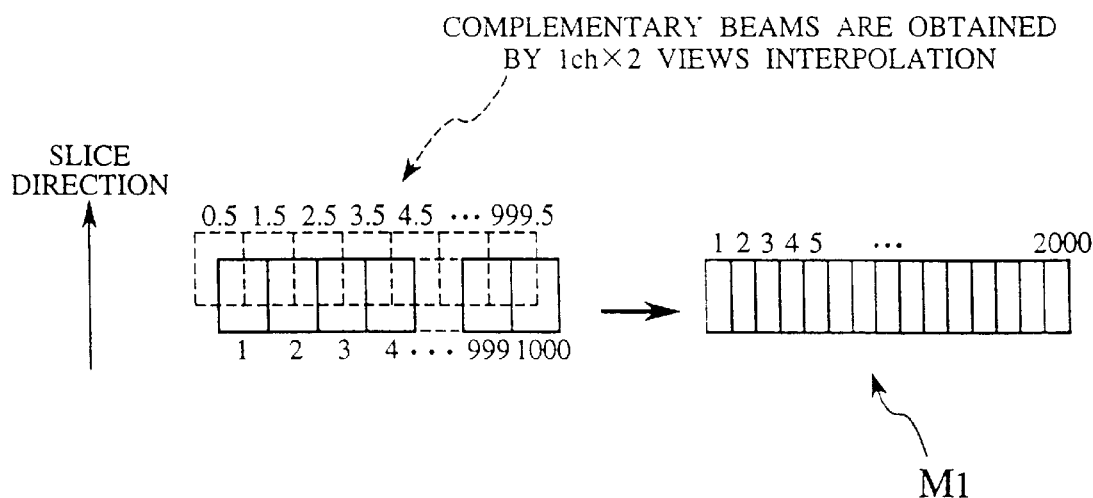
FIG. 10 is a conceptual view showing QQ.

The high density complementary data generating means 29P reads necessary data from the raw data memory 29B, and then generates the second high density data hp2 respectively for the data of the odd-numbered channels by virtue of interpolation of the data in the concerned one channel× two views in the way of the QQ reconstruction set forth in the prior art (see FIG. 10, FIG. 11). Also, it generates the second high density data for the data of the even-numbered channels by virtue of the four point interpolation using the data of two channels acquired by the two views, like the data generated by the complementary beam interpolation method set forth in the prior art, and then stores the data into the interpolation data 2 memory 29G (step S23 in FIG. 55).

Equations for interpolation of the odd-numbered channels will be given in the following.

$$hp2(j, 2 \times k-1) = (1-w) \times D(Ix, y) + w \times D(Ix+1, y) \quad \text{[Equations 8]}$$

$$y = CentCH \times 2 - (k+0.5)$$
$$x = \{[(k+0.5 - CentCH) \times \phi]/[Nch \times 180] + 0.5\} \times Nview$$
$$Ix = int(x)$$
$$w = x - Ix$$

Equations for interpolation of the even-numbered channels will be given in the following.

$$hp2(j, 2 \times k) = (1-w) \times [D(Ix, Iy) + D(Ix, Iy+1)]/2 + w \times [D(Ix+1, Iy) + D(Ix+1, Iy+1)]/2 \quad \text{[Equations 9]}$$

$$y = CentCH \times 2 - k$$
$$x = \{[(k - CentCH) \times \phi]/[Nch \times 180] + 0.5\} \times Nview$$
$$Ix = int(x)$$
$$w = x - Ix$$

Otherwise, the data of the even-numbered channels may be generated by interpolating the data of the odd-numbered channels obtained by the interpolation equations for the odd-numbered channels (Equations 8) as discussed in ①. Furthermore, if the sequence of generating the first and second high density data may be reversed, first the high density complementary data as the second high density data may be generated and then the high density direct data as the first high density data may be generated.

③ Helical interpolation process

The helical interpolation means 29R reads the first high density data (direct data) and the second high density data (complementary data) from the interpolation data 1 memory 29D and the interpolation data 2 memory 29G respectively, then generates the data at the target slice position by executing the helical interpolation in the slice direction, and then stores the data into the interpolation data 3 memory 29I (step S25). Either the two-point interpolation in the first embodiment or the filtering process in the slice direction in the fourth embodiment may be employed as the interpolation. Also, the out-of-focus process (Debluring process) in the channel direction or the slice direction may be applied.

④ Fan-beam reconstruction process

The image reconstructing portion 31 executes the normal fan-beam reconstruction while using the high density data stored in the interpolation data 3 memory 29I to thus generate the image (step S19). Either the filtered back projection method used in the first embodiment or a combination of the fan-parallel transformation and the Fourier inverse transformation may be used as the reconstruction to be applied.

Figure 56:
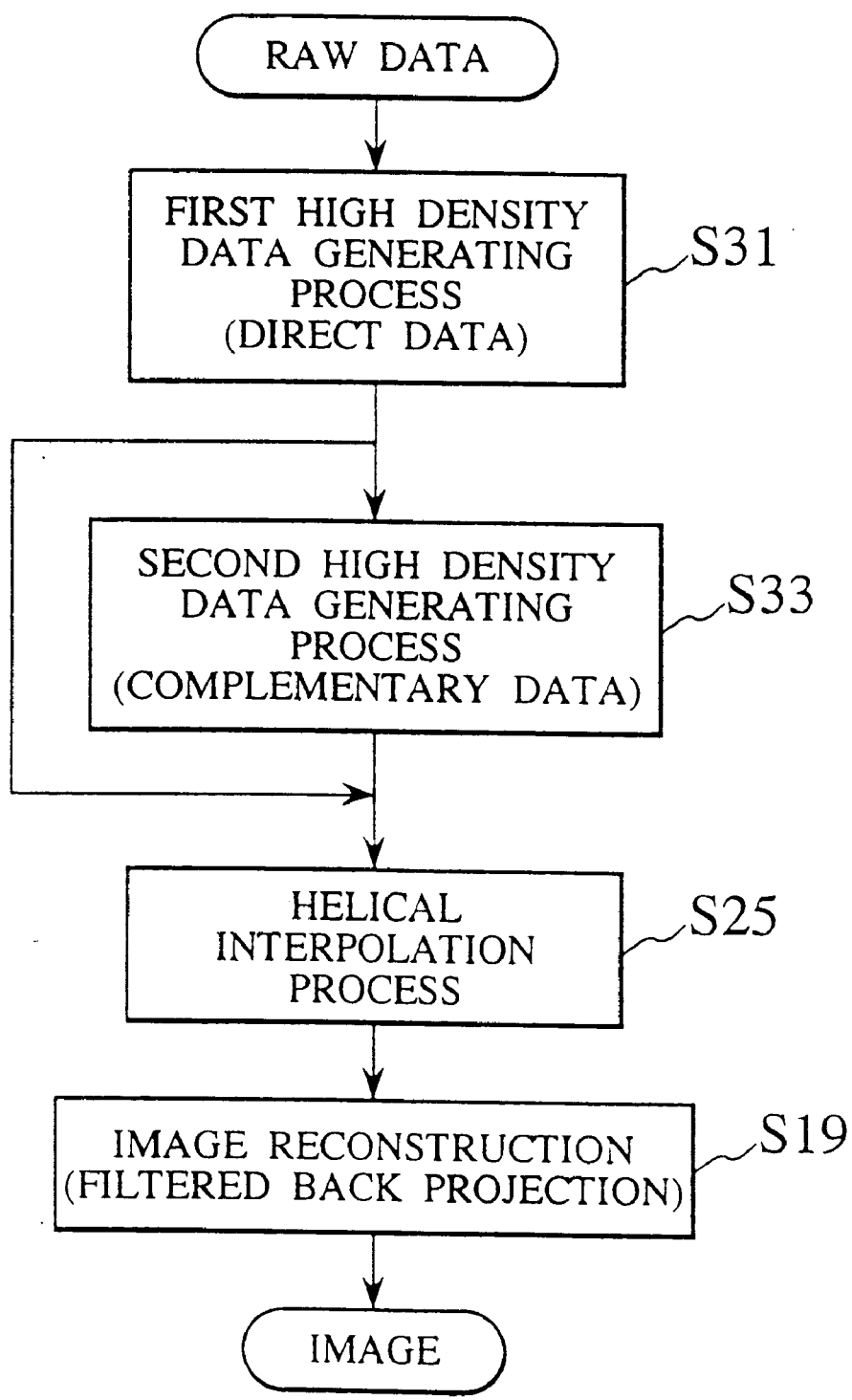
FIG. 56 is a flowchart showing flow of process in a modification of the sixth embodiment.

FIG. 56 is a flowchart showing a modification of the sixth embodiment. As shown in FIG. 56, the first and second high density data generating processes are carried out based on the raw data respectively in the sixth embodiment, but the second high density data may be generated by use of the generated result of the first high density data. Process procedures of the modification will be explained hereunder.

① First high density data (direct data) generation process

The high density direct data generating means 29Q receives the direct data 1 and the direct data 2 from the raw data memory 29B, then generates a first high density data group hp3 by applying contiguous channel interpolation in the same view to respective direct data according to following equations, and then stores the data into the interpolation data 1 memory 29D (step S31 in FIG. 56). Weight of interpolation is constant over all channels.

If the direct data of the k-th channel in the j-th view is assumed as $D(j,k)$, it is possible to formulate following equations.

$$hp3(j, 1) = D(j, 1)$$

$$hp3(j, 2 \times k) = D(j, k)$$

$$hp3(j, 2 \times k+1) = [D(j, k) + D(j, k+1)]/2 \quad \text{[Equations 10]}$$

The interpolation data 1 are data of the first, second, third, . . . , 2000-th channels.

② Second high density data (complementary data) generation process

The high density complementary data generating means 29P reads necessary data from the interpolation data 1 memory 29D, and then generates the second high density data hp4 respectively for the data of the odd-numbered channels by virtue of interpolation of the data in the concerned one channel×two views in the way of the QQ reconstruction set forth in the prior art (see FIG. 10, FIG. 11). Also, it generates the second high density data for the data of the even-numbered channels by virtue of the four point interpolation using the data of two channels acquired by the two views, like the data generated by the complementary beam interpolation method set forth in the prior art, and then stores the data into the interpolation data 2 memory 29G (step S33 in FIG. 56).

Equations for interpolation will be given in the following.

For $1 \leq K \leq 2 \times N\text{ch}$ (=2000), $$hp4(j, K) = hp3(j+X(K), Y(K))$$

$$Y(K) = 2 \times N\text{ch} - K + 1$$

$$X(K) = \{[(K - \text{Cent}CH) \times \phi]/[N\text{ch} \times 180] + 0.5\} \times N\text{view}$$

$$\text{Cent}CH = (2 \times N\text{ch} + 1)/2 \quad \text{[Equations11]}$$

Since the helical interpolation process (step S25 in FIG. 56) and the image reconstruction process (step S19 in FIG. 56) using the first and second high density data hp3, hp4 obtained as above are similar to those in the sixth embodiment itself, their explanation will be omitted.

The sixth embodiment and its modification explained above may be combined arbitrarily with the second, third, fourth, fifth embodiments respectively. In other words, they may be combined with the Debluring process in the channel direction, applied to the multi-slice CT apparatus, combined with the slice direction filtering process, applied to the helical scan in terms of the high density sampling scan method in the multi-slice CT apparatus, etc.

If the present invention is applied to the multi-slice CT apparatus, explanation has been made in the embodiments under the assumption that the number of detector column is set to four. But the number is not limited to four, it is evident that the present invention can be applied to the multi-slice CT equipment having any number of detector column such as two, three, five, six, seven, eight columns, etc.

In addition, the image reconstruction is not limited to the filtered back projection method (convolution method) (including the method based on the data obtained by the fan-parallel transformation). It is evident that various image reconstruction methods such as back projection operation using fast Fourier transformation (FFT), an image reconstruction method using Fourier transformation and inverse Fourier transformation, image reconstruction method by virtue of linogram, etc. may be employed.

Figure 57:
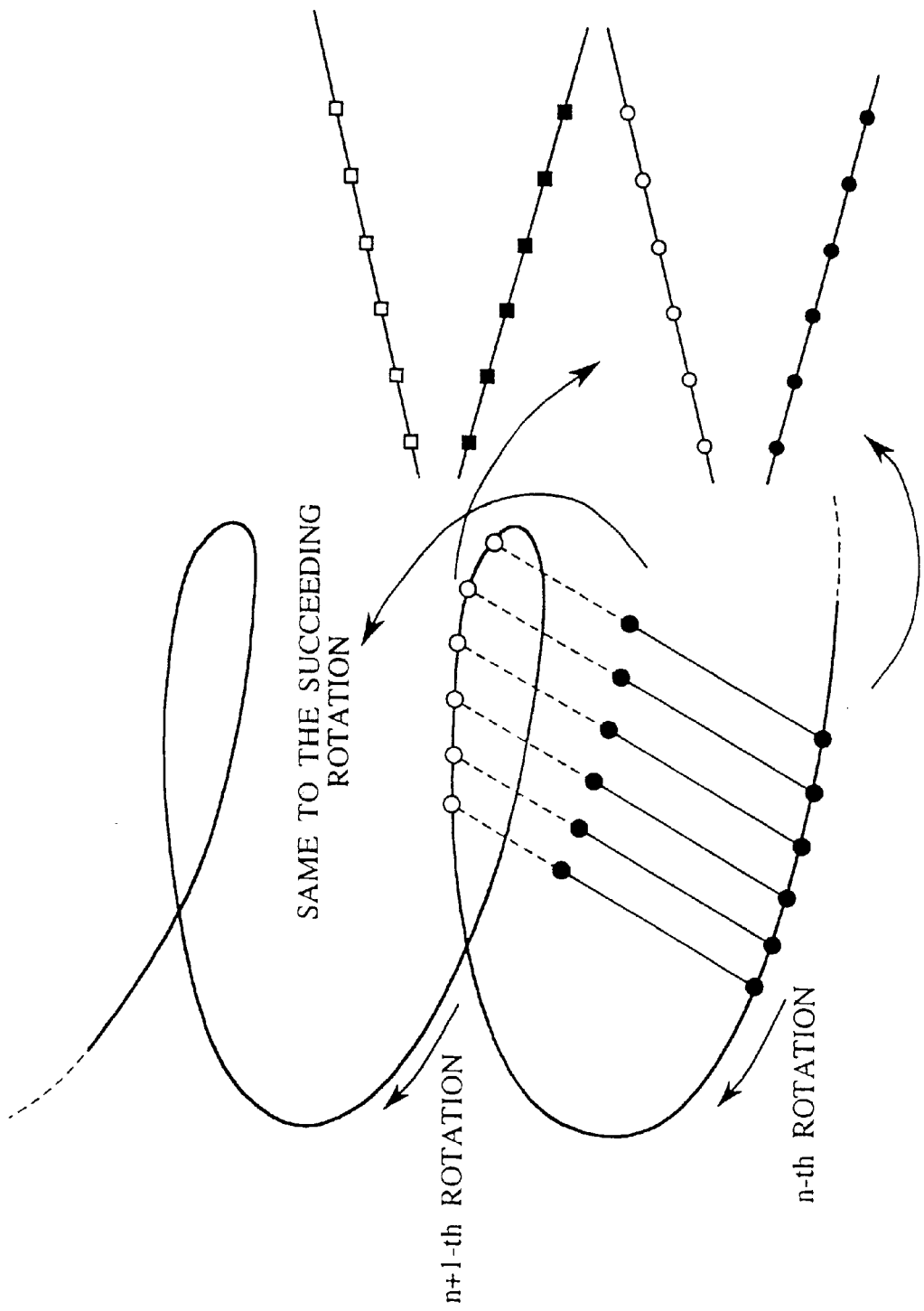
FIG. 57 is a conceptual view showing process for generating high density sampling data while executing fan-parallel transformation.

As another modification of the sixth embodiment, such an approach may be applied in which the helical interpolation data having high sampling density can be generated by generating data groups having high sampling density in the channel direction in the fan-parallel transformation and then applying the helical interpolation process in the body axis direction to the data groups. FIG. 57 is a conceptual view of such approach.

First, data indicated by black round marks can be obtained by executing the fan-parallel transformation of the data acquired at the focus position of the n-th rotation on this side. At this time, data sampling density is higher than the original sampling density of the detector system. Then, data indicated by white round marks can be obtained by executing the fan-parallel transformation of the data acquired at the focus position of the n-th rotation on the opposite side. Similarly, data indicated by black square marks and data indicated by white square marks can be obtained by processing the data of the n+1-th rotation.

Here the helical interpolation data with high sampling density can be obtained by executing the helical interpolation in the slice direction by use of these data groups.

Moreover, the high density data having double density have been generated from the raw data in the sixth embodiment, but it is within the range of the present invention to reconstruct the image by generating the high density data having treble, quadruple, etc. density in place of double density. For instance, if the high density data having treble density are to be generated, a number less than a decimal point of the decimal channel may be set to 0.33 and 0.67. If the high density data having quadruple density are to be generated, a number less than a decimal point of the decimal channel may be set to 0.25, 0.5, and 0.75.

In summary, as explained above, according to the X-ray CT apparatus of the present invention, the interpolation process and the image reconstruction are executed by using the high density data generated from the data acquired in the helical scan. Therefore, the image having both the high spatial resolution of the trans-axial plane like the QQ reconstruction image and the high continuity in the body axis direction like the 360° interpolation image or the complementary beam interpolation image can be reconstructed.

In addition, the spatial resolution of the trans-axial plane can be further improved by the Debluring process in the channel direction. In this case, increase in a calculation time can also be prevented.

The high quality image in which influence of change of the subject along the body axis can be suppressed and the resolution of the trans-axial plane can be enhanced can be realized by applying to the multi-slice CT.

According to the thinner basic slice thickness and the filtering process in the slice direction, the high quality image in which the partial volume effect can be suppressed and which have less artifact can be realized. If the filter selected by the filtering process in the slice direction is set to the low resolution function, the high quality image like the stack-processed image can be realized. If the Debluring process in the slice direction is executed by setting the filter as the extra-high resolution function, the spatial resolution in the slice direction can be further improved.

In addition, the high quality image having less artifact can be realized by the high density sampling scan method. Besides, according to the this disclosure of the present invention, one skilled in the art can apply various modifications within the range not to change the gist of the present invention.

The above process sequence or method of the process can be modified appropriately in all above embodiments. It is more important to be equivalent mathematically or same in the philosophy of the present invention.

What is claimed is:

1. An X-ray CT apparatus comprising:
    an X-ray beam generating source;
    detecting means having at least two detector columns along a slice direction of a subject, for detecting an X-ray generated from the X-ray beam generating source;

moving means for moving a patient couch or a rotating gantry, on which the subject is laid down, along a body axis direction of the subject;

data acquiring means for acquiring data via the detecting means; and data processing means for processing data acquired by the data acquiring means to execute image reconstruction based on data which has been subjected to data processing;

wherein the X-ray beam is generated while rotating the X-ray beam generating source and at the same time the patient couch or the rotating gantry is moved by the moving means such that the subject can be scanned in a helical manner to acquire data via the detecting means according to a high density sample scan method and to thus execute image reconstruction, and the data processing means generates data having a sampling pitch which is finer than a sampling pitch of data acquired by the detecting means (fine pitch data) and then executes image reconstruction based on the fine pitch data.

2. An X-ray CT apparatus comprising:

an X-ray beam generating source;

detecting means having at least two detector columns along a slice direction of a subject, for detecting an X-ray generated from the X-ray beam generating source;

moving means for moving a patient couch or a rotating gantry, on which the subject is laid down, along a body axis direction of the subject;

data acquiring means f or acquiring data via the detecting means; and data processing means for processing data acquired by the data acquiring means to execute image reconstruction based on data which has been subjected to data processing;

wherein the X-ray beam is generated while rotating the X-ray beam generating source and at the same time the patient couch or the rotating gantry is moved by the moving, means such that the subject can be scanned in a helical manner to acquire data via the detecting means according to a high density sampling scan method and to thus execute image reconstruction, and the data processing means generates data having sampling points which is larger than sampling points of data acquired by the detecting means (large sampling point data) and then executes image reconstruction based on the large sampling point data.

3. An X-ray CT apparatus comprising:

an X-ray beam generating source;

detecting means having one or plural detector columns along a slice direction of a subject, for detecting an X-ray generated from the X-ray beam generating source;

moving means for moving a patient couch or a rotating gantry, on which the subject is laid down, along a body axis direction of the subject;

data acquiring means for acquiring data via the detecting means; and data processing means for processing data acquired by the data acquiring means to execute image reconstruction based on data which has been subjected to data processing;

wherein the X-ray beam is generated while rotating the X-ray beam generating source and at the same time the patient couch or the rotating gantry is moved by the moving means such that the subject can be scanned in a helical manner to acquire data via the detecting means and to thus execute image reconstruction, and the data processing means includes, first processed data generating means for generating first processed data by processing a first group of data acquired via the detecting means, second processed data generating means for generating second processed data by processing a second group of data acquired via the detecting means, and third processed data generating means for generating third processed data, based on the first processed data generated by the first processed data generating means and the second processed data generated by the second processed data generating means, whereby image reconstruction is executed based on the third processed data.

4. The X-ray CT apparatus according to claim 3, wherein the first group of data and the second group of data consist of two data portions respectively, and data process executed respectively by the first processed data generating means, the second processed data generating means, and the third processed data generating means is interpolation process.

5. The X-ray CT apparatus according to claim 3, wherein the first group of data and the second group of data consist of at least three data portions respectively, and data process executed respectively by the first processed data generating means, the second processed data generating means, and the third processed data generating means is filter interpolation process.

6. The X-ray CT apparatus according to claim 3, wherein the first group of data is a group of direct data, and the second group of data is a group of complementary data.

7. The X-ray CT apparatus according to claim 4, wherein the first group of data is a group of direct data, and the second group of data is a group of complementary data.

8. The X-ray CT apparatus according to claim 5, wherein the first group of data is a group of direct data, and the second group of data is a group of complementary data.

9. The X-ray CT apparatus according to claim 3, wherein the data processing means further applies Debluring process, which recovers out-of-focus caused by data processing, to at least one of the first processed data, the second processed data, or the third processed data along a channel direction.

10. The X-ray CT apparatus according to claim 4, wherein the data processing means further applies Debluring process, which recovers out-of-focus caused by data processing, to at least one of the first processed data, the second processed data, or the third processed data along a channel direction.

11. The X-ray CT apparatus according to claim 5, wherein the data processing means further applies Debluring process, which recovers out-of-focus caused by data processing, to at least one of the first processed data, the second processed data, or the third processed data along a channel direction.

12. The X-ray CT apparatus according to claim 6, wherein the data processing means further applies Debluring process, which recovers out-of-focus caused by data processing, to at least one of the first processed data, the second processed data, or the third processed data along a channel direction.

13. The X-ray CT apparatus according to claim 5, wherein at least one of the filter interpolation processes executed respectively by the first data generating means, the second data generating means, and the third data generating means further applies Debluring process, which recovers out-of-focus caused by the filter interpolation process, along a slice direction.

14. The X-ray CT apparatus according to claim 8, wherein at least one of the filter interpolation processes executed respectively by the first data generating means, the second data generating means, and the third data generating means further applies Debluring process, which recovers out-of-focus caused by the filter interpolation process, along a slice direction.

15. The X-ray CT apparatus according to claim 11, wherein at least one of the filter interpolation processes executed respectively by the first data generating means, the second data generating means, and the third data generating means further applies Debluring process, which recovers out-of-focus caused by the filter interpolation process, along a slice direction.

16. The X-ray CT apparatus according to claim 3, wherein a number of the detector column in the detecting means is at least two, and the X-ray CT apparatus further executes a helical scan according to a high density sampling scan method.

17. The X-ray CT apparatus according to claim 4, wherein a number of the detector column in the detecting means is at least two, and the X-ray CT apparatus further executes a helical scan according to a high density sampling scan method.

18. The X-ray CT apparatus according to claim 5, wherein a number of the detector column in the detecting means is at least two, and the X-ray CT apparatus further executes a helical scan according to a high density sampling scan method.

19. The X-ray CT apparatus according to claim 6, wherein a number of the detector column in the detecting means is at least two, and the X-ray CT apparatus further executes a helical scan according to a high density sampling scan method.

20. The X-ray CT apparatus according to claim 7, wherein a number of the detector column in the detecting means is at least two, and the X-ray CT apparatus further executes a helical scan according to a high density sampling scan method.

21. The X-ray CT apparatus according to claim 8, wherein a number of the detector column in the detecting means is at least two, and the X-ray CT apparatus further executes a helical scan according to a high density sampling scan method.

22. The X-ray CT apparatus according to claim 9, wherein a number of the detector column in the detecting means is at least two, and the X-ray CT apparatus further executes a helical scan according to a high density sampling scan method.

23. The X-ray CT apparatus according to claim 10, wherein a number of the detector column in the detecting means is at least two, and the X-ray CT apparatus further executes a helical scan according to a high density sampling scan method.

24. The X-ray CT apparatus according to claim 11, wherein a number of the detector column in the detecting means is at least two, and the X-ray CT apparatus further executes a helical scan according to a high density sampling scan method.

25. The X-ray CT equipment according to claim 12, wherein a number of the detector column in the detecting means is at least two, and the X-ray CT apparatus further executes a helical scan according to a high density sampling scan method.

26. The X-ray CT apparatus according to claim 13, wherein a number of the detector column in the detecting means is at least two, and the X-ray CT apparatus further executes a helical scan according to a high density sampling scan method.

27. The X-ray CT apparatus according to claim 14, wherein a number of the detector column in the detecting means is at least two, and the X-ray CT apparatus further executes a helical scan according to a high density sampling scan method.

28. The X-ray CT apparatus according to claim 15, wherein a number of the detector column in the detecting means is at least two, and the X-ray CT apparatus further executes a helical scan according to a high density sampling scan method.

29. An X-ray CT apparatus comprising:
an X-ray beam generating source;
detecting means having one or plural detector columns along a slice direction of a subject, for detecting an X-ray generated from the X-ray beam generating source;
moving means for moving a patient couch or a rotating gantry, on which the subject is laid down, along a body axis direction of the subject;
data acquiring means for acquiring data via the detecting means; and
data processing means for processing data acquired by the data acquiring means to execute image reconstruction based on data which has been subjected to data processing;
wherein the X-ray beam is generated while rotating the X-ray beam generating source and at the same time the patient couch or the rotating gantry is moved by the moving means such that the subject can be scanned in a helical manner to acquire data via the detecting means and to thus execute image reconstruction, and
the data processing means includes,
first processed data generating means for generating a first group of processed data composed of high density direct data by executing interpolation process of a first group of data acquired via the detecting means along a channel direction,
second processed data generating means for generating a second group of processed data composed of high density complementary data from the first group of data, and
third processed data generating means for generating third processed data at target slice position by executing helical interpolation process, based on the first group of processed data and the second group of processed data.

30. An X-ray CT apparatus comprising:
an X-ray beam generating source;
detecting means having one or plural detector columns along a slice direction of a subject, for detecting an X-ray generated from the X-ray beam generating source;
moving means for moving a patient couch or a rotating gantry, on which the subject is laid down, along a body axis direction of the subject;
data acquiring means for acquiring data via the detecting means; and
data processing means for processing data acquired by the data acquiring means to execute image reconstruction based on data which has been subjected to data processing;
wherein the X-ray beam is generated while rotating the X-ray beam generating source and at the same time the patient couch or the rotating gantry is moved by the moving means such that the subject can be scanned in a helical manner to acquire data via the detecting means and to thus execute image reconstruction, and the data processing means includes, first processed data generating means for generating a first group of processed data composed of high density direct data by executing interpolation process of a first group of data acquired via the detecting means along a channel direction, second processed data generating means for generating a second group of processed data composed of high density complementary data from the first group of processed data, and third processed data generating means for generating third processed data at target slice position by executing helical interpolation process, based on the first group of processed data and the second group of processed data, whereby image reconstruction is executed based on the third processed data.

* * * * *